United States Patent [19]
Amara et al.

[11] Patent Number: 5,776,774
[45] Date of Patent: Jul. 7, 1998

[54] AMINO ACID TRANSPORTERS AND USES

[75] Inventors: Susan G. Amara; Jeffrey L. Arriza, both of Portland, Oreg.

[73] Assignee: State of Oregon, Portland, Oreg.

[21] Appl. No.: 546,666

[22] Filed: Oct. 23, 1995

Related U.S. Application Data

[62] Division of Ser. No. 140,729, Oct. 20, 1993.

[51] Int. Cl.$^6$ ............... C12N 5/00; C12N 1/20; C12N 15/00; C07H 21/04

[52] U.S. Cl. ............ 435/325; 435/252.3; 435/320.1; 536/23.5; 536/24.3

[58] Field of Search ............ 435/6, 69.1, 240.2, 435/320.1, 252.3; 536/23.5, 24.3

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 5,424,185 | 6/1995 | Lam et al. | 435/6 |

OTHER PUBLICATIONS

Anderson et al. (1989) J. Biol. Chem. 264:8222–8229.
Arriza et al. (1992) J. Neurosci. 12:4045–4055.
Arriza et al. (1994) J. Neurosci. 14(9):5559–5569.
Bertling (1987) Bioscience Reports 7:107–112.
Blakely et al. (1991) Anal. Biochem. 194:302–308.
Bouvier et al. (1992) Nature 360:471–474.
Bussolati et al. (1992) J. Biol. Chem. 267: 8330–8335.
Choi et al. (1987) Neurosci. 7:357–358.
Chomczynski & Sacchi (1987) Anal. Biochem. 162:156–159.
Christensen (1990) Physiol. Rev. 70: 43:77.
Christensen et al. (1967) J. Biol. Chem. 242:5237–5246.
Eisenberg et al. (1984) J. Molec. Biol. 179:125–142.
Engelke et al. (1992) J. Bacteriol. 171:5551–5560.
Felgner et al. (1987) Proc. Natl. Aced. Sci. USA 84:7413–7417.
Gluzman (1981) Cell 23:175–182.
Guastella et al. (1992) Proc. Natl. Acad. Sci. USA 89:7189–7193.
Kanai et al. (1993) Trends in Neurosci. 16(9):365–370.
Kanner & Schuldiner (1987) CRC Crit. Rev. Biochem. 22:1–38.
Kanner (1993) FEBS Lett. 325(1.2):95–99.
Kavanaugh et al. (1992) J. Biol. Chem. 267:22007–22009.
Kim et al. (1991) Nature 352:725–728.
Kong et al. (1993) J. Biol. Chem. 268:1509–1512.
Kozak (1987) Nucleic Acids Res 15:8125–8132.
Maenz et al. (1992) J. Biol. Chem. 267:1510–1516.
Makowske & Christensen (1982) J. Biol. Chem. 257: 14635–14638.
Nicholls & Attwell (1990) Tips 11:462–468.
Olney et al. (1990) Science 248:596–599.
Pines et al. (1992) Nature 360:464–467.
Saiki et al. (1988) Science 239:487–491.
Sanger et al. (1977) Proc. Natl. Acad. Sci. USA 74:5463.
Schloss et al. (1992) FEBS Lett. 307(1):76–80.
Shashidharan et al., (1993) Biochem. Biophys. Acta. 1216:161–164.
Smith and Johnson (1988) Gene 67:31–40.
Smithies et al. (1985) Nature 317:230–234.
Storck et al. (1992) Proc. Natl. Acad. Sci. USA 89: 10955–10959.
Thomas & Capecchi (1987) Cell 51:503–512.
Uhl (1992) Trends in Neurosci. 15(7): 265–268.
Wallace et al. (1990) J. Bacteriol. 172: 3214–3220.
Wang et al. (1991) Nature 352:729–731.
Georgiou, G. (1988) AIChE J. 34(8):1233–1248.
Kanai et al. (1992) Nature 360:467–471.
Kanai et al. (1993) FASEB J. 7(15):1450–1459.
Kanai et al. (1994) J. Biol. Chem. 269(32):10599–10606.
Stelzner et al. (1993) FASEB J. 7(4/part 2): A575.

*Primary Examiner*—Robert A. Wax
*Assistant Examiner*—Lisa J. Hobbs
*Attorney, Agent, or Firm*—McDonnell, Boehnen Hulbert & Berghoff

[57] ABSTRACT

The present invention relates to novel mammalian amino acid transporter proteins and the genes that encode such proteins. The invention is directed toward the isolation, characterization and pharmacological use of the human amino acid transporter proteins EAAT1, EAAT2, EAAT3 and ASCT1. The invention specifically provides isolated complementary DNA copies of mRNA corresponding to each of these transporter genes. Also provided are recombinant expression constructs capable of expressing each of the amino acid transporter genes of the invention in cultures of transformed prokaryotic and eukaryotic cells, as well as such cultures of transformed cells that synthesize the human amino acid transporter proteins encoded therein. The invention also provides methods for screening in vitro compounds having transport-modulating properties using preparations of transporter proteins from such cultures of cells transformed with recombinant expression constructs.

4 Claims, 42 Drawing Sheets

FIG. 1A

```
                                    CACCTCTAGC  TCGGAGCGGC  GTGTAGCGCC  ATG  GAG  AAG  AGC  AAC  GAG  ACC  AAC     54
                                                                        Met  Glu  Lys  Ser  Asn  Glu  Thr  Asn
                                                                         1                   5

GGC  TAC  CTT  GAC  AGC  GCT  CAG  GCG  GGG  CCT  GGG  GCC  GGA  CCC  GCT                                         102
Gly  Tyr  Leu  Asp  Ser  Ala  Gln  Ala  Gly  Pro  Gly  Ala  Gly  Pro  Ala
     10                      15                      20

CCG  GGG  ACC  GCG  GGA  CGC  GCA  CGG  TGC  CGT  GCG  GGC  CCG  CGG                                              150
Pro  Gly  Thr  Ala  Gly  Arg  Ala  Arg  Cys  Arg  Ala  Gly  Pro  Arg
 25                      30                 35                      40

CGC  CAA  GCG  CTG  GTG  CTC  TCC  AGC  CTG  GTG  ACC  TTG  CGC  GGG                                              198
Arg  Gln  Ala  Leu  Val  Leu  Ser  Ser  Leu  Val  Thr  Leu  Arg  Gly
                         45        50                                55

GGC  CTG  GCC  TTC  GGG  GCG  CTC  CTG  ATG  GAG  GGG  CCC  TTC  AGC  CGC                                         246
Gly  Leu  Ala  Phe  Gly  Ala  Leu  Leu  Met  Glu  Gly  Pro  Phe  Ser  Arg
          60                                    80

ACC  TAC  GCC  GCC  AGC  ATG  CGC  CTC  CTG  ACG  CAG  CTG  CGC  ATG  GTC                                         294
Thr  Tyr  Ala  Ala  Ser  Met  Arg  Leu  Leu  Thr  Gln  Leu  Arg  Met  Val
     75                 85                 70

ATC  CTG  CCG  GTG  TGC  GTC  AGC  CTG  GTG  CTG  GCC  GGC  TCG  GCC                                              342
Ile  Leu  Pro  Val  Cys  Val  Ser  Leu  Val  Leu  Ala  Gly  Ser  Ala
 90                 95                      100
```

FIG. 1B

```
CTC GAT GCC AGC TGC CTC GGG CGT CTG GGC ATC CGT GTC GCC TAC                390
Leu Asp Ala Ser Cys Leu Gly Arg Leu Gly Ile Arg Val Ala Tyr
105                 110                 115                 120

TTT GGC CTC ACC ACA CTG AGT CGT CTG GCG GCC GTG GCC TTG GCG                438
Phe Gly Leu Thr Thr Leu Ser Arg Leu Ala Ala Val Ala Leu Ala
                125                 130                 135

TTC ATC AAG CCA GGA TCC GGT GCG CAG CTT ACC CAG TCC AGC GAC                486
Phe Ile Lys Pro Gly Ser Gly Ala Gln Leu Thr Gln Ser Ser Asp
        140                 145                 150

CTG GGG GAC TCG GGG CCT CCT GTC CCC AAA GAG ACG GTG                        534
Leu Gly Asp Ser Gly Pro Pro Val Pro Lys Glu Thr Val
155                 160                 165

GAC TCT TTC CTC GAC CTG GCC TAT CCC TCC AAT GTC CTT GTG                    582
Asp Ser Phe Leu Asp Leu Ala Tyr Pro Ser Asn Val Leu Val
170                 175                 180

GCA GCT TTC CGT ACG GAT GCA AGA AAC CTG GAT TAT AAG GAA                    630
Ala Ala Phe Arg Thr Asp Ala Arg Asn Leu Asp Tyr Lys Glu
185                 190                 195                 200

AGC AGC TCT GGA AAC AGC CAT GAA AAG ATC CCC ATA GGC ACT                    678
Asn Ser Ser Gly Val Thr His Glu Lys Pro Ile Gly Thr
            205                 210                 215
```

FIG. 1C

| Codon | AA | Pos | Codon | AA | Pos | Codon | AA | Pos | Codon | AA | Pos | Codon | AA | Pos | Codon | AA | Pos | Codon | AA | Pos | Codon | AA | Pos | Offset |
|---|---|---|---|---|---|---|---|---|---|---|---|---|---|---|---|---|---|---|---|---|---|---|---|---|
| GAG | Glu |  | ATA | Ile |  | GGG | Gly | 220 | GAA | Glu |  | ATG | Met |  | AAC | Asn |  | ATT | Ile |  | TTA | Leu |  | 726 |
| TTA | Leu |  | CGA | Gly |  | GCC | Ala |  | TTA | Leu |  | GTG | Val | 235 | TTC | Phe |  | AAA | Lys |  | CTA | Leu | 240 | 774 |
| CGT | Arg |  | TTC | Phe | 250 | AAT | Asn |  | TCC | Ser |  | CTC | Leu |  | AAC | Asn | 255 | GAG | Glu |  | GCG | Ala |  | 822 |
| ATT | Ile | 265 | ATG | Met |  | GTA | Val |  | CCT | Pro | 270 | GTG | Val |  | ATC | Ile |  | ATG | Met |  | GGC | Gly |  | 870 |
| ATC | Ile |  | GTG | Val |  | GAA | Glu |  | AAA | Lys | 285 | ATC | Ile |  | GAC | Asp |  | ATC | Ile |  | CTG | Leu | 290 | 918 |
| TAC | Tyr |  | ATC | Ile |  | GCA | Ala | 300 | TCT | Ser |  | TTG | Leu |  | ATA | Ile |  | GGC | Gly |  | CAT | His | 305 | 966 |
| CTG | Leu |  | CCA | Pro |  | ATT | Ile |  | TAT | Tyr |  | TTT | Phe |  | GTT | Val |  | TTC | Phe | 320 | ACA | Thr |  | 1014 |

| Codon | AA | Pos | Codon | AA | Pos | Codon | AA | Pos | Codon | AA | Pos | Codon | AA | Pos | Codon | AA | Pos | Codon | AA | Pos | Codon | AA | Pos |
|---|---|---|---|---|---|---|---|---|---|---|---|---|---|---|---|---|---|---|---|---|---|---|---|
| GGA | Gly | 225 | TTG | Leu |  | GTC | Val |  | CTG | Leu |  | TTT | Phe |  | GCT | Ala | 230 | CTG | Leu |  | GTG | Val |  |
| TCC | Ser |  | GGC | Gly |  | TCC | Ser |  | GAA | Glu | 245 | GGA | Gly |  | GAC | Asp |  | CTC | Leu |  | ATC | Ile |  |
| ACG | Thr |  | ATG | Met |  | GTG | Val | 260 | CTG | Leu |  | GTG | Val |  | TCC | Ser |  | TGG | Trp |  |   |   |   |
| ATC | Ile |  | TTC | Phe | 275 | CCT | Leu |  | GTT | Val |  | GGA | Gly |  | GTG | Val |  | AGC | Ser |  | AAG | Lys | 280 |
| GTG | Val |  | GTT | Val |  | ACC | Thr |  | AGC | Ser |  | CTG | Leu |  | GGG | Gly | 295 | AAA | Lys |  |   |   |   |
| GGA | Gly |  | ATT | Ile |  | CAT | His |  | GGA | Gly |  | GGA | Gly |  | GGA | Gly | 310 | ATT | Ile |  | GTT | Val |  |
| CGA | Arg |  | AAA | Lys |  | AAC | Asn |  | CCA | Pro | 325 | TTC | Phe |  | TTC | Phe |  | AGA | Arg |  | TTC | Phe |  |

FIG. 1D

| | | | | | | | | | | | | Pos |
|---|---|---|---|---|---|---|---|---|---|---|---|---|
| CTC Leu | CTG Leu 330 | GGC Gly | CTC Leu | GCC Ala | CCA Pro 335 | TTT Phe | TTT Phe 340 | GCT Ala | ACC Thr | TGC Cys | TCC Ser | 1062 |
| AGC Ser 345 | TCA Ser | GCG Ala | ACC Thr | CTT Leu | CCC Pro 350 | TCT Ser | ATG Met | ATG Met | AAG Lys | AAC Asn | AAT Asn 360 | 1110 |
| GGT Gly | GTG Val | GAC Asp | AAG Lys | AGG Arg 365 | AGC Ser | AGG Arg | TTT Phe | GCG Ala | ACA Thr | GCA Ala | TGC Cys 355 | 1158 |
| GTG Val | ATG Met | GAC Asp 380 | ATC Ile | AGC Ser | GCC Ala | TTC Phe | ATT Ile 370 | CTC Leu | CCC Pro | GAG Glu | AAT Asn 360 | 1206 |
| ATT Ile | GCG Ala | CTC Leu | AAC Asn | ATA Ile | GAG Glu 400 | TTC Phe 385 | ATT Ile 370 | GTG Val | CCG Ala 390 | GCC Ala | GTG Val 375 | 1254 |
| ATT Ile | CTA Leu 410 | ACT Thr | GCC Ala | TCC Ser | GCG Ala 415 | TCC Ser | AGT Ser | GTT Val | GGA Gly | GCA Ala 420 | GCC Ala | 1302 |
| GCT Ala 425 | GGG Gly | GTC Val | CTC Leu | ACC Thr 430 | ATT Ile | ATC Ile | ATC Ile | CTG Leu 435 | GAG Glu | GCC Ala | ATT Ile | 1350 |
| GGA Gly | | CCA Pro | CTG Leu 440 | | | | | | | | | |

(FIG. 1D — nucleotide and amino acid sequence, positions ~329 to 440, nucleotides 1062–1350)

FIG. 1E

| | | | | | | | | | | | | | | | |
|---|---|---|---|---|---|---|---|---|---|---|---|---|---|---|---|
| CCT Pro | ACT Thr | CAT His | GAC Asp | CTG Leu 445 | CCT Pro | CTG Leu | ATC Ile | GCT Ala 450 | GTG Val | GAC Asp | TGG Trp | ATT Ile | GTG Val 455 | GAC Asp | 1398 |
| CGG Arg | ACC Thr | ACG Thr 460 | GTG Val | GTG Val | AAT Asn | GAG Glu 465 | GTG Val | GAT Asp | GCC Ala | CTG Leu | GGT Gly 470 | GCA Ala | GGC Gly | | 1446 |
| ATT Ile | CTC Leu | CAC His 475 | CTG Leu | CTG Leu | AAT Asn | CAG Gln | AAG Lys 480 | ACA Thr | GCA Ala | AAA Lys | GGC Gly 485 | GAG Glu | CAG Gln | GAA Glu | 1494 |
| CTT Leu | GCT Ala 490 | GAG Glu | GTG Val | AAA Lys | GAA Glu 495 | GTG Val | GCC Ala | ATC Ile | CCC Pro | TGC Cys 500 | AAG Lys | TCT Ser | GAG Glu | GAG Glu | 1542 |
| GAG Glu 505 | ACA Thr | TCG Ser | CCC Pro | CTG Leu | GTG Val 510 | CAG Gln | CAC His | ACA Thr | AAC Asn | CCC Pro 515 | GCT Ala | GGC Gly | CCC Pro | GTG Val | 1590 |
| AGT Ser | GCC Ala | CCA Pro | GAA Glu | CTG Leu 525 | GAA Glu | TCC Ser | AAG Lys | GAG Glu | TCG Ser 530 | CTG Leu | GTT Val | CTG Leu | TGATGGGGCT | | 1636 |

GGGCTTTGGG CTTGCCTGCC AGCAGTGATG TCCCACCCTG TTCA      1680

FIG. 2A

| | | | | | | | | | | |
|---|---|---|---|---|---|---|---|---|---|---|
| AAAGAAGAGA | CCCTCCTAGA | AAAGTAAAAT | | | | | | | | |
| | | | ATG<br>Met<br>1 | ACT<br>Thr | AAA<br>Lys | AGC<br>Ser | AAT<br>Asn | GGA<br>Gly<br>5 | GAA<br>Glu | GAG<br>Glu | 54 |
| CCC<br>Pro | AAG<br>Lys<br>10 | ATG<br>Met | GGG<br>Gly | GGC<br>Gly | AGG<br>Arg | ATG<br>Met<br>15 | GAG<br>Glu | TTC<br>Phe | CAG<br>Gln | CAG<br>Gln<br>20 | CTG<br>Arg | AAA<br>Lys | 102 |
| CGC<br>Arg<br>25 | ACA<br>Thr | CTT<br>Leu | TTG<br>Leu | GCC<br>Ala | AGG<br>Lys<br>30 | AAG<br>Lys | AAA<br>Lys | GTG<br>Val | CAG<br>Gln | AAC<br>Asn<br>35 | ACA<br>Thr | AAG<br>Lys | GAG<br>Glu<br>40 | GTT<br>Val | 150 |
| GTT<br>Val | AAA<br>Lys | AGT<br>Ser | TAC<br>Tyr | CTG<br>Leu<br>45 | TTT<br>Phe | CGG<br>Arg | AAT<br>Asn | GCT<br>Ala | TTT<br>Phe<br>50 | GTG<br>Val | CTG<br>Leu | CTC<br>Leu | ACA<br>Thr | GTC<br>Val<br>55 | ACC<br>Thr | 198 |
| GCT<br>Ala | GTC<br>Val | ATT<br>Ile | GGT<br>Gly<br>60 | GTG<br>Val | ACA<br>Thr | ATC<br>Ile | TTT<br>Phe | GGA<br>Gly<br>65 | CTT<br>Leu | TTC<br>Phe | ACC<br>Thr | CTC<br>Leu | CGA<br>Arg | CCA<br>Pro<br>70 | TAC<br>Tyr | AGA<br>Arg | 246 |
| ATG<br>Met | AGC<br>Ser | TAC<br>Tyr<br>75 | CGG<br>Arg | GAA<br>Glu | AAG<br>Lys | TAC<br>Tyr<br>80 | TTC<br>Phe | TCC<br>Ser | TTT<br>Phe | CCT<br>Pro | GGG<br>Gly<br>85 | GAA<br>Glu | CTT<br>Leu | CTG<br>Leu | 294 |
| ATG<br>Met | AGG<br>Arg<br>90 | ATG<br>Met | TTA<br>Leu | CAG<br>Gln | ATG<br>Met | CTG<br>Leu<br>95 | GTC<br>Val | GTA<br>Val | CCA<br>Pro | CTT<br>Leu | ATC<br>Ile<br>100 | TCC<br>Ser | AGT<br>Ser | CTT<br>Leu | 342 |

FIG. 2B

| GTC | ACA | GGA | ATG | GCG | GCG | CTA | GAT | AGT | AAG | GCA | TCA | GGG | AAG | TGG | GAA | 390 |
| Val | Thr | Gly | Met | Ala | Ala | Leu | Asp | Ser | Lys | Ala | Ser | Gly | Lys | Trp | Glu | |
| 105 | | | | 110 | | | | | 115 | | | | | | 120 | |

| TGC | GGA | GCT | GTA | GTC | TAT | TAT | ATG | ACT | ACC | ACC | ATC | ATT | GCT | GTG | GTG | 438 |
| Cys | Gly | Ala | Val | Val | Tyr | Tyr | Met | Thr | Thr | Thr | Ile | Ile | Ala | Val | Val | |
| | | | | 125 | | | | | 130 | | | | | 135 | | |

| ATT | GGC | ATA | ATC | ATT | GTC | ATC | ATC | ATC | CAT | CCT | GGG | AAG | GGC | ACA | AAG | 486 |
| Ile | Gly | Ile | Ile | Ile | Val | Ile | Ile | Ile | His | Pro | Gly | Lys | Gly | Thr | Lys | |
| | Gly | | 140 | | | | 145 | | | | | 150 | | | | |

| GAA | AAC | ATG | CAC | AGA | GAA | GGC | AAA | ATT | ATT | GTA | CGA | GTG | ACA | GCT | GAT | 534 |
| Glu | Asn | Met | His | Arg | Glu | Gly | Lys | Ile | Ile | Val | Arg | Val | Thr | Ala | Asp | |
| | | 155 | | | | | 160 | | | | | | 165 | | | |

| GCC | TTC | CTG | GAC | TTG | ATC | AGG | ATG | TTA | AAT | CCA | AAT | CTG | GTA | GAA | 582 |
| Ala | Phe | Leu | Asp | Leu | Ile | Arg | Met | Leu | Asn | Pro | Asn | Leu | Val | Glu | |
| | 170 | | | | | 175 | | | | 180 | | | | | |

| GCC | TGC | TTT | AAA | GAG | TTT | ATC | AAC | ACC | TAT | GAG | AAG | AGC | TTT | AAA | 630 |
| Ala | Cys | Phe | Lys | Gln | Phe | Ile | Asn | Thr | Tyr | Glu | Lys | Ser | Phe | Lys | |
| 185 | | | | | 190 | | | | | 195 | | | | 200 | |

| GTG | CCC | ATC | GAG | AAC | GAA | CCT | ACG | GTG | GCT | GTG | ATA | AAT | 678 |
| Val | Pro | Ile | Gln | Asn | Glu | Leu | Thr | Val | Ala | Val | Ile | Asn | |
| | | | | 205 | | | 210 | | | | | 215 | |

FIG. 2C

| | | | | | | | | | | | | | | | |
|---|---|---|---|---|---|---|---|---|---|---|---|---|---|---|---|
| GTG Val | TCT Ser | GAG Glu | GCC Ala 220 | ATG Met | GAG Glu | ACT Thr | CTT Leu | ACC Thr 225 | CGA Arg | ATC Ile | ACA Thr | GAG Glu | GAG Glu 230 | CTG Leu | GTC Val | 726 |
| CCA Pro | GTT Val | CCA Pro 235 | GGA Gly | TCT Ser | GTG Val | AAT Asn | GGA Gly 240 | CTT Leu | AAT Asn | GCC Ala | CTG Leu | GGT Gly 245 | CTA Leu | GTT Val | GTC Val | 774 |
| TTC Phe | TCC Ser 250 | ATG Met | TCT Ser | TTC Phe | TGC Cys | TTC Phe | GGT Gly 255 | ATT Ile | GGA Gly | AAC Asn | ATG Met 260 | AAG Lys | GAA Glu | CAG Gln | GGG Gly | 822 |
| GAG Gln 265 | GCC Ala | CTG Leu | GAG Glu | AGA Arg | GAG Glu | TTT Phe 270 | GAT Asp | TCT Ser | CTT Leu | AAC Asn 275 | GAA Glu | GCC Ala | ATG Met | AGA Arg 280 | GGG Gly | 870 |
| CTG Leu | GTA Val | GCA Ala | ATA Ile 285 | ATG Met | TGG Trp | TAT Tyr | GCC Ala | CCC Pro 290 | GTG Val | GGT Gly | ATC Ile | ATG Met | ATT Ile 295 | CTG Leu | 918 |
| ATT Ile | AAG Lys 300 | ATT Ile | ATG Met | GAG Glu | GAA Glu 305 | GAC Asp | ATG Met | GGT Gly | GGG Gly | ATT Ile 310 | GGG Gly | TTC Phe | GGG Gly | 966 |
| CAG Gln | CTT Leu | GCC Ala 315 | ATG Met | TAC Tyr | ACC Thr | ACT Thr 320 | GTC Val | ATT Ile | GGC Gly | TTA Leu 325 | CTC Leu | ATT Ile | CAC His | 1014 |

FIG. 2D

```
GCA  GTC  ATC  TTG  CCA  CTC  CTC  TAC  TTC  TTG  GTA  ACA  CGG  AAA  AAC       1062
Ala  Val  Ile  Leu  Pro  Leu  Leu  Tyr  Phe  Leu  Val  Thr  Arg  Lys  Asn
     330            335                      340

CCT  TGG  GTT  ATT  GGA  GGG  TTG  CTG  CAA  GCA  CTC  ATC  ACC  GCT  CTG       1110
Pro  Trp  Val  Ile  Gly  Gly  Leu  Leu  Gln  Ala  Leu  Ile  Thr  Ala  Leu
345            350                      355                      360

GGG  ACC  TCT  AGT  TCT  GCC  ACC  CTA  CCC  ATC  ACC  TTC  AAG  TGC  CTG       1158
Gly  Thr  Ser  Ser  Ser  Ala  Thr  Leu  Pro  Ile  Thr  Phe  Lys  Cys  Leu
               365                      370                 375

GAA  AAT  TCA  GGC  GTG  GAC  AAG  CGC  GTC  ACC  AGA  TTC  GTG  CTC  CCC       1206
Glu  Asn  Ser  Gly  Val  Asp  Lys  Arg  Val  Thr  Arg  Phe  Val  Leu  Pro
     380                      385                      390

GTA  GGA  ACC  ATT  AAC  ATG  GAT  GGG  ACT  GCC  TAT  TTC  GAG  GCT  TTG       1254
Val  Gly  Thr  Ile  Asn  Met  Asp  Gly  Thr  Ala  Tyr  Phe  Glu  Ala  Leu
               395       400                      405

GCT  GCC  TTC  ATT  GCT  CAA  CAA  AAC  AAC  TTT  CTG  GAA  AAC  TTC  GGA       1302
Ala  Ala  Phe  Ile  Ala  Gln  Gln  Asn  Asn  Phe  Leu  Glu  Asn  Phe  Gly
410                      415                      420

CAA  ATT  ACA  ATC  AGC  ATC  ACA  GCC  ACA  GCT  GCC  AGT  ATT  GGG  GCA       1350
Gln  Ile  Thr  Ile  Ser  Ile  Thr  Ala  Thr  Ala  Ala  Ser  Ile  Gly  Ala
425                 430                      435                      440
```

FIG. 2E

| | | | | | | | | | | | | |
|---|---|---|---|---|---|---|---|---|---|---|---|---|
| GCT Ala | GGA Gly | ATT Ile | CCT Pro | CAG Gln 445 | GCG Ala | GGC Gly | CTG Leu | GTC Val | ACT Thr 450 | ATG Met | GTC Val | ATT Ile | GTG Val | CTG Leu 455 | ACA Thr | 1398 |
| TCT Ser | GTC Val | GGC Gly | CTG Leu 460 | CCC Pro | ACT Thr | GAC Asp | ATC Ile 465 | ACG Thr | CTC Leu | ATC Ile | GCG Ala 470 | GTG Val | GAC Asp | 1446 |
| TGG Trp | TTC Phe | TTG Leu 475 | GAT Asp | CGC Arg | ACC Thr 480 | CGG Arg | ACC Thr | GTA Val | CTG Leu 485 | GGA Gly | GAC Asp | TCC Ser | 1494 |
| CTG Leu | GGA Gly 490 | GCT Ala | CGC Arg | ATT Ile | GTG Val | GAG Glu 495 | CAC His | TTG Leu | TCA Ser | CGA Arg | CAT His 500 | GAA Glu | CTG Leu | AAC Asn | 1542 |
| AGA Arg 505 | GAT Asp | GTT Val | GAA Glu | ATG Met | GGT Gly 510 | TCA Ser | AAC Asn | TCA Ser | GTG Val | ATT Ile 515 | GAG Glu | GAA Glu | ATT Ile | GAA Glu | ATG Met | AAG Lys 520 | 1590 |
| AAA Lys | CCA Pro | TAT Tyr | CAA Gln | CTG Leu 525 | ATT Ile | GCA Ala | CAG Gln | GAC Asp | AAT Asn 530 | GAA Glu | ACT Thr | GAG Glu | AAA Lys | CCC Pro 535 | ATC Ile | 1638 |
| GAC Asp | AGT Ser | GAA Glu | ACC Thr 540 | AAG Lys | ATG Met | TAGACTAACA | TAAAGAAACA | CTTT | 1680 |

FIG. 3A

```
                    GATAGTGCTG AAGAGGAGG GCGTTCCCAG ACC ATG GCA TCT ACG GAA GGT GCC    54
                                                        Met Ala Ser Thr Glu Gly Ala
                                                         1               5

AAC AAT ATG CCC AAG CAG GTG GAA CGA ATG GCA CCA GAC AGT CAT CTT                       102
Asn Asn Met Pro Lys Gln Val Glu Arg Met Ala Pro Asp Ser His Leu
         10              15              20

GGC TCA GAG GAA CCC AAG CAC CGG CTG CTG GGC GGC CTG CGC CTG GAC                       150
Gly Ser Glu Glu Pro Lys His Arg Leu Leu Gly Gly Leu Arg Leu Asp
    25              30              35

AAG CTG GGA AAG AAT CTG CTG ACC CTG ACG GTG TTT GGT CCC ATC ATC                       198
Lys Leu Gly Lys Asn Leu Leu Thr Leu Thr Val Phe Gly Pro Ile Ile
 40              45              50              55

CTG GGA GCA GTG TGT CTT CGC TTC CTT GCA TCT CCC ATC CAC ATC ATG                       246
Leu Gly Ala Val Cys Leu Arg Phe Leu Ala Ser Pro Ile His Ile Met
                     60              65              70

CCT GAT GTT ATG CCA TTC GCC ATA GAT TCC ATC CTC ATG AGG                               294
Pro Asp Val Met Pro Phe Ala Ile Asp Ser Ile Leu Met Arg
         75              80              85

ATG AAA CTA ATT CTG GGT GGT AGC TCC ATC TTA ATC ACA                                   342
Met Lys Leu Ile Leu Gly Gly Ser Ser Ile Leu Ile Thr
     90              95             100
```

FIG. 3B

| | | | | | | | | | | | | | | | |
|---|---|---|---|---|---|---|---|---|---|---|---|---|---|---|---|
| GGG<br>Gly | TTG<br>Leu<br>105 | TCA<br>Ser | GGC<br>Gly | CTG<br>Leu | GAT<br>Asp | GCT<br>Ala<br>110 | AAG<br>Lys | AGT<br>Ser | GCT<br>Ala | AAG<br>Lys | CGC<br>Arg<br>115 | TTG<br>Leu | GGC<br>Gly | ACG<br>Thr | AGA<br>Arg | 390 |
| GCC<br>Ala<br>120 | ATG<br>Met | GTG<br>Val | TAT<br>Tyr | TAC<br>Tyr | ATG<br>Met<br>125 | TCC<br>Ser | ACC<br>Thr | ACG<br>Thr | ATC<br>Ile | ATT<br>Ile<br>130 | GCT<br>Ala | GCA<br>Ala | GTA<br>Val | CTG<br>Leu | GGG<br>Gly<br>135 | 438 |
| GTC<br>Val | ATT<br>Ile | CTG<br>Leu | GTC<br>Val | TTG<br>Leu<br>140 | GCT<br>Ala | ATC<br>Ile | CAT<br>His | CCA<br>Pro | GGC<br>Gly<br>145 | AAT<br>Asn | CCC<br>Pro | AAG<br>Lys | AAG<br>Lys<br>150 | AAG<br>Lys | | 486 |
| CAG<br>Gln | CTG<br>Leu | GGG<br>Gly | CCT<br>Pro<br>155 | GGG<br>Gly | AAG<br>Lys | GAT<br>Asp<br>160 | GGC<br>Gly | AAT<br>Asn | GTG<br>Val | TCC<br>Ser | CTC<br>Leu<br>165 | CTG<br>Leu | GAT<br>Asp | GCC<br>Ala | | 534 |
| TTC<br>Phe | CTG<br>Leu | GAC<br>Asp<br>170 | GAC<br>Asp | CTG<br>Leu | CGA<br>Arg | AAT<br>Asn | CTC<br>Leu<br>175 | TTC<br>Phe | CCT<br>Pro | GAA<br>Glu | AGC<br>Ser | CTT<br>Leu<br>180 | GTC<br>Val | CAA<br>Gln | GCC<br>Ala | 582 |
| TGT<br>Cys | TTT<br>Phe<br>185 | CAA<br>Gln | CAG<br>Gln | ATT<br>Ile | CAA<br>Gln | ACA<br>Thr<br>190 | GTG<br>Val | AAA<br>Lys | CTG<br>Leu | GTT<br>Val<br>195 | GCA<br>Ala | CCA<br>Pro | CTG<br>Leu | | | 630 |
| CCG<br>Pro<br>200 | CCA<br>Pro | GAC<br>Asp | GAG<br>Glu | GCC<br>Ala<br>205 | AAC<br>Asn | GCA<br>Ala | ACC<br>Thr | AGC<br>Ser | GCT<br>Ala<br>210 | GAA<br>Glu | GTT<br>Val | TCT<br>Ser | CTG<br>Leu | TTG<br>Leu<br>215 | | 678 |

FIG. 3C

| | | | | | | | | | | | | | | | |
|---|---|---|---|---|---|---|---|---|---|---|---|---|---|---|---|
| AAC<br>Asn | GAG<br>Glu | ACT<br>Thr | GTG<br>Val | ACT<br>Thr<br>220 | GAG<br>Glu | GTG<br>Val | CCG<br>Pro | GAG<br>Glu | GAG<br>Glu<br>225 | ACT<br>Thr | AAG<br>Lys | ATG<br>Met | GTT<br>Val | ATC<br>Ile<br>230 | AAG<br>Lys | 726 |
| AAG<br>Lys | GGC<br>Gly | CTG<br>Leu | GAG<br>Glu<br>235 | TTC<br>Phe | AAG<br>Lys | GAT<br>Asp | GGG<br>Gly | ATG<br>Met<br>240 | AAC<br>Asn | GTC<br>Val | TTA<br>Leu | GGT<br>Gly | CTG<br>Leu<br>245 | ATA<br>Ile | GGG<br>Gly | 774 |
| TTT<br>Phe | ATT<br>Ile<br>250 | GCT<br>Ala | TTT<br>Phe | GGC<br>Gly | ATC<br>Ile | GCT<br>Ala<br>255 | CCG<br>Pro | ATG<br>Met | GGG<br>Gly | AAG<br>Lys | ATG<br>Met<br>260 | GAT<br>Asp | CAG<br>Gln | GCC<br>Ala | | 822 |
| AAG<br>Lys | CTG<br>Leu<br>265 | ATG<br>Met | GTG<br>Val | GAT<br>Asp | TTC<br>Phe | TTC<br>Phe<br>270 | AAC<br>Asn | ATT<br>Ile | TTG<br>Leu | AAT<br>Asn | GAG<br>Glu<br>275 | ATT<br>Ile | GTA<br>Val | ATG<br>Met | AAG<br>Lys | 870 |
| TTA<br>Leu<br>280 | GTG<br>Val | ATC<br>Ile | GAT<br>Asp | ATG<br>Met<br>285 | ATC<br>Ile | TGG<br>Trp | TAC<br>Tyr | TCT<br>Ser | CCC<br>Pro | CTG<br>Leu<br>290 | GGT<br>Gly | ATC<br>Ile | GCC<br>Ala | TGC<br>Cys | CTG<br>Leu<br>295 | 918 |
| ATC<br>Ile | TGT<br>Cys | GGA<br>Gly | AAG<br>Lys | ATC<br>Ile<br>300 | ATG<br>Met | ATT<br>Ile | GCA<br>Ala | AAG<br>Lys | GAC<br>Asp<br>305 | TTA<br>Leu | GAA<br>Glu | GTG<br>Val | GTT<br>Val | GCT<br>Ala<br>310 | AGG<br>Arg | 966 |
| CAA<br>Gln | CTG<br>Leu | GGG<br>Gly | ATG<br>Met<br>315 | TAC<br>Tyr | ATG<br>Met | GTA<br>Val | ACA<br>Thr | GTG<br>Val<br>320 | ATA<br>Ile | GGC<br>Gly | CTC<br>Leu | ATC<br>Ile | GTT<br>Val<br>325 | ATC<br>Ile | CAC<br>His | 1014 |

FIG. 3D

```
GGG  GGC  ATC  TTT  CTC  CCC  TTG  ATT  TAC  TTT  GTA  GTG  ACC  AGG  AAA  AAC     1062
Gly  Gly  Ile  Phe  Leu  Pro  Leu  Ile  Tyr  Phe  Val  Val  Thr  Arg  Lys  Asn
          330                           335                      340

CCC  TTC  TCC  CTT  TTT  GCT  GGC  ATT  TTC  CAA  GCT  TGG  ATC  ACT  GCC  CTG     1110
Pro  Phe  Ser  Leu  Phe  Ala  Gly  Ile  Phe  Gln  Ala  Trp  Ile  Thr  Ala  Leu
     345                      350                      355

GGC  ACC  GCT  TCC  AGT  GCT  GGA  ACT  TTG  CCT  GTC  TGG  TTT  TGC  CGT  CTG     1158
Gly  Thr  Ala  Ser  Ser  Ala  Gly  Thr  Leu  Pro  Val  Trp  Phe  Cys  Arg  Leu
360                      365                      370                           375

GAA  AAT  CTG  GGG  ATT  GAT  AAG  CGT  GTG  ACT  TTC  ACC  AGA  CTT  CCT          1206
Glu  Asn  Leu  Gly  Ile  Asp  Lys  Arg  Val  Thr  Phe  Thr  Arg  Leu  Pro
               380                      385                      390

GTT  GGA  GCA  ACC  ATG  AAC  GAT  GGT  AAT  ACA  GCC  GTC  GAT  TTC  TAT          1254
Val  Gly  Ala  Thr  Met  Asn  Asp  Gly  Asn  Thr  Ala  Val  Asp  Phe  Tyr
               395                      400                      405

GCC  GCC  ATC  TTT  ATA  CAA  ATG  ATA  AAT  ATG  GCA  GGT  GTT  CTT  TAT  GAT     1302
Ala  Ala  Ile  Phe  Ile  Gln  Met  Ile  Asn  Met  Ala  Gly  Val  Leu  Tyr  Asp
     410                      415                      420

CAG  GTG  ATT  ACT  AGC  CTC  ACA  GCA  CTG  AGC  GTC  GGA  GGC  GCG            1350
Gln  Val  Ile  Thr  Ser  Leu  Thr  Ala  Leu  Ser  Val  Gly  Gly  Ala
     425                      430                      435
```

FIG. 3E

| | | | | | | | | | | | | | | | | |
|---|---|---|---|---|---|---|---|---|---|---|---|---|---|---|---|---|
| GCC | AGT | ATC | CCC | AGT | GCC | GGG | CTG | GTC | ACC | ATG | CTC | CTC | ATT | CTG | ACA | 1398 |
| Ala | Ser | Ile | Pro | Ser | Ala | Gly | Leu | Val | Thr | Met | Leu | Leu | Ile | Leu | Thr | |
| 440 | | | | 445 | | | | | 450 | | | | | 455 | | |
| GCC | GTG | GGC | CTG | GTG | ACA | GAG | CTG | GAC | ATC | AGC | TTG | CTG | GTG | GCT | GAC | 1446 |
| Ala | Val | Gly | Leu | Val | Thr | Glu | Leu | Asp | Ile | Ser | Leu | Leu | Val | Ala | Asp | |
| | | | | 460 | | | | 465 | | | | 470 | | | | |
| TGG | CTG | GAC | CTG | GAC | ATG | AGG | ATG | AGA | ACT | TCA | GTC | AAT | GTT | GGT | TCT | 1494 |
| Trp | Leu | Asp | Leu | Asp | Met | Arg | Met | Arg | Thr | Ser | Val | Asn | Val | Gly | Ser | |
| | 475 | | | | | | | | 480 | | | | 485 | | | |
| TTT | GGG | GCT | GGG | ATA | GTC | TAT | CAC | CTC | TCC | AAG | TCT | GAG | CTG | GAC | ACC | 1542 |
| Phe | Gly | Ala | Gly | Ile | Val | Tyr | His | Leu | Ser | Lys | Ser | Glu | Leu | Asp | Thr | |
| | 490 | | | | | | 495 | | | | | 500 | | | | |
| ATT | GAC | TCC | GAG | CAT | CGA | GTG | CAT | GAA | GAT | ATT | GAA | ATG | ACC | AAG | ACT | 1590 |
| Ile | Asp | Ser | Glu | His | Arg | Val | His | Glu | Asp | Ile | Glu | Met | Thr | Lys | Thr | |
| | 505 | | | | | 510 | | | | 515 | | | | | | |
| CAA | TCC | ATT | TAT | GAT | GAC | ATG | AAG | CAC | AAC | GAA | AGC | GAA | AAC | TCT | ATT | 1638 |
| Gln | Ser | Ile | Tyr | Asp | Asp | Met | Lys | His | Asn | Glu | Ser | Glu | Asn | Ser | Asn | |
| 520 | | | | | 525 | | | | | 530 | | | | | 535 | |
| CAA | TGT | GTC | TAT | GCT | GCA | CAC | AAC | TCT | GTC | ATA | GTA | GAT | GAA | TGC | AAG | 1686 |
| Gln | Cys | Val | Tyr | Ala | Ala | His | Asn | Ser | Val | Ile | Val | Asp | Glu | Cys | Lys | |
| | | | | 540 | | | | | 545 | | | | | 550 | | |

FIG. 3F

```
GTA ACT CTG GCA GCC AAT GGA AAG TCA GCC GAC TGC AGT GTT GAG GAA
Val Thr Leu Ala Ala Asn Gly Lys Ser Ala Asp Cys Ser Val Glu Glu
        555             560                         565          1734

GAA CCT TGG AAA CGT GAG AAA TAAGGATATG AGTCTCAGCA AATTCTTGAA       1785
Glu Pro Trp Lys Arg Glu Lys
        570

TAAACTCCCC AGCGT                                                   1800
```

FIG. 4A

```
ATAGCGGGA CAGCC

AAG CGC TTC CTG ATG GGG AAA CCG GCG AGG AAA GGA TGC CCG AGT TGG    51
Lys Arg Phe Leu Met Gly Lys Pro Ala Arg Lys Gly Cys Pro Ser Trp
        15          1           5                      10

GTG GTG TCA GGC ATT AAG AAT AAC CCG GCG AGG AAA GGA TGC CCG AGT TGG
```

```
ATAGCGGGA CAGCC

AAG CGC TTC CTG ATG GGG AAA CCG GCG AGG AAA GGA TGC CCG AGT TGG     51
Lys Arg Phe Leu Met Gly Lys Pro Ala Arg Lys Gly Cys Pro Ser Trp
            15      1           5                      10

GTG GTG TTC ACT CTA GAG AAA ATT ACC ATT AAG AAT AAC TGG GTG TTG CTG TCC ACC GTG GTG TGG TCC GCC GCG   99
Val Val Phe Thr Leu Glu Lys Ile Thr Ile Lys Asn Asn Trp Val Leu Leu Ser Thr Val Val Trp Ser Ala Ala
    30              15                                      20                    25

CTC TCA ACT CTA GAG AAA CTC ATC ATT ACC ACA TTC TAC TTT GCA GAA CAC AGC AAC     147
Leu Ser Thr Leu Glu Lys Leu Ile Ile Thr Thr Phe Tyr Phe Ala Glu His Ser Asn
    45                  65  ...
```

| Col1 | Col2 | Col3 | Col4 | Col5 | Col6 | Col7 | Col8 | Col9 | Col10 | Col11 | Col12 | Col13 | Col14 | Col15 | Col16 | Pos |
|---|---|---|---|---|---|---|---|---|---|---|---|---|---|---|---|---|
| ATAGCGGGA | CAGCC | | | | | | | | | | | | | | | |
| AAG Lys | CGC Arg | TTC Phe 15 | CTG Leu | ATG Met 1 | GGG Gly | AAA Lys | CCG Pro | GCG Ala 5 | AGG Arg | AAA Lys | GGA Gly | TGC Cys | CCG Pro 10 | AGT Ser | TGG Trp | 51 |
| GTG Val | GTG Val 30 | TCA Ser | GGC Gly | ATT Ile | AAG Lys | AAT Asn | AAC Asn | CCG Pro | GCG Ala | AGG Arg | AAA Lys | GGA Gly | TGC Cys | CCG Pro | GCG Ala | 99 |

The image shows FIG. 4A, a DNA and protein sequence listing from U.S. Patent 5,776,774 (Jul. 7, 1998, Sheet 17 of 42), presenting codons with their amino acid translations in a tabular layout, with position numbers 51, 99, 147, 195, 243, 291, 339 along the right edge and amino acid residue numbers 1, 5, 10, 15, 20, 25, 30, 35, 40, 45, 50, 55, 60, 65, 70, 75, 80, 85, 90, 95, 100, 105 underneath selected residues.

*FIG. 4B*

```
CTA GGT ATT GTG CTG GTG GTG AGC ATC AAG CCT GGT GTC ACC CAG AAA      387
Leu Gly Ile Val Leu Val Val Ser Ile Lys Pro Gly Val Thr Gln Lys
    110                 115                 120

GTG GGT GAA ATT GCG AGG ACA GGC AGC ACC CCT GAA GTC AGT ACG GTG      435
Val Gly Glu Ile Ala Arg Thr Gly Ser Thr Pro Glu Val Ser Thr Val
125                     130                 135                 140

GAT GCC ATG TTA GAT CTC ATC AGG AAT ATG TTC CCT GAG AAT CTT GTC      483
Asp Ala Met Leu Asp Leu Ile Arg Asn Met Phe Pro Glu Asn Leu Val
                145                     150                     155

CAG GCC TGT TTT CAG CAG TAC AAA ACT AAG CGT GAA GAA GTG AAG CCT      531
Gln Ala Cys Phe Gln Gln Tyr Lys Thr Lys Arg Glu Glu Val Lys Pro
            160                 165                 170

CCC AGC GAT CCA GAG ATG AAC ATG ACA GAA GAG TCC TTC ACA GCT GTC      579
Pro Ser Asp Pro Glu Met Asn Met Thr Glu Glu Ser Phe Thr Ala Val
        175                 180                     185

ATG ACA ACT GCA ATT TCC AAG AAC AAA ACA AAG GAA TAC AAA ATT GTT      627
Met Thr Thr Ala Ile Ser Lys Asn Lys Thr Lys Glu Tyr Lys Ile Val
    190                 195                 200

GGC ATG TAT TCA GAT GGC ATA AAC GTC CTG GGC TTG ATT GTC TTT TGC      675
Gly Met Tyr Ser Asp Gly Ile Asn Val Leu Gly Leu Ile Val Phe Cys
205                 210                 215                     220

CTT GTC TTT GGA CTT GTC ATT GGA AAA ATG GGA GAA AAG GGA CAA ATT      723
Leu Val Phe Gly Leu Val Ile Gly Lys Met Gly Glu Lys Gly Gln Ile
                225                     230                 235
```

FIG. 4C

| CTG Leu | GTG Val | GAT Asp | TTC Phe | TTC Phe 240 | AAT Asn | GCT Ala | TTG Leu | AGT Ser 245 | GAT Asp | GCA Ala | ACC Thr | ATG Met | AAA Lys 250 | ATC Ile | GTT Val | 771 |
| CAG Gln | ATC Ile 255 | ATG Met | TGT Cys | TAT Tyr | ATG Met | GCT Ala | CCA Pro 260 | CTA Leu | GGT Gly | ATT Ile | TTG Leu | TTC Phe 265 | CTG Leu | ATT Ile | GCT Ala | 819 |
| GGG Gly | AAG Lys 270 | ATC Ile | GAA Glu | GTT Val | GAA Glu 275 | ATA Ile | GAC Asp | TGG Trp | TTC Phe | CGC Arg 280 | TTC Phe | AAG Lys | CTG Leu | GGC Gly | | 867 |
| CTT Leu 285 | TAC Tyr | ATG Met | GCC Ala | ACA Thr | GTC Val 290 | CTT Leu | GCA Ala | ATC Ile | CAC His | TCC Ser | ACT Thr | GGG Gly | CTT Leu | GCA Ala 295 | ATT Ile | 915 |
| ATT Ile | CTC Leu | CCG Pro | CTG Leu | ATA Ile 305 | TAT Tyr | TTC Phe | CAG Gln | GCC Ala | ATG Met | AAC Asn | AAG Lys | CGA Arg | ATC Ile | GTA Val 310 | TCC Ser | 963 |
| TTT Phe | GCC Ala | ATG Met | GGA Gly 320 | TAT Tyr | TTC Phe | CAG Gln | GCC Ala | AAC Asn | CCT Pro | ATC Ile | ATG Met 330 | ATG Met | CTC Leu | ACA Thr | TCT Ser | 1011 |
| TCC Ser | AGT Ser 335 | TCA Ser | GCA Ala | ACA Thr | GTC Val 340 | CCT Pro | CTG Leu | ACA Thr | GTC Val | TTC Phe | CGC Arg | TGT Cys | GCT Ala 345 | GAA Glu | AAT Asn | 1059 |

FIG. 4D

| | | | | | | | | | | | | | | | | |
|---|---|---|---|---|---|---|---|---|---|---|---|---|---|---|---|---|
| AAC<br>Asn | CAG<br>Gln<br>350 | GTG<br>Val | GAC<br>Asp | AAG<br>Lys | AGG<br>Arg | ATC<br>Ile<br>355 | ACT<br>Thr | CGA<br>Arg | TTC<br>Phe | CTG<br>Val | TTA<br>Leu<br>360 | CCC<br>Pro | GTT<br>Val | GGT<br>Gly | GCA<br>Ala | 1107 |
| ACA<br>Thr<br>365 | ATC<br>Ile | AAC<br>Asn | ATG<br>Met | GAT<br>Asp | GGG<br>Gly<br>370 | ACC<br>Thr | CTC<br>Leu | TAT<br>Tyr | GAA<br>Glu<br>375 | GCG<br>Ala | GTG<br>Val | GCA<br>Ala | GCG<br>Ala | GTG<br>Val<br>380 | | 1155 |
| TTT<br>Phe | ATT<br>Ile | GCA<br>Ala | CAG<br>Gln | TTG<br>Leu<br>385 | AAT<br>Asn | GAC<br>Asp | CTG<br>Leu | TTC<br>Phe<br>390 | GGC<br>Gly | ATT<br>Ile | GGG<br>Gly | CAG<br>Gln | ATC<br>Ile<br>395 | | | 1203 |
| ACC<br>Thr | ATC<br>Ile | AGT<br>Ser | ACG<br>Thr | GCC<br>Ala | TCT<br>Ser | AGC<br>Ser | GCC<br>Ala<br>405 | GGA<br>Gly | CAG<br>Gln | GCT<br>Ala<br>410 | ATC<br>Ile | | | | | 1251 |
| CCC<br>Pro | GCT<br>Ala<br>415 | GGC<br>Gly | CTG<br>Leu | GAT<br>Asp | ATG<br>Met<br>420 | ACC<br>Thr | GTG<br>Val | CTG<br>Leu | GCC<br>Ala | AGT<br>Ser<br>425 | GGC<br>Gly | | | | | 1299 |
| CTG<br>Leu | GCC<br>Ala | GAG<br>Glu | GAT<br>Asp | GTC<br>Val | ATT<br>Ile | ATT<br>Ile | ACC<br>Thr<br>435 | GCT<br>Ala | GTG<br>Val<br>440 | GAC<br>Asp | TGG<br>Trp | CTC<br>Leu | | | | 1347 |
| GAC<br>Asp<br>445 | AGG<br>Arg | TTC<br>Phe | ATG<br>Met<br>450 | ACC<br>Thr | AAC<br>Asn | GTC<br>Val | CTT<br>Leu | GTC<br>Val | GAT<br>Asp | GCT<br>Ala | GGT<br>Gly<br>455 | GGG<br>Gly | TTT<br>Phe | GCT<br>Ala | ACT<br>Thr<br>460 | 1395 |

FIG. 4E

```
GGC ATT GTG GAA AAG CTC TCC AAG AAG GAG CTG GAG ATG GAT GTT        1443
Gly Ile Val Glu Lys Leu Ser Lys Lys Glu Leu Glu Met Asp Val
                465                 470                 475

TCA TCT GAA GTC AAC ATT GTG AAT CCC TTT GCC TTG GAA TCC ATC        1491
Ser Ser Glu Val Asn Ile Val Asn Pro Phe Ala Leu Glu Ser Ile
            480                 485                 490

CTT GAC AAC GAA GAC TCA GAC ACC AAG AAG TCT TAT GTC AAT GGA GGC    1539
Leu Asp Asn Glu Asp Ser Asp Thr Lys Lys Ser Tyr Val Asn Gly Gly
        495                 500                 505

TTT GCA GTA GAC AAG TCT GAC ATC TCA TTC ACC GAG ACC TCA CAG        1587
Phe Ala Val Asp Lys Ser Asp Ile Ser Phe Thr Glu Thr Ser Gln
510                 515                 520

TTC TAGGGCCCCT GGCTGCAGAG GACTGGAAAC AAGGAAGGAC ATTTCGTGAG        1640
Phe
525

AGTCATCTCA AACACGGCTT AAGGAAAAGA GAAA                             1674
```

FIG. 5A

```
ASCT1        MEKSNETNGLYDSAQAGPAAGPGAPGTAAGRARRCARFLRRQALVLL..TVSGVLAGAGLGAALR.GL
GLAST1  MTKSNGEEPRMGSRMTRFQQGVRKRTLLAKKKVQNITKEDVKSYLFRNAFVLL..TVSAVIGTILGFALRPY.
GLT1           MASTEGANNMPKQVEVRMHDSHLSSEEPKHRNLGMRMCDKLGKNLLLSLTVFGVILGAVCGGLLRLAA
EAAC1                                          MGKPARKGCDSKRFLKNNWLLLS.TVVAVVLGIVIGIVLVREYS

66      SLSRTQVTYLAFPGEMLLRMLRVIILPLVVCSLVSQAASLDASCLQRLGGIRVAYFGL.TTLSASALAVALAFI
 72      KMSYREVKYFSFPGELLMRMLQVLVLPLIISSLVTGMAALDSKASGKMGM.RAVVYYMTTIIAVVIGIIIVII
 69      PIHPDVVMLIAFPGDILMRMLKVLILEPLIISSLITGLSGLDAKASGRLGT.RAMVYYMSTTIIAAVLGVILLA
 43      NLSTLDKFYFAFPGEILMRMLKLVILPLIVSSMITGVAALDSNVSGKIGL.RAVLYFCTTIIAVILGIVLVVS

130     IKPGSGAQTLQSSDLGLEDSGPPPVPKETVDSFLDLARNLFPSNLVAAFRTYATDYKVV........TONSSS
145     IHPGKGT.KENMYREGKIVOVTA......ADAFLDLIRNMFPPNLVEACFKQFKTSYEKRSFKVPIQANETLLG
142     IHPGNPKLKKQLGPGKKNDEVSS......LDAFLDLIRNLFPENLVQACFEQQIQTVTKKVLVAPPS.EEANTTK
116     IKPGVTQKVDEIDRTGSTPEVST......VDAMLDLIRNMFPENLVQACFQQYKTTREEV..TASDDTGKNGTE

205     QNVTHEKIPIGTEI.............EGMNILGLVLFALVLGVALKKLGSEGEDLIRFFNSLNEATVLVSW
212     AVINVSEAMETLTRIREEMVPVPGSVN.GVNALGLVVFSMCFGFVIGNMKEQGGALREFFDSLNEAIVRLVAV
209     AVISLINETMNEAPEETKIVIKKGLEFKDGMNVLGLIGFFIAFGIAMGKMGVAGGADGGVLOMSERDCHEVSDM
182     ESVTAVMTTAVSENRIKEYRVVGLYS..DGINVLGLIVFCLVFGLVIGKMGEKGGILVDFFNALSDATVKIVQI

265     IMWYVPVGIMFLVGSRIVEMKDIIVLVTSLGKYIFASILGHVIHGGIVLPLIYFVFTRKNPFRFLLGLLAPFAT
285     IMWYAPLGILFLIAGKILEMEDMGVIGGOLAMYTVTIVGLLIHAVILPLIYELPLIYFVVTRKNPWVFIGGLLQALIT
283     DHVFPAGIACLICGKIIAIKDLEVAROLGMITVIVGLIIHGGIFLPLPLIYFVVTRKNPFSFFAGIFOAWIT
254     IMCYMPLGILFLIAGKIIEVEDWEIF.RKLGLYMVTVLSGLAIHSIVILPLIYFIVRKNPFRFAMGMTQALLT

339     AFATCSSSATLPSMMKCIEENNGVDKRISREILPIGATVNMDGAAIFQCVAAVFIAGLNNIEINAGQIFGILVT
350     ALGTSSSSATLPITFKCLEENNGVDKRITRFVLPVGATINMDGTALYEALAAIFIAGVNNEDINFGQIITISIT
357     ALGTASSAGTLPVTFRCLEDNLGIDKRVTRFVLPVGATINMDGTALYEAVAAIFIAGMNGVIIDGGQIVTVSLI
327     ALMISSSSATLPVTFRCAEEKNRVDKRITRFVLPVGATINMDGTALYEAVAAVFIAGLNDMDLSIGQIITISVT
```

FIG. 5B

```
413  ATASSVGAAGVPAGGVLTIAILEAIGLPTHDLPLILAVDWIVDRTTTVNVEGDALGAGILHMLNQKATKKGE
433  ATAASIGAAGIPQAGIPOAGLVTMVIVLTSVGLPTDDITLIIAVDWFLDRLRTTNVLGDSLGAGIVERHLSRHELKNRD
431  ATLASIGAASIPSAGLVTMLLILTAVGLPTEDISLLVAVDWLLDRMRTSVNVVGDSFGAGIYYHLSKSELDTID
401  ATAASIGAAGVPOAGLVTMVIVLSAVGLFAEDVTLLIAVDWLLDRFRTVVNVLGDAFGTGIVEKISKKELEQMD

487  QELAEVKVEAIPNCKSEEETSPLVTHQNPAGPVASAPELESKESVL  532
507  VEMGNSVIEENEMKKPYQLIAQDNEPEKPVADSETKM  543
505  SQHRMHEDIEMTKTQSVYDDTKNHRESNSNQCVYAAHNSVVIDECKVTLAANGKSADCSVEEEPWKREK  573
475  VSSEVNIVNPFALESATLDNEDSDTKKSYINGGFAVDKSDTISFTQTSQF  524
```

FIG. 11

```
EAAT1        MTKSNGEEPKMGGRMERFQQGVRKRTLLAKKVQNTKKOVKSYLFGNPFVLL..TVTAVIVGI.IGFILRPY.
EAAT2                           MASTEGANNMPKQVEVRMPDSHLGSEEPKHRMLGLRLCDKLGKNLLILTLTVFGVIGAVCGGLLRLAS
EAAT3                                                   MGKPARKGCPSWKRFLKNNWVLLIS.IVAAVLGITTGVLVREHS
                                                                                    ─── 1 ───

72          RMSYREVKYFSFPGELIMRFQMLVIPLIISSLVIGMAALDSKASGKMGMRAVVYYMTTTIAVVIGIIIVII
 69          PIMPDVVMLIAFEGDIIMRMKIMIIPLPLIISSLITGSLDAKASGRLGTRAMVYMSTTIAAVLGVIILVLAI
 44          NLSTLEKFYFAFPGELLMRMLKLIILPLIISSMITGVAALDSNSGKIGLRAVVYYFGTTLIAVIIGIVVSI
                            ─── 2 ───                              ─── 3 ───

146          HPGKGT KENMHREGKIVRTAADAFLDLIRNMFPNLVEACFKQFKTGYEKRSFKVPIQANBTLVGAVINNS
143          HPGNPKLRKQLGPGKKNDEVSSLDRFLDLIRNLFPENLVQACFQQIQTVTKKVLVAPPPDEEANATSAEVSLIN
118          KPGVTQKVGEIARTGSTPEVSTVDAMDLIRNMFPENLVQACFQQVRTKRFEV..KPPSDPFNMTEESFTAVM
                                                                                    ─── 5 ───

219          EAMETLTRITFELVPGSVN.GVNALGIVYFSMCFGFVIGNMKEQGQAIREFFDSINEAIMRLVAVIMIIAFE
217          ETVTEVPEETKMVIKKGLEFKDGMNVLGLIGFFIAFGIAMGRMSDQAKLMVDFFNILNEIVMKIVIMIMISPE
190          TTAISKNKTKFYKIVGMYS..DGINVLGLIVFCLVFGLVIGKMGEKGQIIVDFFNAISDATMKIVQIIMCVMPL
                        ─── 4 ───

292          GIFLIAGKIVEMEDMGVIGGQLAMYTYTVIVGLIIHAVITLPLLYELVTRKNPWVEIGGLLOALLIALGISSS
291          GIACLICGKIIAIKDLEVVARQLGMMYTVIIGLIIHGGIFLPLIYFVVTRKNPESLFAGIFQAWITALGIASS
261          GIFLIAGKIIEVEDWFIF.RKIGLYMATVLTGLAIHSIVILPLIYFIVVRKNPFRFAMGQALLTALMISSS
                                                                    ─── 6 ───

366          SATLPITFKCLEENNGVDKRYTRFVLPVGATINMDGTALYEALAAIEIAQVNEEINFGQLLLSITATASIG
385          AGTLPITEKCLEENLGIDKRVTRFVLPVGATINMDGTALYEAVAAIEIAQMNGVVIDGQIVTVSLIATLASVG
334          SATLPITFKCAEENNQVDKRITRFVLPVGATINMDGTALYEAVAAVFIAQLNDLDLGIGQITTISITATSASIG
                                                    ─── 8 ───
```

FIG. 11A

```
        ┌─9
440  AAGIPQAGLYTMVIVLTSVGIPTDDITLILAVDMFLDRLRTTNVLGDSLGAGIVEHLSRHEIKNRDVEMGNSV
439  AASIPSAGIVTMLLITAVGIPTEDLSLLVAVDMFLDRMRISYNVVGDSTGAGTYFDSKSELDTIDSQMRVHE
408  AAGVFQRGEVTHVIVLSAVGLPAEDVTLILAVDMTLDRFRTMVNVLGDAFGTGIVEKLISMKIIEQMDSVSSEVNI

514  IEENEMKKPYQLIAQDNETEKPIDSETKM 542
513  DIEMTKTQSIYDDMKNHRESNSNQCVYAAHNSVIVDECKVTLAANGKSADCSVEEEPWKREK 574
482  VNPFALESTILDNEDSDTKKSYVNGGFAVDKSDTISFTQTSQF 525
```

AMINO ACID TRANSPORTERS AND USES

This is a divisional of application Ser. No. 08/140,729, filed Oct. 20, 1993.

This invention was made with government support under National Institute of Health grants DA07595 and DA03160. The government has certain rights to this invention.

BACKGROUND OF THE INVENTION

1. Field of the Invention

This invention relates to amino acid transporters from mammalian species and the genes corresponding to such transporters. Specifically, the invention relates to the isolation, cloning and sequencing of complementary DNA (cDNA) copies of messenger RNA (mRNA) encoding each of four novel human amino acid transporter genes. The invention also relates to the construction of recombinant expression constructs comprising such cDNAs from each of the four novel human amino acid transporter genes of the invention, said recombinant expression constructs being capable of expressing amino acid transporter proteins in cultures of transformed prokaryotic and eukaryotic cells. Production of the transporter proteins in such cultures is also provided. The invention relates to the use of such cultures of such transformed cells to produce homogeneous compositions of each transporter protein. The invention also provides cultures of such cells producing transporter proteins for the characterization of novel and useful drugs. Antibodies against and epitopes of these transporter proteins are also provided by the invention.

2. Background of the Invention

The approximately 20 naturally-occurring amino acids are the basic building blocks for protein biosynthesis. Certain amino acids, such as glutamate and glycine, as well as amino acid derivatives such as γ-aminobutyric acid (GABA), epinephrine and norepinephrine, and histamine, are also used as signaling molecules in higher organisms such as man. For these reasons, specialized trans-membrane transporter proteins have evolved in all organisms to recover or scavenge extracellular amino acids (see Christensen, 1990, Physiol. Rev. 70: 43–77 for review).

These transporter proteins play a particularly important role in uptake of extracellular amino acids in the vertebrate brain (see Nicholls & Attwell, 1990, TiPS 11: 462–468). Amino acids that function as neurotransmitters must be scavenged from the synaptic cleft between neurons to enable continuous repetitive synaptic transmission. More importantly, it has been found that high extracellular concentrations of certain amino acids (including glutamate and cysteine) can cause neuronal cell death. High extracellular amino acid concentrations are associated with a number of pathological conditions, including ischemia, anoxia and hypoglycemia, as well as chronic illnesses such as Huntington's disease, Parkinson's disease, Alzheimer's disease, epilepsy and amyotrophic lateral sclerosis (ALS; see Pines et al., 1992, Nature 30: 464–467).

Glutamate is one example of such an amino acid. Glutamate is an excitatory neurotransmitter (i.e., excitatory neurons use glutamate as a neurotransmitter). When present in excess (>about 300 µM; Bouvier et al., 1992, Nature 36: 471–474; Nicholls & Attwell, ibid.; >5 µM for 5 min.; Choi et al., 1987, J. Neurosci. 7: 357–358), extracellular glutamate causes neuronal cell death. Glutamate transporters play a pivotal role in maintaining non-toxic extracellular concentrations of glutamate in the brain. During anoxic conditions (such as occur during ischemia), the amount of extracellular glutamate in the brain rises dramatically. This is in part due to the fact that, under anoxic conditions, glutamate transporters work in reverse, thereby increasing rather than decreasing the amount of extracellular glutamate found in the brain. The resultingly high extracellular concentration of glutamate causes neuron death, with extremely deleterious consequences for motor and other brain functions, resulting in stroke, anoxia and other instances of organic brain dysfunction.

This important role for amino acid transporters in maintaining brain homeostasis of extracellular amino acid concentrations has provided the impetus for the search for and development of compounds to modulate and control transporter function. However, conventional screening methods require the use of animal brain slices in binding assays as a first step. This is suboptimal for a number of reasons, including interference in the binding assay by non-specific binding of heterologous (i.e., non-transporter) cell surface proteins expressed by brain cells in such slices; differential binding by cells other than neuronal cells present in the brain slice, such as glial cells or blood cells; and the possibility that putative drug binding behavior in animal brain cells will differ from the binding behavior in human brain cells in subtle but critical ways. The ability to synthesize human transporter molecules in vitro would provide an efficient and economical means for rational drug design and rapid screening of potentially useful compounds.

Amino acid transporters are known in the art, and some of these proteins have been isolated biochemically and their corresponding genes have been recently cloned using genetic engineering means.

Christensen et al., 1967, J. Biol. Chem. 242: 5237–5246 report the discovery of a neutral amino acid transporter (termed the ACS transporter) in Erlich ascites tumor cells.

Makowske & Christensen, 1982, J. Biol. Chem. 257: 14635–14638 provide a biochemical characterization of hepatic amino acid transport. Kanner & Schuldiner, 1987, CRC Crit. Rev. Biochem. 22: 1–38 provide a review of the biochemistry of neurotransmitters.

Olney et al., 1990, Science 248: 596–599 disclose that the amino acid cysteine is a neurotoxin when present in excess extracellularly.

Wallace et al., 1990, J. Bacteriol. 172: 3214–3220 report the cloning and sequencing of a glutamate/aspartate transporter gene termed gltP from *Escherichia coli* strain K12.

Kim et al., 1991, Nature 352: 725–728 report the discovery that a cationic amino acid transporter is the cell surface target for infection by ecotropic retroviruses in mice.

Wang et al., 1991, Nature 3: 729–731 report the discovery that a cationic amino acid transporter is the cell surface target for infection by ecotropic retroviruses in mice.

Maenz et al., 1992, J. Biol. Chem. 267: 1510–1516 provide a biochemical characterization of amino acid transport in rabbit jejunal brush border membranes.

Bussolati et al., 1992, J. Biol. Chem. 267: 8330–8335 report that the ASC transporter acts in an electrochemically neutral manner so that sodium ion co-transport occurs without disrupting the normal membrane potential of the cells expressing the transporter.

Engelke et al., 1992, J. Bacteriol. 171: 5551–5560 report the cloning of a dicarboxylate carrier from *Rhizobium meliloti*.

Guastella et al., 1992, Proc. Natl. Acad. Sci. USA 89: 7189–7193 disclose the cloning of a sodium ion and chloride ion-dependent glycine transporter from a glioma cell line that is expressed in the rat forebrain and cerebellum.

Kavanaugh et al., 1992, J. Biol. Chem. 267:22007–22009 report that biochemical characterization of a rat brain GABA transporter expressed in vitro in *Xenopus laevis* oocytes.

Storck et al., 1992, Proc. Natl. Acad. Sci. USA 89: 10955–10959 disclose the cloning and sequencing of a sodium ion-dependent glutamate/aspartate transporter from rat brain termed GLAST1.

Bouvier et al., ibid., disclose the biochemical characterization of a glial cell-derived glutamate transporter.

Pines et al., ibid., report the cloning and sequencing of a glial cell glutamate transporter from rat brain termed GLT-1.

Kanai & Hediger, 1992, Nature 360: 467–471 disclose the cloning and sequencing of a sodium ion-dependent, high affinity glutamate transporter from rabbit small intestine termed EAAC1.

Kong et al., 1993, J. Biol. Chem. 268: 1509–1512 report the cloning and sequencing of a sodium-ion dependent neutral amino acid transporter of the A type that is homologous to a sodium-ion dependent glucose transporter.

Nicholls & Attwell, ibid., review the role of amino acids and amino acid transporters in normal and pathological brain functions.

SUMMARY OF THE INVENTION

The present invention relates to the cloning, expression and functional characterization of mammalian amino acid transporter genes. The invention comprises nucleic acids, each nucleic acid having a nucleotide sequence of a novel amino acid transporter gene. The nucleic acids provided by the invention each comprise a complementary DNA (cDNA) copy of the corresponding mRNA transcribed in vivo from each of the amino acid transporter genes of the invention. Also provided are the deduced amino acid sequences of each the cognate proteins of the cDNAs provided by the invention.

This invention provides nucleic acids, nucleic acid hybridization probes, recombinant eukaryotic expression constructs capable of expressing the amino acid transporters of the invention in cultures of transformed cells, such cultures of transformed eukaryotic cells that synthesize the amino acid transporters of the invention, homogeneous compositions of each of the amino acid transporter proteins, and antibodies against and epitopes of each of the amino acid transporter proteins of the invention. Methods for characterizing these transporter proteins and methods for using these proteins in the development of agents having pharmacological uses related to these transporter proteins are also provided by the invention.

In a first aspect, the invention provides a nucleic acid having a nucleotide sequence encoding a human neutral amino acid transporter that is the ASCT1 transporter (SEQ ID No:2). In this embodiment of the invention, the nucleotide sequence includes 1680 nucleotides of the human ASCT1 cDNA comprising 1596 nucleotides of coding sequence, 30 nucleotides of 5' untranslated sequence and 54 nucleotides of 3' untranslated sequence. In this embodiment of the invention, the nucleotide sequence of the ASCT1 transporter consists essentially of the nucleotide sequence depicted in FIG. 1 (SEQ ID No:2). The use of the term "consisting essentially of" herein is meant to encompass the disclosed sequence and includes allelic variations of this nucleotide sequence, either naturally occurring or the product of in vitro chemical or genetic modification. Each such variant will be understood to have essentially the same nucleotide sequence as the nucleotide sequence of the corresponding ASCT1 disclosed herein.

The corresponding ASCT1 protein molecule, having the deduced amino acid sequence consisting essentially of the sequence shown in FIG. 1 (SEQ ID No.:3), is also claimed as an aspect of the invention. The use of the term "consisting essentially of" herein is as described above. Similarly, the corresponding ASCT1 protein molecule, having the deduced amino acid sequence consisting essentially of the sequence shown in FIG. 1 (SEQ ID No.:3), is also claimed as an aspect of the invention. ASCT1 protein molecules provided by the invention are understood to have substantially the same biological properties as the ASCT1 protein molecule encoded by the nucleotide sequence described herein.

In another aspect, the invention comprises a homogeneous composition of the 55.9 kD mammalian ASCT1 transporter or derivative thereof, said size being understood to be the size of the protein before any post-translational modifications thereof. The amino acid sequence of the ASCT1 transporter or derivative thereof preferably consists essentially of the amino acid sequence of the human ASCT1 transporter protein shown in FIG. 1 (SEQ ID No:3).

In a second aspect, the invention provides a nucleic acid having a nucleotide sequence encoding a human excitatory amino acid transporter that is the EAAT1 transporter (SEQ ID No:4). In this embodiment of the invention, the nucleotide sequence includes 1680 nucleotides of the human EAAT1 cDNA comprising 1626 nucleotides of coding sequence, 30 nucleotides of 5' untranslated sequence and 24 nucleotides of 3' untranslated sequence. In this embodiment of the invention, the nucleotide sequence of the EAAT1 transporter consists essentially of the nucleotide sequence depicted in FIG. 2 (SEQ ID No:4). The use of the term "consisting essentially of" herein is as described above.

In another aspect, the invention comprises a homogeneous composition of the 59.5 kilodalton (kD) mammalian EAAT1 transporter or derivative thereof, said size being understood to be the size of the protein before any post-translational modifications thereof. The amino acid sequence of the EAAT1 transporter or derivative thereof preferably consists essentially of the amino acid sequence of the human EAAT1 transporter protein shown in FIG. 2 (SEQ ID No:5). EAAT1 protein molecules provided by the invention are understood to have substantially the same biological properties as the EAAT1 protein molecule encoded by the nucleotide sequence described herein.

In a third aspect, the invention provides a nucleic acid having a nucleotide sequence encoding a human excitatory amino acid transporter that is the EAAT2 transporter (SEQ ID No:6). In this embodiment of the invention, the nucleotide sequence includes 1800 nucleotides of the human EAAT2 cDNA comprising 1722 nucleotides of coding sequence, 33 nucleotides of 5' untranslated sequence and 45 nucleotides of 3' untranslated sequence. In this embodiment of the invention, the nucleotide sequence of the EAAT2 transporter consists essentially of the nucleotide sequence depicted in FIG. 3 (SEQ ID No:6). The use of the term "consisting essentially of" herein is as described above.

The corresponding EAAT2 protein molecule, having the deduced amino acid sequence consisting essentially of the sequence shown in FIG. 3 (SEQ ID No.:7), is also claimed as an aspect of the invention. EAAT2 protein molecules provided by the invention are understood to have substantially the same biological properties as the EAAT2 protein molecule encoded by the nucleotide sequence described herein.

In another aspect, the invention comprises a homogeneous composition of the 62.1 kD mammalian EAAT2 transporter or derivative thereof, said size being understood to be the size of the protein before any post-translational modifications thereof. The amino acid sequence of the EAAT2 transporter or derivative thereof preferably consists essentially of the amino acid sequence of the human EAAT2 transporter protein shown in FIG. 3 (SEQ ID No:7).

In yet another aspect, the invention provides a nucleic acid having a nucleotide sequence encoding a human excitatory amino acid transporter that is the EAAT3 transporter (SEQ ID No:8). In this embodiment of the invention, the nucleotide sequence includes 1674 nucleotides of the human EAAT3 cDNA comprising 1575 nucleotides of coding sequence, 15 nucleotides of 5' untranslated sequence and 84 nucleotides of 3' untranslated sequence. In this embodiment of the invention, the nucleotide sequence of the EAAT3 transporter consists essentially of the nucleotide sequence depicted in FIG. 4 (SEQ ID No:8). The use of the term "consisting essentially of" herein is as described above.

The corresponding EAAT3 protein molecule, having the deduced amino acid sequence consisting essentially of the sequence shown in FIG. 4 (SEQ ID No.:9), is also claimed as an aspect of the invention. EAAT3 protein molecules provided by the invention are understood to have substantially the same biological properties as the EAAT3 protein molecule encoded by the nucleotide sequence described herein.

In another aspect, the invention comprises a homogeneous composition of the 57.2 kD mammalian EAAT3 transporter or derivative thereof, said size being understood to be the size of the protein before any post-translational modifications thereof. The amino acid sequence of the EAAT3 transporter or derivative thereof preferably consists essentially of the amino acid sequence of the human EAAT3 transporter protein shown in FIG. 4 (SEQ ID No:9).

This invention provides both nucleotide and amino acid probes derived from the sequences herein provided. The invention includes probes isolated from either cDNA or genomic DNA, as well as probes made synthetically with the sequence information derived therefrom. The invention specifically includes but is not limited to oligonucleotide, nick-translated, random primed, or in vitro amplified probes made using CDNA or genomic clone embodying the invention, and oligonucleotide and other synthetic probes synthesized chemically using the nucleotide sequence information of cDNA or genomic clone embodiments of the invention.

It is a further object of this invention to provide such nucleic acid hybridization probes to determine the pattern, amount and extent of expression of these transporter genes in various tissues of mammals, including humans. It is also an object of the present invention to provide nucleic acid hybridization probes derived from the sequences of the amino acid transporter genes of the invention to be used for the detection and diagnosis of genetic diseases. It is an object of this invention to provide nucleic acid hybridization probes derived from the DNA sequences of the amino acid transporter genes herein disclosed to be used for the detection of novel related receptor genes.

The present invention also includes synthetic peptides made using the nucleotide sequence information comprising the cDNA embodiments of the invention. The invention includes either naturally occurring or synthetic peptides which may be used as antigens for the production of amino acid transporter-specific antibodies, or used for competitors of amino acid transporter molecules for amino acid, agonist, antagonist or drug binding, or to be used for the production of inhibitors of the binding of agonists or antagonists or analogues thereof to such amino acid transporter molecules.

The present invention also provides antibodies against and epitopes of the mammalian amino acid transporter molecules of the invention. It is an object of the present invention to provide antibodies that are immunologically reactive to the amino acid transporters of the invention. It is a particular object to provide monoclonal antibodies against these amino acid transporters, must preferably the human excitatory and neutral amino acid transporters as herein disclosed. Hybridoma cell lines producing such antibodies are also objects of the invention. It is envisioned at such hybridoma cell lines may be produced as the result of fusion between a non-immunoglobulin producing mouse myeloma cell line and spleen cells derived from a mouse immunized with a cell line which expresses antigens or epitopes of an amino acid transporter of the invention. The present invention also provides hybridoma cell lines that produces such antibodies, and can be injected into a living mouse to provide an ascites fluid from the mouse that is comprised of such antibodies. It is a further object of the invention to provide immunologically-active epitopes of the amino acid transporters of the invention. Chimeric antibodies immunologically reactive against the amino acid transporter proteins of the invention are also within the scope of this invention.

The present invention provides recombinant expression constructs comprising a nucleic acid encoding an amino acid transporter of the invention wherein the construct is capable of expressing the encoded amino acid transporter in cultures of cells transformed with the construct. Preferred embodiments of such constructs comprise the human EAAT1 cDNA (SEQ ID No.:4), the human EAAT2 cDNA (SEQ ID No.:6), the human EAAT3 cDNA (SEQ ID No.:8), and human ASCT1 cDNA (SEQ ID No.:2), each construct being capable of expressing the amino acid transporter encoded therein in cells transformed with the construct.

The invention also provides cultures cells transformed with the recombinant expression constricts of the invention, each such cultures being capable of and in fact expressing the amino acid transporter encoded in the transforming construct.

The present invention also includes within its scope protein preparations of prokaryotic and eukaryotic cell membranes containing at least one of the amino acid transporter proteins of the invention, derived from cultures of prokaryotic or eukaryotic cells, respectively, transformed with the recombinant expression constructs of the invention. In a preferred embodiment, each preparation of such cell membranes comprises one species of the amino acid transporter proteins of the invention.

The invention also provides methods for screening compounds for their ability to inhibit, facilitate or modulate the biochemical activity of the amino acid transporter molecules of the invention, for use in the in vitro screening of novel agonist and antagonist compounds. In preferred embodiments, cells transformed with a recombinant expression construct of the invention are contacted with such a compound, and the effect of the compound on the transport of the appropriate amino acid is assayed. Additional preferred embodiments comprise quantitative analyses of such effects.

The present invention is also useful for the detection of analogues, agonists or antagonists, known or unknown, of the amino acid transporters of the invention, either naturally occurring or embodied as a drug. In preferred embodiments, such analogues, agonists or antagonists may be detected in blood, saliva, semen, cerebrospinal fluid, plasma, lymph, or any other bodily fluid.

Specific preferred embodiments of the present invention will become evident from the following more detailed description of certain preferred embodiments and the claims.

DESCRIPTION OF THE DRAWINGS

FIGS. 1A through 1E illustrates the nucleotide (SEQ ID No.:2) and amino acid (SEQ ID No.:3) sequences of the human ASCT1 neutral amino acid transporter.

FIGS. 2A through 2E illustrates the nucleotide (SEQ ID No.:4) and amino acid (SEQ ID No.:5) sequences of the human EAAT1 excitatory amino acid transporter.

FIGS. 3A through 3F illustrates the nucleotide (SEQ ID No.:6) and amino acid (SEQ ID No.:7) sequences of the human EAAT2 excitatory amino acid transporter.

FIGS. 4A through 4E illustrates the nucleotide (SEQ ID No.:8) and amino acid (SEQ ID No.:9) sequences of the human EAAT3 excitatory amino acid transporter.

FIGS. 5A and 5B presents an amino acid sequence comparison between human ASCT1, GLAST1, GLT1 and EAAC1.

FIGS. 11 and 11A illustrates the degree of predicted amino acid sequence homology between the novel human glutamate transporters EAAT1, EAAT2 and EAAT3; overbars indicate nine regions of hydrophobicity determined using the algorithm of Eisenberg et al., and potential sites of N-linked glycosylation are shown by the circled asparagine (N) residues.

DETAILED DESCRIPTION OF THE PREFERRED EMBODIMENTS

Figure 6A:
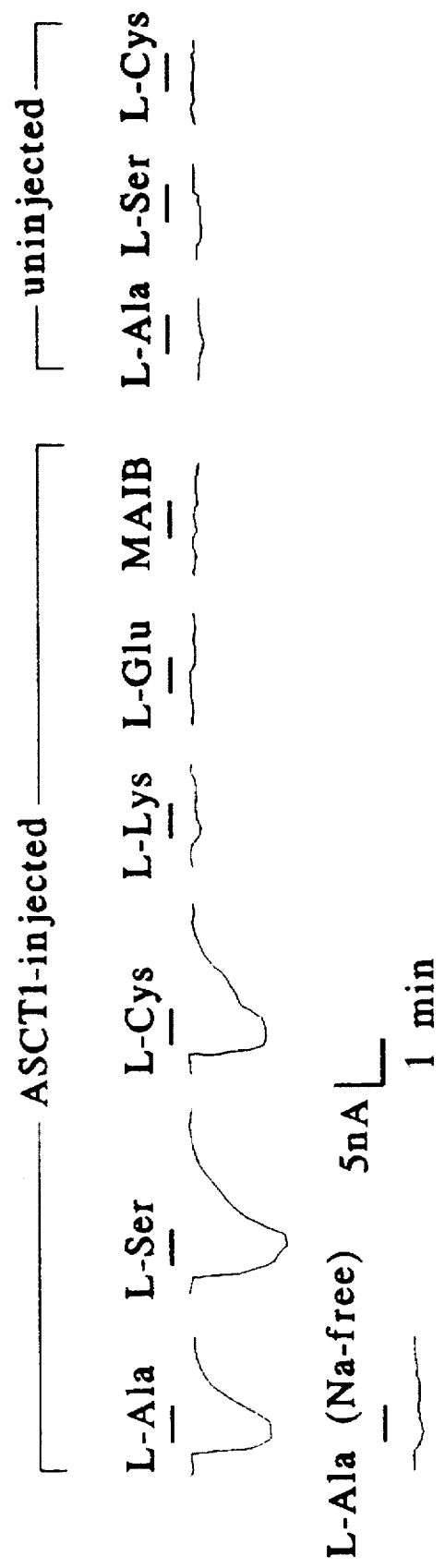
FIGS. 6A through 6C illustrates transmembrane electrochemical currents in $Xenopus\ laevis$ oocytes microinjected with RNA encoding ASCT1 and contacted with the indicated amino acids (FIG. 6A); the amino acid concentration dependence of such electrochemical currents (FIG. 6B); and a plot of normalized current vs. amino acid concentration illustrating the kinetic parameters of amino acid transport (FIG. 6C).

The term "human amino acid transporter EAAT1" as used herein refers to proteins consisting essentially of, and having substantially the same biological activity as, the protein encoded by the nucleic acid depicted in FIGS. 2A through 2B (SEQ ID No.:4). This definition is intended to encompass natural allelic variations in the EAAT1 sequence. Cloned nucleic acid provided by the present invention may encode EAAT1 protein of any species of origin, including, for example, mouse, rat, rabbit, cat, and human, but preferably the nucleic acid provided by the invention encodes EAAT1 receptors of mammalian, most preferably human, origin.

The term "human amino acid transporter EAAT2" as used herein refers to proteins consisting essentially of, and having substantially the same biological activity as, the protein encoded by the nucleic acid depicted in FIGS. 3A through 3F (SEQ ID No.:6). This definition is intended to encompass natural allelic variations in the EAAT2 sequence. Cloned nucleic acid provided by the present invention may encode EAAT2 protein of any species of origin, including, for example, mouse, rat, rabbit, cat, and human, but preferably the nucleic acid provided by the invention encodes EAAT2 receptors of mammalian, most preferably human, origin.

The term "human amino acid transporter EAAT3" as used herein refers to proteins consisting essentially of, and having substantially the same biological activity as, the protein encoded by the nucleic acid depicted in FIGS. 4A through 4E (SEQ ID No.:8). This definition is intended to encompass natural allelic variations in the EAAT3 sequence. Cloned nucleic acid provided by the present invention may encode EAAT3 protein of any species of origin, including, for example, mouse, rat, rabbit, cat, and human, but preferably the nucleic acid provided by the invention encodes EAAT3 receptors of mammalian, most preferably human, origin.

The term "human amino acid transporter ASCT1" as used herein refers to proteins consisting essentially of, and having substantially the same biological activity as, the protein encoded by the nucleic acid depicted in FIGS. 1A through 1E (SEQ ID No.:2). This definition is intended to encompass natural allelic variations in the ASCT1 sequence. Cloned nucleic acid provided by the present invention may encode ASCT1 protein of any species of origin, including, for example, mouse, rat, rabbit, cat, and human, but preferably the nucleic acid provided by the invention encodes ASCT1 receptors of mammalian, most preferably human, origin.

Each of the nucleic acid hybridization probes provided by the invention comprise DNA or RNA consisting essentially of the nucleotide sequence of one of the amino acid transporters, depicted in FIGS. 1A through 1E, FIGS. 2A through 2E, FIGS. 3A through 3F and FIGS. 4A through 4E (SEQ ID Nos.:2,4,6,8), or any portion thereof effective in nucleic acid hybridization. Mixtures of such nucleic acid hybridization probes are also within the scope of this embodiment of the invention. Nucleic acid probes as provided herein are useful for detecting amino acid transporter gene expression in cells and tissues using techniques well-known in the art, including but not limited to Northern blot hybridization, in situ hybridization and Southern hybridization to reverse transcriptase—polymerase chain reaction product DNAs. The probes provided by the present invention, including oligonucleotides probes derived therefrom, are useful are also useful for Southern hybridization of mammalian, preferably human, genomic DNA for screening for restriction fragment length polymorphism (RFLP) associated with certain genetic disorders.

The production of proteins such as these amino acid transporter molecules from cloned genes by genetic engineering means is well known in this art. The discussion which follows is accordingly intended as an overview of this field, and is not intended to reflect the full state of the art.

DNA encoding an amino acid transporter may be obtained, in view of the instant disclosure, by chemical synthesis, by screening reverse transcripts of mRNA from appropriate cells or cell line cultures, by screening genomic libraries from appropriate cells, or by combinations of these procedures, as illustrated below. Screening of mRNA or genomic DNA may be carried out with oligonucleotide probes generated from the nucleic acid sequence information from each of the amino acid transporters disclosed herein. Probes may be labeled with a detectable group such as a fluorescent group, a radioactive atom or a chemiluminescent group in accordance with know procedures and used in conventional hybridization assays, as described in greater detail in the Examples below. In the alternative, amino acid transporter-derived nucleic acid sequences may be obtained by use of the polymerase chain reaction (PCR) procedure, using PCR oligonucleotide primers corresponding to nucleic acid sequence information derived from an amino acid transporter as provided herein. See U.S. Pat. Nos. 4,683,195 to Mullis et al. and 4,683,202 to Mullis.

Each of the amino acid transporter proteins may be synthesized in host cells transformed with a recombinant expression construct comprising a nucleic acid encoding the particular amino acid transporter cDNA. Such recombinant expression constructs can also be comprised of a vector that is a replicable DNA construct. Vectors are used herein either to amplify DNA encoding an amino acid transporter and/or to express DNA encoding an amino acid transporter gene. For the purposes of this invention, a recombinant expression construct is a replicable DNA construct in which a nucleic acid encoding an amino acid transporter is operably linked to suitable control sequences capable of effecting the expression of the amino acid transporter in a suitable host.

The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants. See, Sambrook et al., 1990, *Molecular Cloning: A Laboratory Manual* (Cold Spring Harbor Press: New York).

Vectors useful for practicing the present invention include plasmids, viruses (including phage), retroviruses, and integratable DNA fragments (i.e., fragments integratable into the host genome by homologous recombination). The vector replicates and functions independently of the host genome, or may, in some instances, integrate into the genome itself. Suitable vectors will contain replicon and control sequences which are derived from species compatible with the intended expression host. A preferred vector is pCMV5 (Andersson et al., 1989, *J. Biol. Chem.* 264: 8222–8229). Transformed host cells are cells which have been transformed or transfected with recombinant expression constructs made using recombinant DNA techniques and comprising nucleic acid encoding an amino acid transporter protein. Preferred host cells are COS-7 cells (Gluzman, 1981, Cell 23: 175–182). Transformed host cells may express the amino acid transporter protein, but host cells transformed for purposes of cloning or amplifying nucleic acid hybridization probe DNA need not express the transporter. When expressed, each of the amino acid transporters of the invention will typically be located in the host cell membrane. See, Sambrook et al., ibid.

Cultures of cells derived from multicellular organisms are a desirable host for recombinant amino acid transporter protein synthesis. In principal, any higher eukaryotic cell culture is useful, whether from vertebrate or invertebrate culture. However, mammalian cells are preferred, as illustrated in the Examples. Propagation of such cells in cell culture has become a routine procedure. See *Tissue Culture*, Academic Press, Kruse & Patterson, editors (1973). Examples of useful host cell lines are human 293 cells, VERO and HeLa cells, Chinese hamster ovary (CHO) cell lines, and WI138, BHK, COS-7, CV, and MDCK cell lines. COS-7 cells are preferred.

The invention provides homogeneous compositions of each of the human EAAT1, EAAT2, EAAT3 and ASCT1 amino acid transporter proteins produced by transformed eukaryotic cells as provided herein. Each such homogeneous composition is intended to be comprised of the corresponding amino acid transporter protein that comprises at least 90% of the protein in such a homogenous composition. The invention also provides membrane preparation from cells expressing each of the amino acid transporter proteins as the result of transformation with a recombinant expression construct, as described herein.

Amino acid transporter proteins made from cloned genes in accordance with the present invention may be used for screening amino acid analogues, or agonist or antagonists of amino acid transport, or for determining the amount of such agonists or antagonists in a solution of interest (e.g., blood plasma or serum). For example, host cells may be transformed with a recombinant expression construct of the present invention, an amino acid transporter expressed in those host cells, and the cells or membranes thereof used to screen compounds for their effect on amino acid transport activity. By selection of host cells that do not ordinarily express a particular amino acid transporter, pure preparations of membranes containing the transporter can be obtained.

The recombinant expression constructs of the present invention are useful in molecular biology to transform cells which do not ordinarily express a particular amino acid transporter to thereafter express this receptor. Such cells are useful as intermediates for making cell membrane preparations useful for transporter activity assays, which are in turn useful for drug screening. The recombinant expression constructs of the present invention may also be useful in gene therapy. Cloned genes of the present invention, or fragments thereof, may also be used in gene therapy carried out homologous recombination or site-directed mutagenesis. See generally Thomas & Capecchi, 1987, Cell 51: 503–512; Bertling, 1987, Bioscience Reports 7: 107–112; Smithies et al., 1985, Nature 317: 230–234.

Oligonucleotides of the present invention are useful as diagnostic tools for probing amino acid transporter gene expression in tissues of humans and other animals. For example, tissues are probed in situ with oligonucleotide probes carrying detectable groups by conventional autoradiographic techniques, to investigate native expression of this receptor or pathological conditions relating thereto. Further, chromosomes can be probed to investigate the presence or absence of the corresponding amino acid transporter gene, and potential pathological conditions related thereto.

The invention also provides antibodies that are immunologically reactive to the amino acid transporter proteins or epitopes thereof provided by the invention. The antibodies provided by the invention may be raised, using methods well known in the art, in animals by inoculation with cells that express an amino acid transporter or epitopes thereof, cell membranes from such cells, whether crude membrane preparations or membranes purified using methods well known in the art, or purified preparations of proteins, including fusion proteins, particularly fusion proteins comprising epitopes of the amino acid transporter proteins of the invention fused to heterologous proteins and expressed using genetic engineering means in bacterial, yeast or eukaryotic cells, said proteins being isolated from such cells to varying degrees of homogeneity using conventional biochemical means. Synthetic peptides made using established synthetic means in vitro and optionally conjugated with heterologous sequences of amino acids, are also encompassed in these methods to produce the antibodies of the invention. Animals that are used for such inoculations include individuals from species comprising cows, sheep, pigs, mice, rats, rabbits, hamsters, goats and primates. Preferred animals for inoculation are rodents (including mice, rats, hamsters) and rabbits. The most preferred animal is the mouse.

Cells that can be used for such inoculations, or for any of the other means used in the invention, include any cell line which naturally expresses one of the amino acid transporters provided by the invention, or any cell or cell line that expresses one of the amino acid transporters of the invention, or any epitope thereof, as a result of molecular or genetic engineering, or that has been treated to increase the expression of an endogenous or heterologous amino acid transporter protein by physical, biochemical or genetic means. Preferred cells are E. coli and insect SF9 cells, most preferably E. coli cells, that have been transformed with a recombinant expression construct of the invention encoding an amino acid transporter protein, and that express the transporter therefrom.

The present invention also provides monoclonal antibodies that are immunologically reactive with an epitope derived from an amino acid transporter of the invention, or fragment thereof, present on the surface of such cells, preferably E. coli cells. Such antibodies are made using methods and techniques well known to those of skill in the art. Monoclonal antibodies provided by the present invention are produced by hybridoma cell lines, that are also provided by the invention and that are made by methods well known in the art.

Hybridoma cell lines are made by fusing individual cells of a myeloma cell line with spleen cells derived from animals immunized with cells expressing an amino acid transporter of the invention, as described above. The myeloma cell lines used in the invention include lines derived from myelomas of mice, rats, hamsters, primates and humans. Preferred myeloma cell lines are from mouse, and the most preferred mouse myeloma cell line is P3X63-Ag8.653. The animals from whom spleens are obtained after immunization are rats, mice and hamsters, preferably mice, most preferably Balb/c mice. Spleen cells and myeloma cells are fused using a number of methods well known in the art, including but not limited to incubation with inactivated Sendai virus and incubation in the presence of polyethylene glycol (PEG). The most preferred method for cell fusion is incubation in the presence of a solution of 45% (w/v) PEG-1450. Monoclonal antibodies produced by hybridoma cell lines can be harvested from cell culture supernatant fluids from in vitro cell growth; alternatively, hybridoma cells can be injected subcutaneously and/or into the peritoneal cavity of an animal, most preferably a mouse, and the monoclonal antibodies obtained from blood and/or ascites fluid.

Monoclonal antibodies provided by the present invention are also produced by recombinant genetic methods well known to those of skill in the art, and the present invention encompasses antibodies made by such methods that are immunologically reactive with an epitope of an amino acid transporter of the invention. The present invention also encompasses fragments, including but not limited to F(ab) and F(ab)'$_2$ fragments, of such antibody. Fragments are produced by any number of methods, including but not limited to proteolytic cleavage, chemical synthesis or preparation of such fragments by means of genetic engineering technology. The present invention also encompasses single-chain antibodies that are immunologically reactive with an epitope of an amino acid transporter, made by methods known to those of skill in the art.

The present invention also encompasses an epitope of an amino acid transporter of the invention, comprised of sequences and/or a conformation of sequences present in the transporter molecule. This epitope may be naturally occurring, or may be the result of proteolytic cleavage of a transporter molecule and isolation of an epitope-containing peptide or may be obtained by synthesis of an epitope-containing peptide using methods well known to those skilled in the art. The present invention also encompasses epitope peptides produced as a result of genetic engineering technology and synthesized by genetically engineered prokaryotic or eukaryotic cells.

The invention also includes chimeric antibodies, comprised of light chain and heavy chain peptides immunologically reactive to an amino acid transporter-derived epitope. The chimeric antibodies embodied in the present invention include those that are derived from naturally occurring antibodies as well as chimeric antibodies made by means of genetic engineering technology well known to those of skill in the art.

The Examples which follow are illustrative of specific embodiments of the invention, and various uses thereof. They set forth for explanatory purposes only, and are not to be taken as limiting the invention.

EXAMPLE 1

Isolation of a Human Neutral Amino Acid Transporter cDNA

In order to clone a novel human neutral amino acid transporter, a cDNA library was prepared from human motor cortex mRNA using standard techniques [see Sambrook et al., 1990, *Molecular Cloning: A Laboratory Manual* (Cold Spring Harbor Press: New York)]. Briefly, total RNA was isolated using the method of Chomczynski & Sacchi (1987, Anal. Biochem. 162: 156–159), wherein the tissue is disrupted and solubilized in a solution containing guanidinium isothiocyanate and the RNA purified by phenol/chloroform extractions. Total cellular RNA thus isolated was then enriched for poly ($A^+$) mRNA by oligo (dT) chromatography. A mixture of oligo (dT)-primed and random-primed mRNA was converted to cDNA using the Superscript Choice System (Bethesda Research Labs, Gaithersburg, Md.). cDNA was ligated into the cloning vector λZAPII (Strategene, La Jolla, Calif.), packaged into phage heads using commercially-available packaging extracts (Strategene) and used to infect E. coli. Lawns of infected bacterial cells were used to make plaque lifts for hybridization using standard conditions (see Sambrook, et al., ibid.).

This cDNA library was hybridized with a $^{32}$P-labeled oligonucleotide having the following sequence:

5'-CTG(A/G)GC(A/G)ATGAA(A/G)ATGGCAGCCAGGGC(C)TCATACAGGGCTGTGCC(A/G)TCCATGTT(A/G)ATGGT(A/G)GC-3' (SEQ ID NO:1).

(This oligonucleotide was obtained commercially from Oligos, Etc., Wilsonville, Oreg.). This oligonucleotide was chosen on the basis of shared homology between a cloned rat glutamate transporter gene (GLAST1) and the bacterial glutamate transporter gene gltP (see Storck et al. ibid. and Wallace et al., ibid.), which suggested an important and conserved structural motif. Hybridization was performed at 50° C. in a solution containing 0.5M $Na_2HPO_4$ (pH 7.15)/ 7% sodium dodecyl sulfate (SDS) and the filters were washed at 60° C. in 2X SSPE [0.36M NaCl/20 mM sodium phosphate (pH 7.7)/2 mM ethylenediamine tetraacetic acid (EDTA)] and 1% SDS. Hybridizing clones were identified by autoradiography at −70° C. using tungsten-containing intensifying screens (DuPont-NEN, Wilmington, Del.).

More than 20 positively-hybridizing clones were detected in screening experiments using the above-described primer. One of these clones was excised from the cloning vector in vivo by superinfection with a defective filamentous phage that recognizes and excises cloned insert sequences along with adjacent modified phage replication-form sequences (termed pBluescript SK and available from Strategene). This clone contained a 2.7 kilobase (kb) insert, which was sequenced using the dideoxy-chain termination method of Sanger et al. (1977, Proc. Natl. Acad. Sci. USA 74: 5463), using Sequenase 2.0, a modified form of bacteriophage T7 DNA polymerase (U.S. Biochemical Corp., Cleveland, Ohio). The nucleotide sequence of the portion of this clone containing an open reading frame (encoding the ASCT1 gene) is shown in FIGS. 1A through 1E.

This ASCT1 clone (SEQ ID No.:2) was found to be comprised of about 180 bp of 5' untranslated region, about 900 bp of 3' untranslated region and an open reading frame of 1596 bp encoding the ASCT1 transporter protein (comprising 532 amino acids). The initiator methionine codon was found to be the first methionine codon 3' to an in-frame stop codon and embedded within the consensus sequence for eukaryotic translation initiation (see Kozak, 1987, Nucleic Acids Res 15: 8125–8132). The ASCT1 amino acid sequence (SEQ ID No.:3; also shown in FIGS. 1A through 1E) was found to exhibit similarity to other known glutamate transporter subtypes (an amino acid sequence comparison is shown in FIGS. 5A and 5B). An amino acid comparison between glutamate transporters from rat (GLAST1 and GLT-1) and rabbit (EAAC1) showed 39%, 34% and 39% sequence identity (respectively) between these amino acid transporter proteins (shown in FIGS. 5A and 5B by shaded boxes). This degree of sequence identity is comparable to the sequence identity between these glutamate subtypes themselves. Both the amino and carboxyl termini were found to be divergent between these transporter proteins, and diversity was also found in the extracellular domains of these putative protein sequences, which contain conserved potential N-glycosylation sites (shown in FIGS. 5A and 5B by open boxes). It was noted that a highly conserved sequence (comprising the amino acids --LYEA--) in the glutamate transporters was replaced by the unrelated amino acid sequence --IFQC-- in the ASCT1 sequence (at positions 385–387 of the ASCT1 amino acid sequence shown in FIGS. 5A and 5B). 6–10 putative transmembrane domains were found using the algorithm of Eisenberg et al. (1984, J. Molec. Biol. 179: 125–142). On the basis of these data ASCT1 was determined to encode a related but distinct and novel member of the amino acid transporter family.

EXAMPLE 2

Isolation of Human Excitatory Amino Acid Transporter cDNA

The remaining (>20) positively-hybridizing clones from the human motor cortex cDNA library detected by hybridization with the primer described in Example 1 (SEQ ID No.:1) were isolated and the corresponding plasmids obtained by in vivo excision after superinfection with defective phage as described in Example 1 above. These resulting plasmids were isolated and purified using conventional techniques (see Sambrook et al., ibid.). Four classes of clones were distinguished based on differential hybridization experiments using each clone as a hybridization probe against a panel of the remaining clones one after another, where conditions of hybridization stringency were varied to distinguish between each of the classes.

Representative clones from each class were sequenced as described in Example 1. One class of clones represented the ASCT1 cDNA sequences described in Example 1. The other three classes were found to encode novel proteins having amino acid sequences homologous to but distinct from the human ASCT1 sequence. Clone GT5 was determined to contain a 4.0 kb insert encoding a protein having a predicted amino acid sequence (termed EAAT1; SEQ ID No.:4) homologous to but distinct from the rat GLAST1 cDNA clone of Storck et al. (ibid.). Clone GT13 was determined to contain a 2.5 kb insert comprising an open reading frame corresponding to a full-length coding sequence for a novel human transporter gene termed EAAT2 (SEQ ID No.:6). Clone GT11 was found to contain a partial sequence of another novel human transporter termed EAAT3. The EAAT3 clone was used to re-screen the cDNA library described in Example 1. The result of these re-screening experiments was the isolation of Clone GT11B containing a full-length open reading frame encoding EAAT3 (SEQ ID No.:8).

FIGS. 11A and 11B shows the results of alignment of the predicted amino acid sequences of the three novel glutamate transporters of the invention. Nine regions of Eisenberg algorithm predicted hydrophobicity are denoted by overlining, and potential sites of N-linked glycosylation (consensus sequence N-X-S/T, where X is any amino acid) are indicated by the circles asparagine (N) residues. EAAT1 shares 47% (253/542) amino acid sequence identity with EAAT2 and 46% (262/574) sequence identity with EAAT3, whereas the EAAT2 sequence is 45% (259/574) identical to the predicted EAAT3 sequence. Cross-species comparisons of the predicted amino acid sequences of these novel human glutamate transporters revealed the following relationships: EAAT1 was found to be 96% homologous with the rat GLAST1 sequence (Storck et al., ibid.); EAAT2 was found to be 90% homologous with the rat GLT1 sequence (Pines et al., 1992, ibid.); and EAAT3 was found to be 93% homologous with the rabbit EAAC1 sequence (Kanai & Hediger, 1992, ibid.). These results indicate that EAAT1, EAAT2 and EAAT3 are related but distinct members of the glutamate transporter family of amino acid transporters.

EXAMPLE 3

Functional Expression of the ASCT1 Amino Acid Transporter Gene in Xenopus Oocytes The sequence similarity between ASCT1 and the glutamate transporters GLAST1, EAAC1 and GLT-1 suggested that the protein encoded by ASCT1 was an amino acid transporter. The ability of the ASCT1 gene product to transport amino acids, and the identity of which amino acids might be transported by this gene product, was assayed in *Xenopus laevis* oocytes following microinjection of in vitro synthesized ASCT1 RNA.

Briefly, the coding sequence of the ASCT1 cDNA was isolated with unique flanking restriction sites using a PCR-based assay. In this assay, each of the complementary primers used for PCR amplification of the coding sequence contained a sequence encoding a unique restriction enzyme recognition site at the 5' terminus of each PCR primer. For ASCT1, the sense primer contained a KpnI recognition sequence (GGTAC↓C), and the antisense primer contained an XbaI recognition sequence (T↓CTAGA) at their respective 5' termini. Each of the PCR primers used for amplifying ASCT1 sequences had the following sequence:

ASCT1 sense primer:
5'-CGCGGGTACCGCCATGGAGAAGAGCAAC-3' (SEQ ID NO: 10);

ASCT1 antisense primer:
5'-CGCGTCTAGATCACAGAACCGACTCCTTG-3' (SEQ ID NO: 11).

PCR amplification was performed for 30 cycles, each cycle comprising 1 minute at 94° C., 30 seconds at 55° C. and 2 minutes at 72° C. Following the PCR, the product of the amplification reaction was purified using standard techniques (Saiki et al., 1988, Science 239: 487–491). The DNA then digested with the restriction enzymes KpnI and XbaI and then cloned into the polylinker of an oocyte transcription vector (pOTV; see Wang et al., 1991, Nature 32: 729–731) that had been digested with KpnI and XbaI. Synthetic RNA was then transcribed in vitro from this clone using the method of Kavanaugh et al. (1992, J. Biol. Chem. 267: 22007–22009) employing bacteriophage T7 RNA polymerase (New England Biolabs, Beverly, Mass.). 20–50 nL of ASCT1 RNA (at a concentration of about 400 µg/mL) was injected into defolliculated stage V-VI Xenopus oocytes excised from female Xenopus laevis anesthetized by immersion in 3-aminobenzoic acid for 60 min. Excised oocytes were treated with collagenase II (Sigma Chemical Co., St. Louis, Mo.) in calcium-free Barth's saline solution [comprising 88 mM NaCl, 1 mM KCl, 2.4 mM NaHCO$_3$, 0.82 mM MgSO$_4$, 7.5 mM Tris-HCl (pH 7.6), 50U/mL Nystatin (Sigma) and 0.1 mg/mL gentamycin (Sigma)] for 60 min., and then incubated overnight at 15° C. in 50% Leibowitz's L-15 media (Grand Island Biological Co. (GIBCO), Long Island, N.Y.). After overnight incubation the oocytes were mechanically defolliculated and then were injected with ASCT-1 RNA and incubated at 19° C. for 48 h (see Kim et al., 1991, Nature 352: 725–728 for further details of Xenopus oocyte preparation and microinjection).

Amino acid transport in such oocytes was assayed using [$^3$pH] alanine, [$^3$H] serine or [$^{35}$S] cysteine (obtained from New England Nuclear, Boston, Mass.). Briefly, microinjected oocytes were patch-clamped at −60 mV using a Dagan TEV-200 clamp amplifier with an Axon Instruments (Foster City, Calif.) TL-1 A/D interface controlled by pCLAMP software (Axon Instruments) (see Kavanaugh et al., 1992, J. Biol. Chem. 267: 22007–22009 for a detailed review of this methodology) and continuously superfused with ND-96 buffer (consisting of 96 mM NaCl/2 mM KCl/1.8 mM CaCl$_2$/1 mM MgCl$_2$/5 mM HEPES, pH 7.5). For transport measurements, this solution was changed to a solution containing varying concentrations of the radiolabeled amino acids in ND-96 buffer.

Figure 6B:
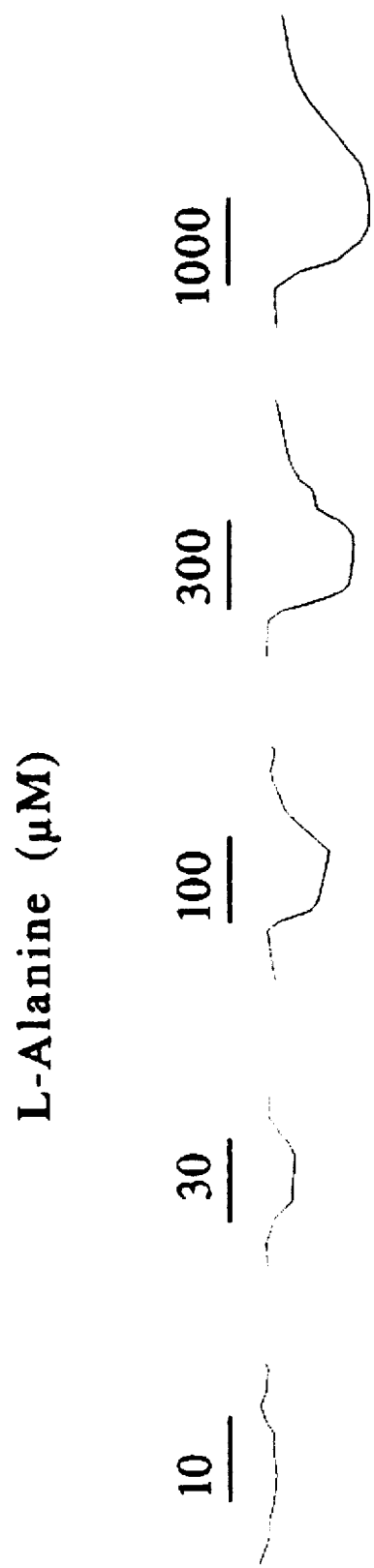
Figure 6C:
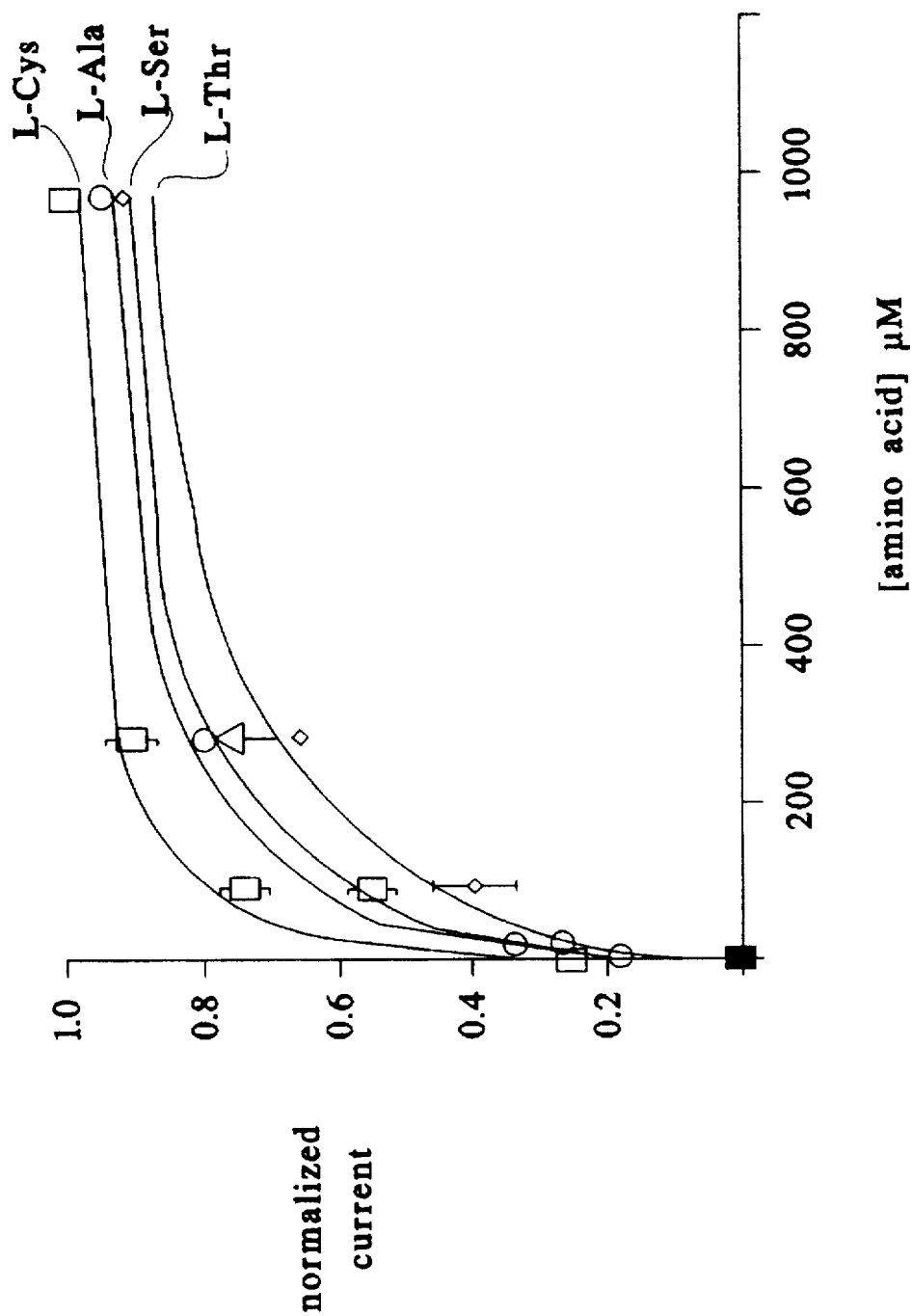

Three types of experiments were performed, the results of each being shown in FIGS. 6A through 6C. As shown in FIG. 6A, when such oocytes were contacted with ND-96 buffer containing L-alanine, L-serine or L-cysteine, a hyperpolarization of the cell plasma membrane was produced as the result of inward currents of Na$^+$ ion, as has been associated with other known amino acid transporters (see Nicholls, ibid.). In contrast, the amino acids L-lysine, L-glutamine, proline, glycine, methionine, arginine, glutamine, asparagine, and leucine, and the amino acid analogues N-methylalanine, had no effect at much higher concentrations (i.e., about 1 mM). Another amino acid analogue, 2-methylaminoisobutyric acid (MAIB), which is known to be specific for the amino acid transporter type A (Christensen et al., 1967, J. Biol. Chem. 242: 5237–5246), also had no effect at concentrations of 1 mM. Further, in competition experiments, contacting such oocytes with a solution containing MAIB at a concentration of 10 mM had no effect on the rate of uptake of [$^3$H] alanine present at 100 µM. The response of the oocytes was also stereospecific (D-alanine was found to produce only 12±3% of the response produced by treatment of these oocytes with L-alanine) and Na$^+$ ion-specific (no response was detected when Na$^+$ ions were replaced by tris-hydroxyethylaminomethane buffer, shown in FIG. 6A). The rate of radiolabeled amino acid uptake (in pmol/min per oocyte, determined at an amino acid concentration of 100 µM) for the amino acids alanine, cysteine and serine are shown in Table I.

The uptake currents measured in ASCT1-injected oocytes were found to be both dose-dependent and saturable. FIG. 6B illustrates the dose-dependency of the electrochemical response of ASCT1-injected oocytes to L-alanine. The intensity of the response (equivalent to the amount of current flow into the cell) increased with the concentration of L-alanine from 10 µM to 1 mM. The saturability of this response is shown in FIG. 6C. In this Figure, the current, normalized to the maximum response obtained with L-alanine, is shown plotted against the extracellular amino acid concentration of each amino acid tested. For the L-stereoisomers of alanine, serine, cysteine and threonine, the inward current flux was found to saturate and reach a plateau at concentrations from 400–1000 µM. More detailed analyses of the kinetics of amino acid influx were performed by least squares linear regression analysis of induced inward current ([I]) plotted as a function of substrate amino acid concentration ([S]), using the equation shown in the legend of Table II. Data were averaged from all oocytes tested, and the results expressed as the mean±standard error are shown in Table II.

These results indicated that the cloned ASCT1 cDNA derived from human motor cortex mRNA encoded an amino acid transporter that was specific for Alanine, Serine, Cysteine (and Threonine) and that amino acid transport activity was accompanied by an inward current flow mediated by sodium ions. These results demonstrated that the novel amino acid transporter isolated herein was related to but distinct from other, known transporters, such as the so-called ASC amino acid transporters (Christensen et al., ibid.).

EXAMPLE 4

Functional Expression of the Glutamate Amino Acid Transporter Genes in Xenogus Oocytes Similar series of experiments were performed using RNA synthesized in vitro from constructs containing each of the cloned glutamine transporter genes of the invention. In these experiments, each of the PCR primers used to amplify each of the glutamate transporter genes had the following sequence:

EAAT1 sense primer:
5'-CGCGGGTACCAATATGACTAAAAGCAATG-3' (SEQ ID NO:12);

EAAT1 antisense primer:
5'-CGCGTCTAGACTACATCTTGGTTTCACTG-3' (SEQ ID NO:13);

EAAT2 sense primer:

5'-CGCGGGTACCACCATGGCATCTACGGAAG-3' (SEQ ID NO:14).

EAAT2 antisense primer:
5'-CGCGTCTAGATTATTATTTCTCACGTTTCCAAG-3' (SEQ ID NO:15)

EAAT3 sense primer:
5'-CGCGGGTACCGCCATGGGGAAACCGGCG-3' (SEQ ID NO:16);

EAAT3 antisense primer:
5'-CGCGGGATCCCTAGAACTGTGAGGTCTG-3' (SEQ ID NO:17).

As can be determined by inspection of these sequences, each of the sense primers contained a KpnI recognition sequence (GGTAC↓C), and each of the antisense primers contained an XbaI recognition sequence (T↓CTAGA) at the 5' terminus of each primer for EAAT1 and EAAT2. For EAAT3, the sense primer contained a KpnI recognition sequence, and the antisense primer contained a BamHI recognition sequence (G↓GATCC) at the 5' terminus of each primer.

PCR amplification was performed for 30 cycles, each cycle comprising 1 minute at 94° C., 30 seconds at 50° C. and 2 minutes at 72° C. Following the PCR, each of the PCR products was isolated and cloned into pOTV as described in Example 3, from which RNA encoding each glutamate transporter was synthesized in vitro as described.

Figure 12A:
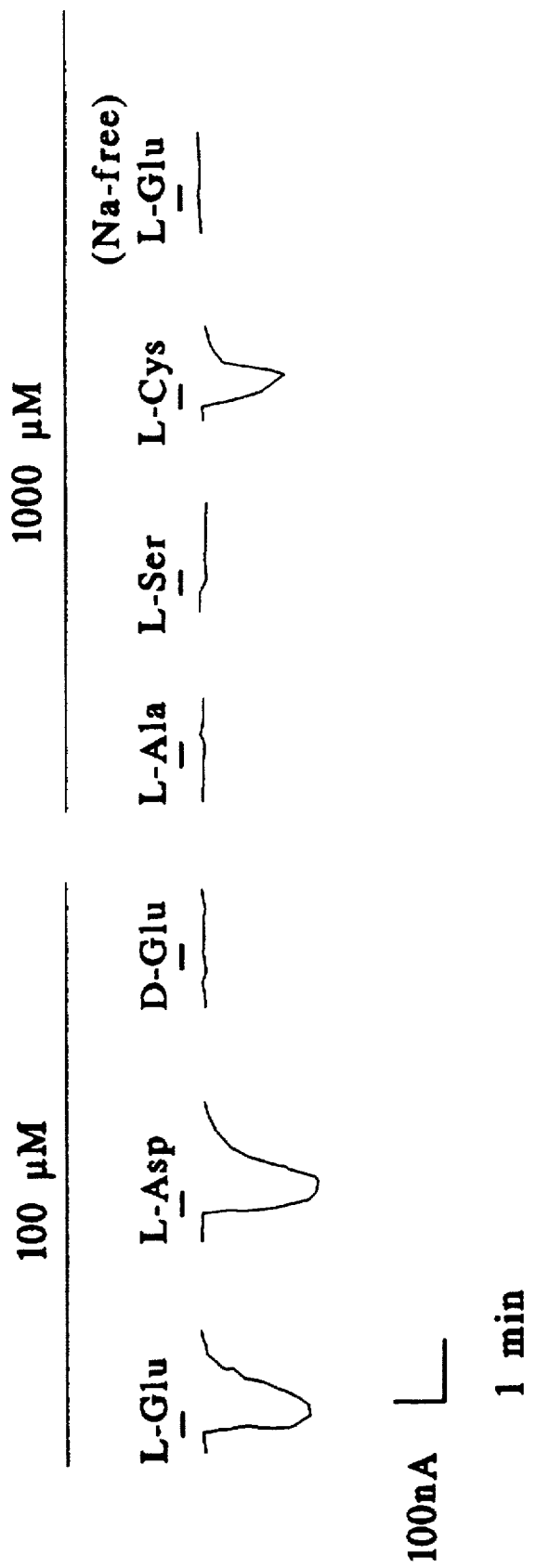
FIGS. 12A, 12B and 12C illustrate electrogenic uptake of various amino acids (FIG. 12A) and the concentration dependence of such uptake of L-glutamate (FIGS. 12B and 12C) in $Xenopus\ laevis$ oocytes expressing the EAAT1 amino acid transporter.
Figure 12B:
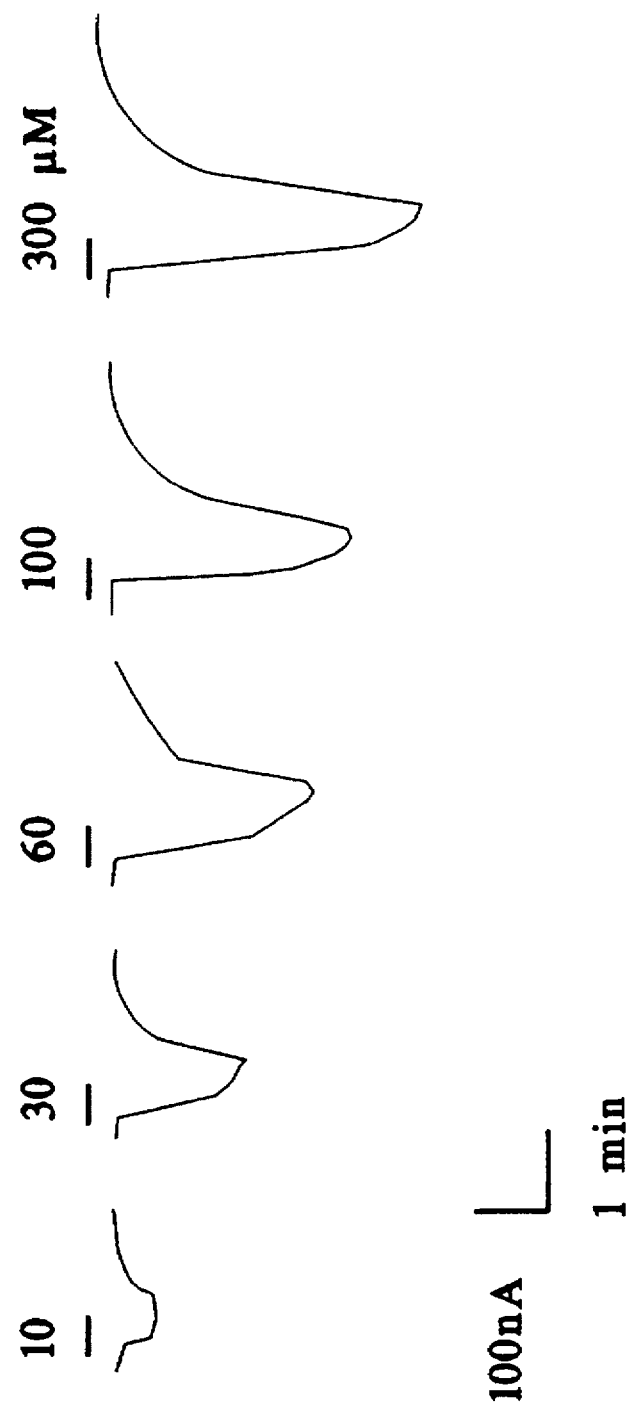
Figure 12C:
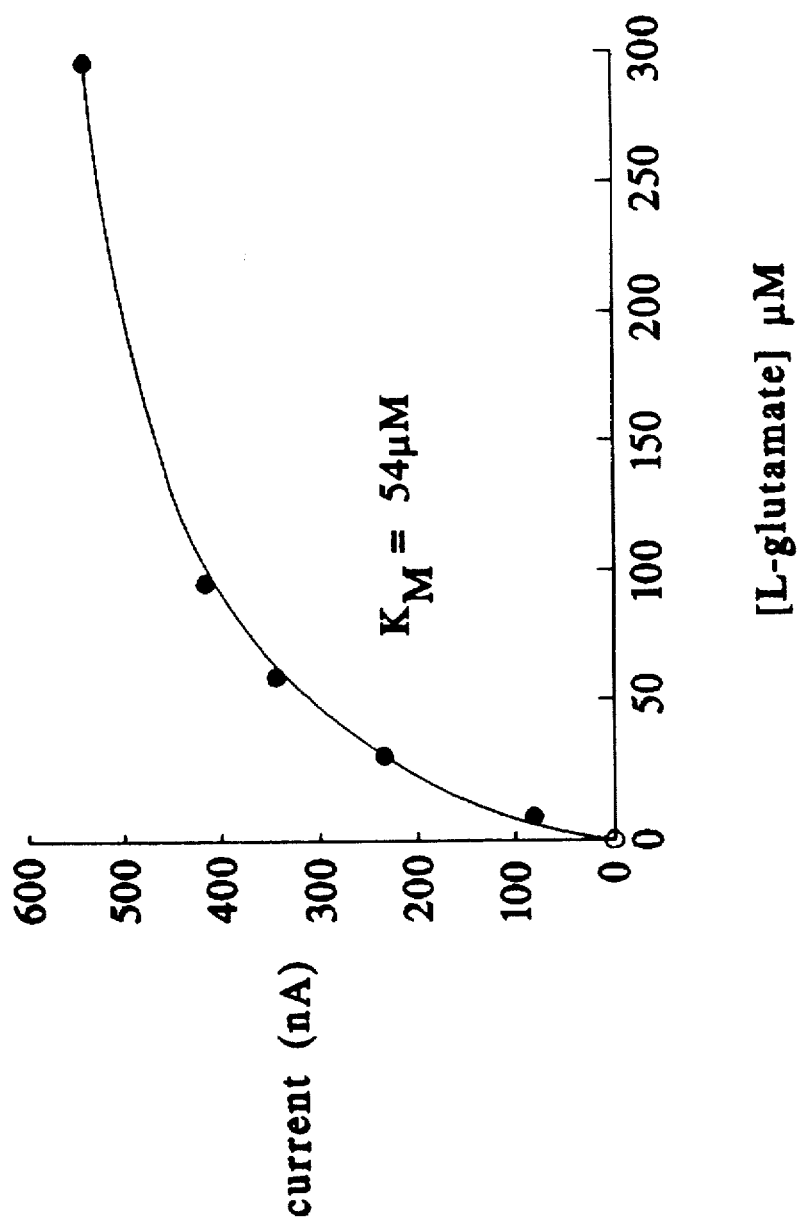

Such RNA preparations were each introduced into Xenopus oocytes as described in Example 3 to enable expression therein. Amino acid uptake experiments were performed on such oocytes expressing each of the glutamate transporters, also as described in Example 3. Results of such experiments are shown in FIGS. 12A and 12B. FIG. 12A shows electrogenic uptake of various amino acids in EAAT1-expressing oocytes. Both L-glutamate and L-aspartate caused inward currents as high as several microamps when added to the incubation media (ND-96) at a concentration of 100 µM. In contrast, incubation of EAAT1-expressing oocytes with L-alanine and L-serine at ten-fold higher concentrations (i.e., 1000 µM) did not result in electrogenic uptake of these amino acids. Uptake was found to be stereospecific, since L-glutamate incubation did not result in the generation of an inward electric current, and sodium-ion specific, since electrogenic uptake of L-glutamate was abolished by incubation in sodium ion-free media (choline was used to replace sodium in these incubations).

These experiments also demonstrated the surprising result that cysteine, when present at high enough extracellular concentrations (i.e., 1000 µM) was capable of being electrogenically transported by the EAAT1 transporter. Cysteine had not previously been reported to be a glutamate transporter substrate; however, amino acid sequence analysis of the EAAT1 transporter showed structural similarities between EAAT1 and the ASCT1 transporter, which was demonstrated herein to transport cysteine (see Example 3). As will be discussed in detail below, the EAAT1 transporter displays a $K_m$ for glutamate of 54 µM; in contrast, the $K_m$ for cysteine was found to be 300 µM. The EAAT1 transporter thus displays a pattern of substrate specificity that is distinct from that of any known glutamate transporter.

FIG. 12B illustrates the results of biochemical analysis of substrate affinity of the EAAT1 transporter for glutamate, said results being plotted as current versus substrate concentration to yield an estimate of the $K_m$. These experiments were performed essentially as described for the ASCT1 transporter in Example 3. Patch-clamped oocytes expressing the EAAT1 transporter were incubated with varying extracellular concentrations of L-glutamate, and the magnitude of the resulting inward currents determined. From these experiments, the plotted relationship between the magnitude of the inward current and the extracellular L-glutamate concentration was determined, resulting in an estimate for $K_m$ equal to 54 µM for L-glutamate. These results were in good agreement with results obtained in COS-7 cells expressing the EAAT1 transporter, described hereinbelow (see Example 5).

EXAMPLE 5

Functional Expression of the Amino Acid Transporter Genes in COS-7 Cells

DNA fragments comprising the coding sequences of the novel glutamate transporter genes of the invention were excised from the pOTV constructs described in Example 3 and subcloned into the mammalian expression plasmid pCMV5 (Anderson et al., 1989, J. Biol. Chem. 264: 8222–8229). These mammalian expression constructs were used for transient expression assays of glutamate transporter protein function after transfection of each of these constructs into COS-7 cells (Gluzman, 1981, Cell 23: 175–182).

Each of the pCMV5 constructs corresponding to EAAT1, EAAT2 and EAAT3 were introduced into COS-7 cells by DEAE-dextran facilitated transfection (see Sambrook et al., ibid.). Two day following transfection, the transfected cells were washed three times in phosphate-buffered saline (PBS) and then incubated with a mixture of radiolabeled amino acid ([$^3$H]-L-glutamate or [$^3$H]-D-aspartate; Dupont-NEN) and non-radiolabeled amino acid for 10 min. After incubation, the cells were washed three times with ice-cold PBS, solubilized with a solution of 0.1% sodium dodecyl sulfate (SDS) and the amount of radioactivity associated with the cells determined using standard liquid scintillation counting methods. The results of these experiments showed that cells transfected with each of the glutamate transporter constructs accumulated significantly-higher (between 10- and 100-fold higher) amounts of radioactivity than did mock (i.e., pCMV5 plasmid) transfected COS-7 cells (which accumulation represented endogenous COS-7 cell uptake of radioactive glutamate). The course of radioactive glutamate uptake was found to be linear for at least 20 min in assays performed at room temperature.

Figure 7A:
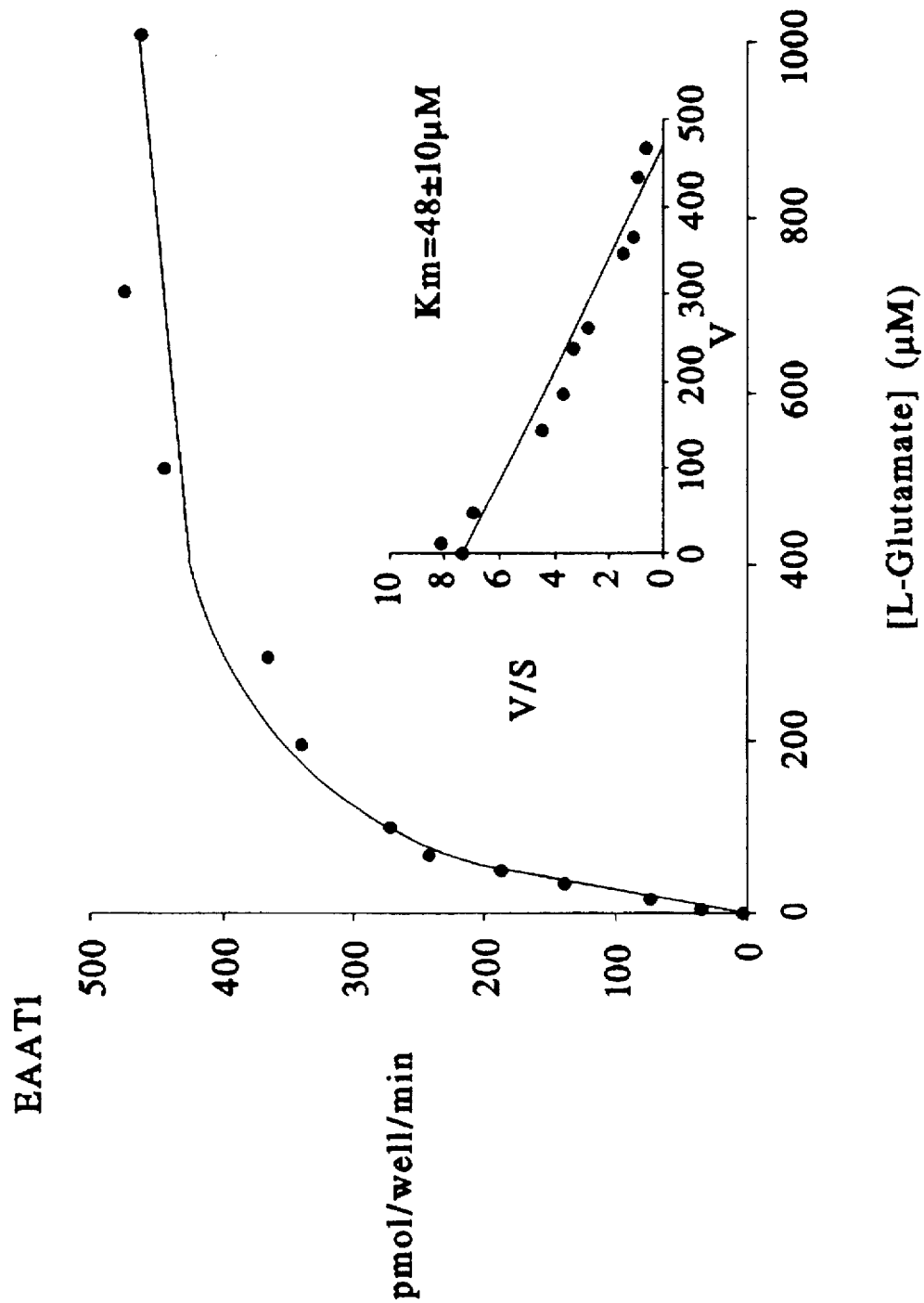
FIGS. 7A through 7F presents glutamate transporter kinetics of EAAT1 (FIGS. 7A and 7B), EAAT2 (FIGS. 7C and 7B) and EAAT3 (FIGS. 7E and 7F).
Figure 7B:
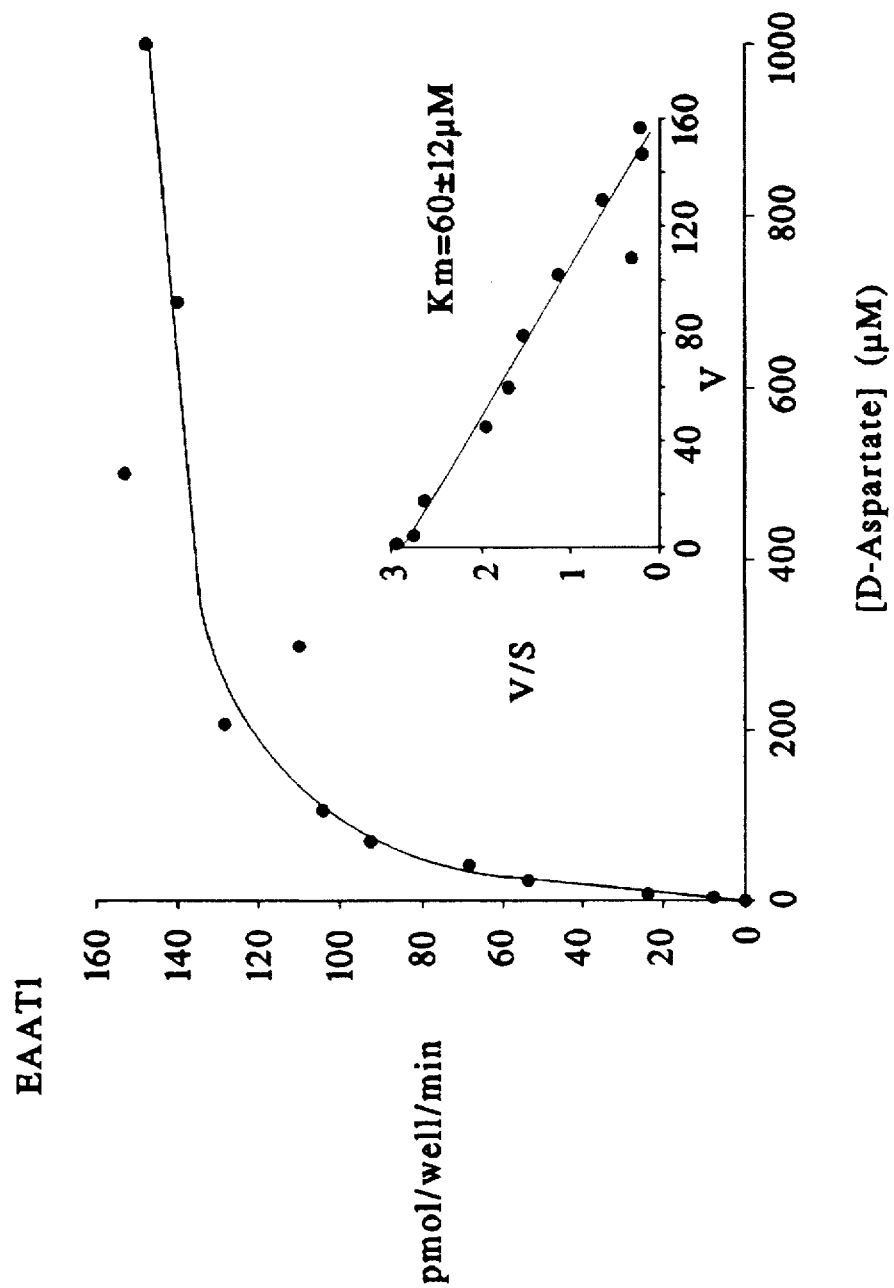
Figure 7C:
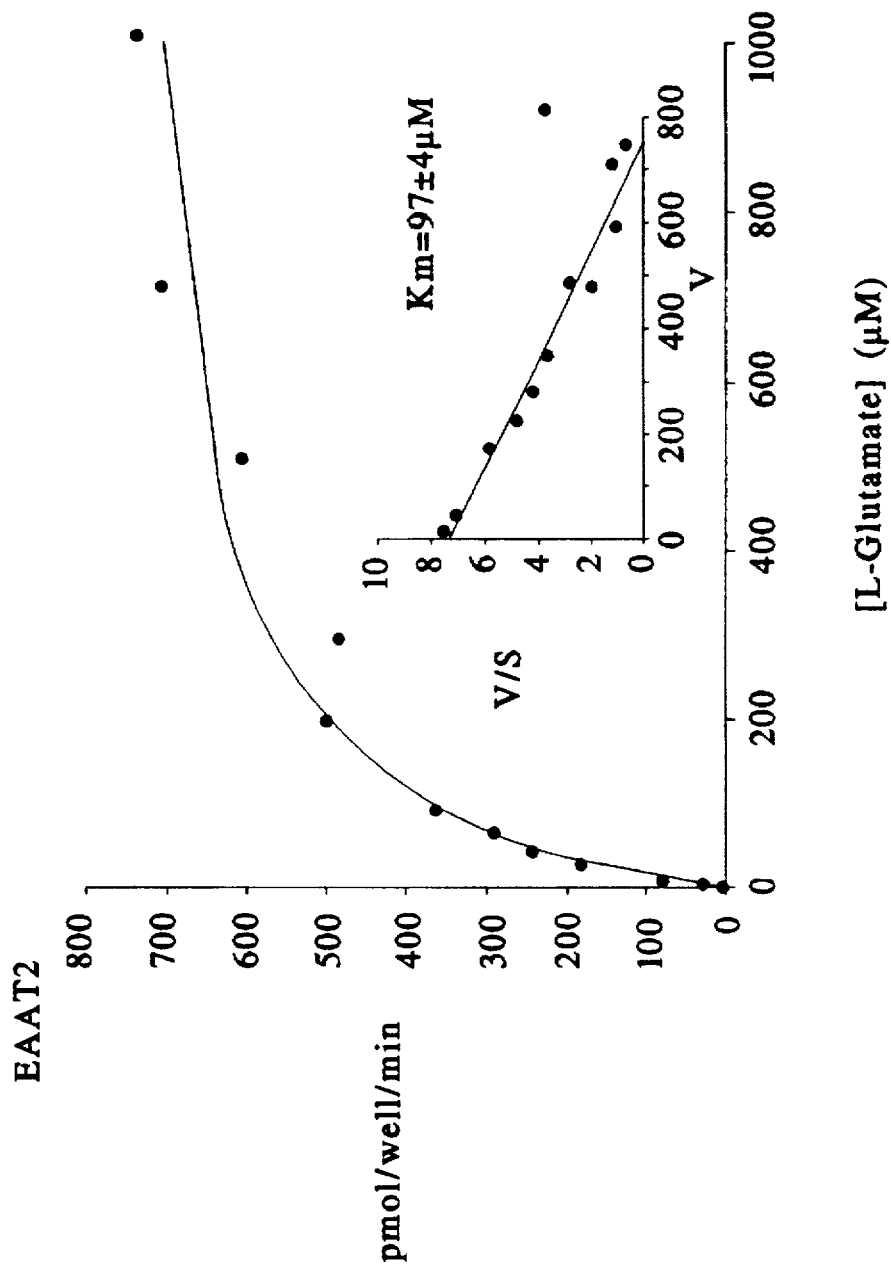
Figure 7D:
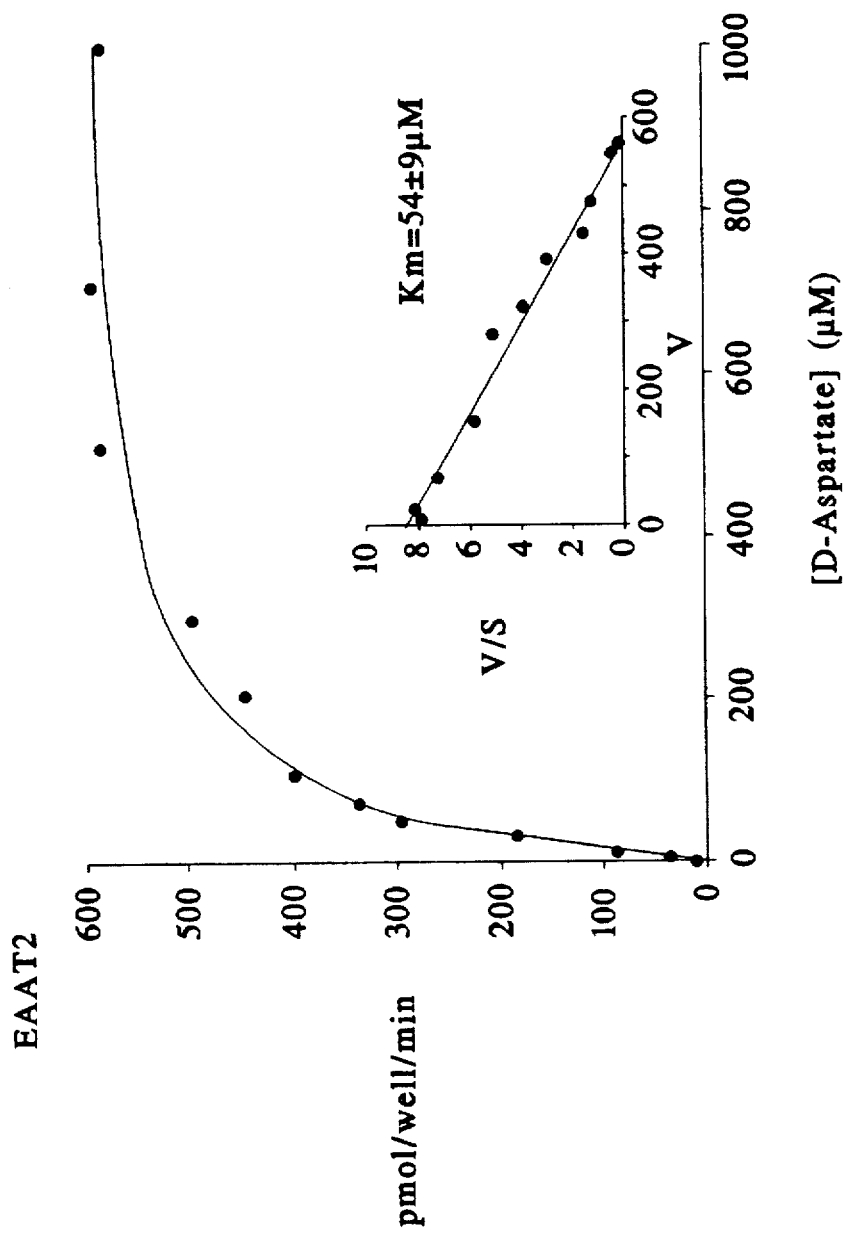
Figure 7E:
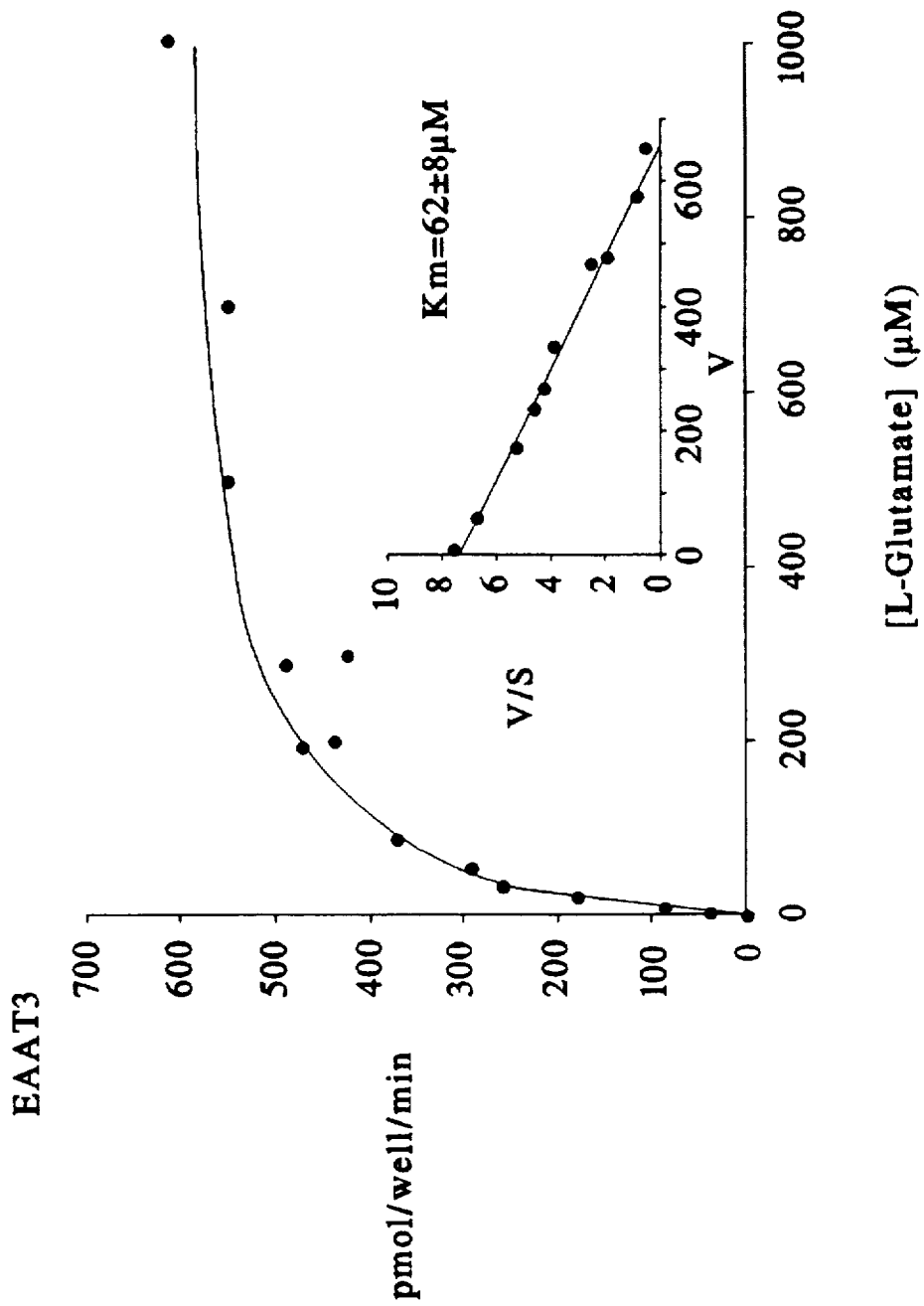
Figure 7F:
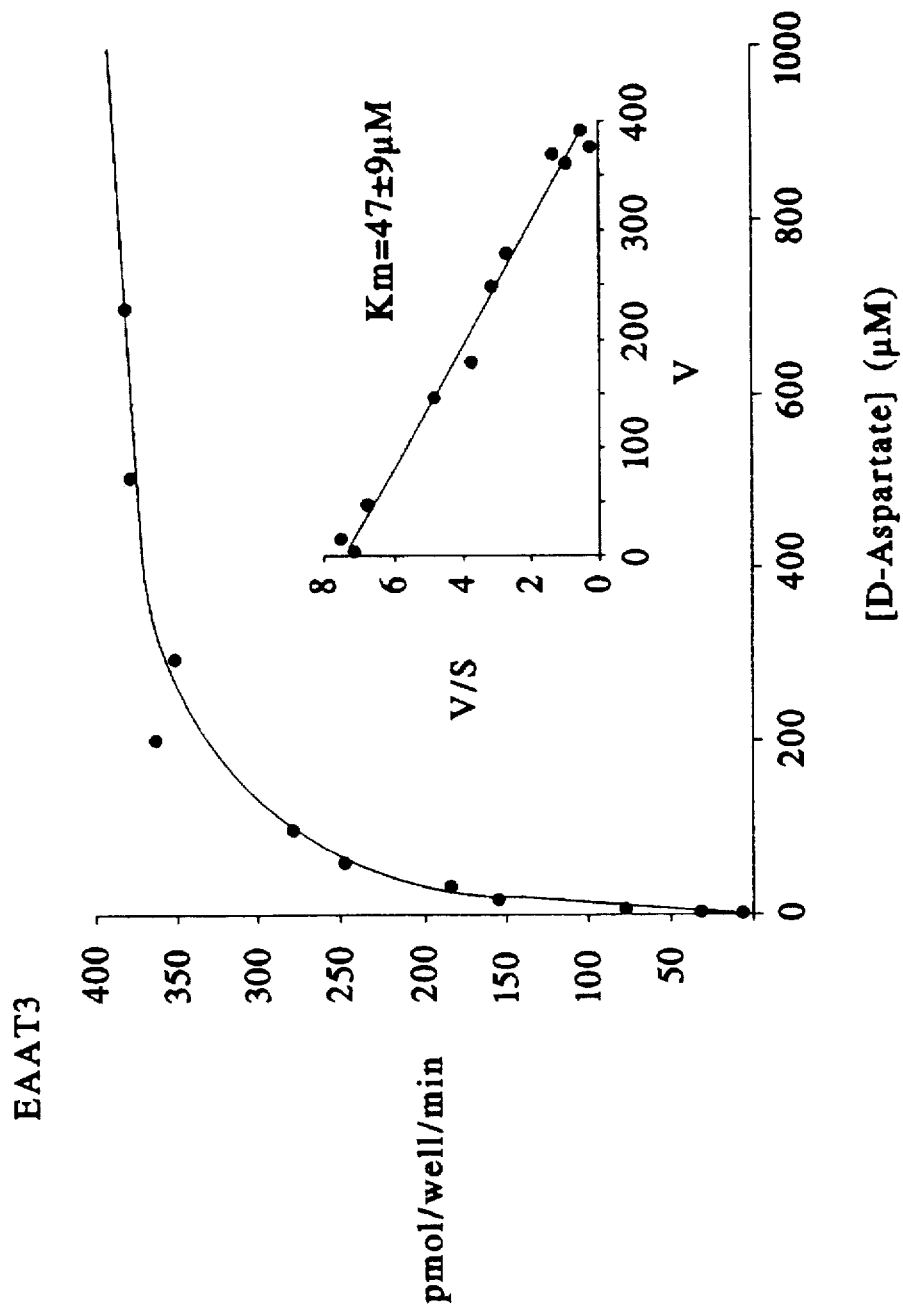

These results are shown in FIGS. 7A through 7F. In the Figure, EAAT1 transporter kinetics of glutamate uptake are depicted in FIG. 7A and of aspartate are shown in FIG. 7B. Similarly, EAAT2 kinetics for glutamate and aspartate are shown in FIGS. 7C and 7D, respectively. Finally, EAAT3 kinetics are shown in FIG. 7E (glutamate) and FIG. 7F (aspartate). Each data point was determined by incubating a COS cell culture transfected with the appropriate pCMV5-glutamate transporter clone with 100 nM of radiolabeled amino acid and increasing amounts of unlabeled amino acid. Results are plotted as uptake velocity (in pmol/cell culture/min) minus endogenous uptake versus total amino acid concentration, and each data point was performed in triplicate. The results show that both glutamate and aspartate uptake mediated by each of the three novel human glutamate transporters is saturable. Insets in each Panel depict Eadie-Hofstee plots of initial velocity data, from which $K_m$ values were determined. The $K_m$ values are shown as the mean±standard error based on at least three independent experiments. These results show that each of the three novel transporter proteins comprising the instant invention is functionally competent as an amino acid transporter when expressed in a culture of mammalian cells, and that each of the novel transporters encoded by the cDNA clones EAAT1, EAAT2 and EAAT3 displays a collection of biochemical properties consistent with their designation as human glutamate transporter proteins.

EXAMPLE 6

Inhibitor Potency Analyses Using COS-7 Cells Expressing Amino Acid Transporter Proteins COS-7 cell cultures transformed with pCMV5-human glutamate transporter constructs as described in Example 4 were used to characterize the pharmacological properties of each of these transporter proteins relative to a variety of known glutamate transporter inhibitors. These assays were performed essentially as described in Example 4, with the exception that varying amounts of each of a number of known inhibitor compounds were included in the incubations.

Figure 8A:
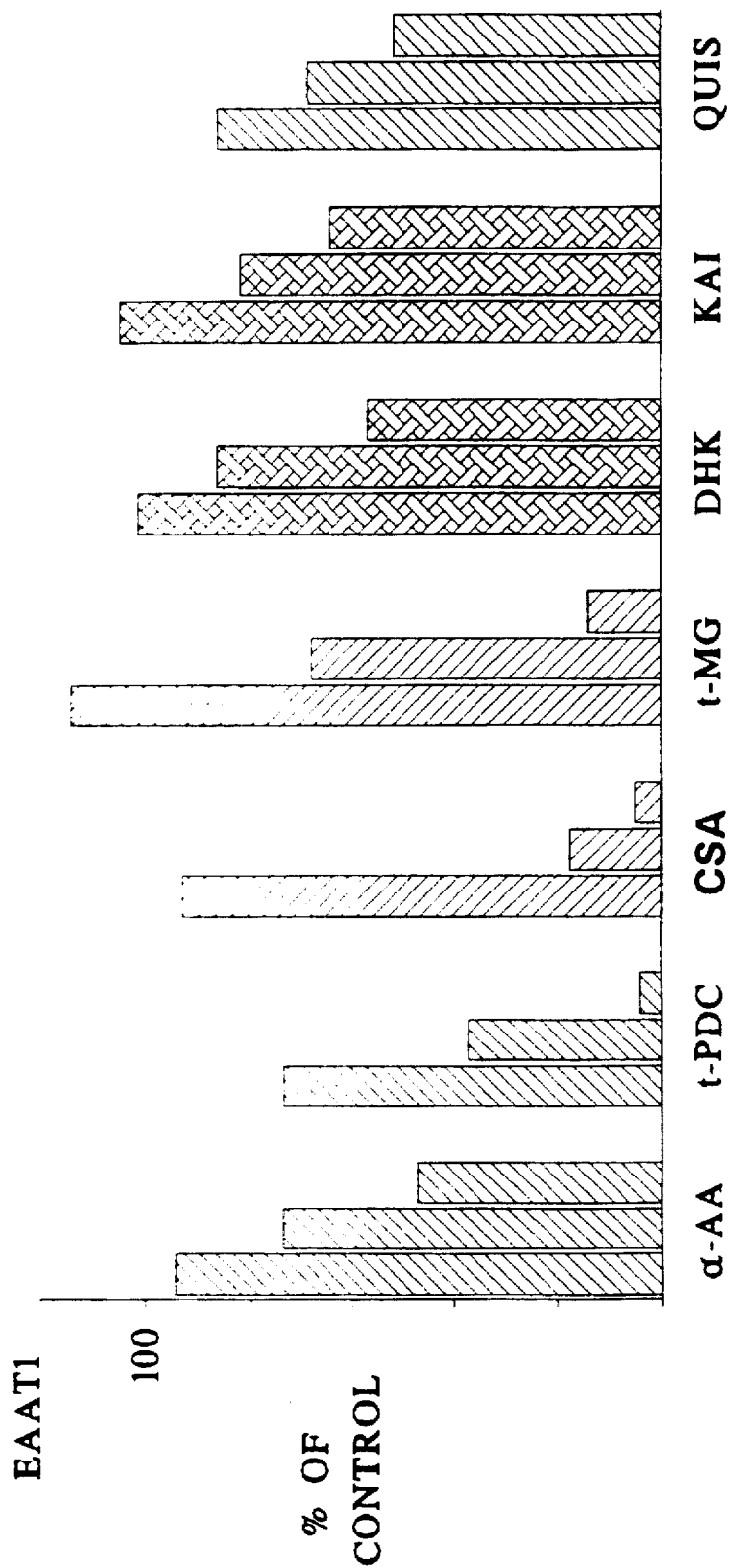
FIGS. 8A through 8C represents the pharmacological responsiveness of glutamate transport by the human excitatory amino acid transporters EAAT1, EAAT2 and EAAT3 when contacted with the indicated competitors/inhibitors at 1 μml-glutamate and inhibitor/competitor concentrations of 3 μm, 100 μm or 3 mM.
Figure 8B:
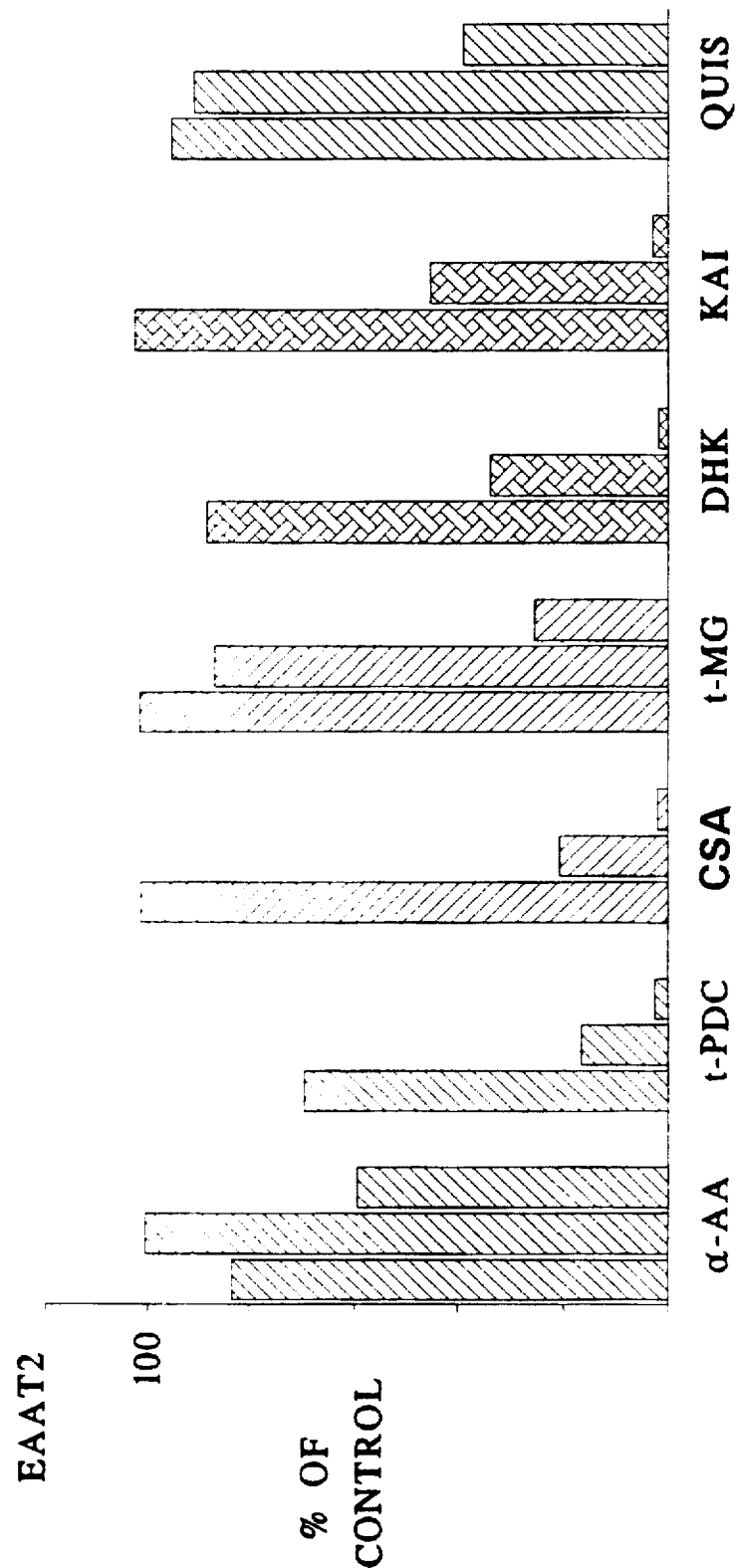
Figure 8C:
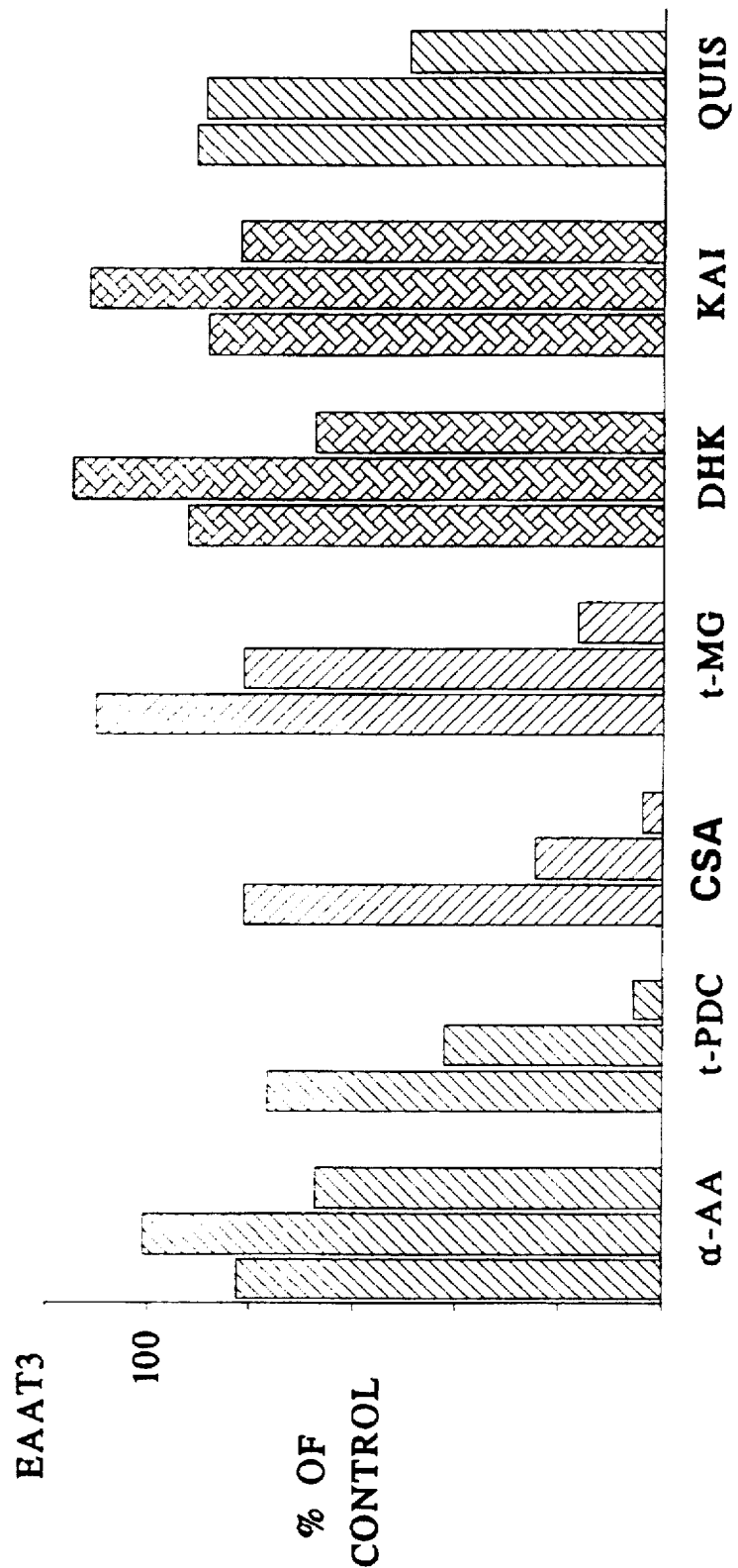

The results of these experiments are shown in FIGS. 8A through 8C. The data in FIGS. 8A through 8C represent the pharmacological responsiveness of glutamate transport by the human excitatory amino acid transporters EAAT1, EAAT2 and EAAT3 when contacted with the following competitors/inhibitors: L-threo-β-hydroxyaspartate (THA); L-trans-pyrrolidine-2,4-dicarboxylate (PDC); L-serine-O-sulfate (SOS); dihydrokainate (DHK); and kainate (KAI). In these experiments, uptake of 1 µM of [$^3$H]-L-glutamate was determined in the presence of the indicated amounts of each of the inhibitors. As can be seen from the FIGURES, each of the glutamate transporter proteins of the invention displays a characteristic pattern of sensitivity to the inhibitors. Thus, the relative potency of inhibition of radiolabeled glutamate uptake was found to be as follows for the EAAT1 and EAAT3 transporter proteins:

THA<PDC<SOS<<DHK, KAI, whereas the inhibition pattern for EAAT2 was as follows:

PDC<THA<DHK<KAI<SOS.

These results, as well as results obtained from similar experiments performed with L-cysteate, L-cysteine sulfinic acid, β-glutamate and L-aspartate-β-hydroxymate, are shown in Table III. Even though the relative pattern of inhibition was the same for EAAT1 and EAAT3, the results shown in the Table support the finding that each of the glutamate transporters of the invention is uniquely characterized by its sensitivity to this panel of glutamate uptake inhibitors.

In addition, a number of reported inhibitors were found to be ineffective when tested with COS cell culture expressing each of the novel glutamate transporter proteins of the invention. These include cis-1-aminocyclobutane-1,3-dicarboxylate, L-pyroglutamicacid, S-sulfo-L-cysteine, N-acetyl aspartylglutamate, N-methyl-D-aspartate (NMDA) and quisqualate. α-aminoadipate, a classical inhibitor of glutamate uptake, exhibited only low potency when tested against all three EAAT subtypes. These results of functional assays support the conclusion arrived at from structural analysis (i.e., nucleic acid and amino acid sequence analyses) that the glutamate transporter cDNAs and proteins of the invention are novel mammalian transporter species.

EXAMPLE 7

Tissue Distribution of Amino Acid Transporter Expression

The tissue distribution of mRNA corresponding to expression of the amino acid transporters disclosed herein was determined in various tissues by Northern hybridization experiments (see Sambrook et al., ibid.). The results of these experiments are shown in FIGS. 9 and 10.

A panel of tissue samples was examined by Northern hybridization analysis performed under high stringency conditions as follows. A nylon filter containing 2 µg human peripheral tissue poly(A)$^+$ RNA was obtained from Clonetech Laboratories (Palo Alto, Calif.), and a similar filter was prepared containing human brain region RNA as follows. Total RNA was isolated from human brain region tissue obtained from the Oregon Brain Repository and 20 µg/region were size-fractionated by denaturing formaldehyde agarose gel electrophoresis (see Sambrook et al., ibid.). Fractionated RNA was then transferred to a nylon filter using the Northern blot/capillary-osmotic technique. Northern hybridization of both filters was performed individually with $^{32}$P-labeled amino acid transporter-specific probes for each transporter to be analyzed. Probes were derived from amino acid transporter coding sequences and labeled using $^{32}$P-labeled dCTP by the random primer method (Boehringer-Mannheim, Indianapolis Ind.). Filters were hybridized overnight at 42° C. individually with each radiolabeled probe (at a concentration of $10^6$ cpm/mL) in a solution of 5X SSPE/50% formamide/7.5X Denhardt's solution (comprising 0.15 g/100 mL each of Ficoll, polyvinylpyrrolidone and bovine serum albumin)/2% SDS and 100 µg/mL denatured salmon-sperm DNA. Following hybridization, filters were washed twice for 30 min at room temperature in 2X SSPE/0.1% SDS and twice for 20 min at 50° C. in 0.1X SSPE/0.1% SDS. Hybridizing RNAs were visualized by autoradiography at −70° C. using intensifying screens. The filters were subsequently re-probed as described with a radiolabeled human β-actin probe (Clonetech) as a positive control.

Figure 9:
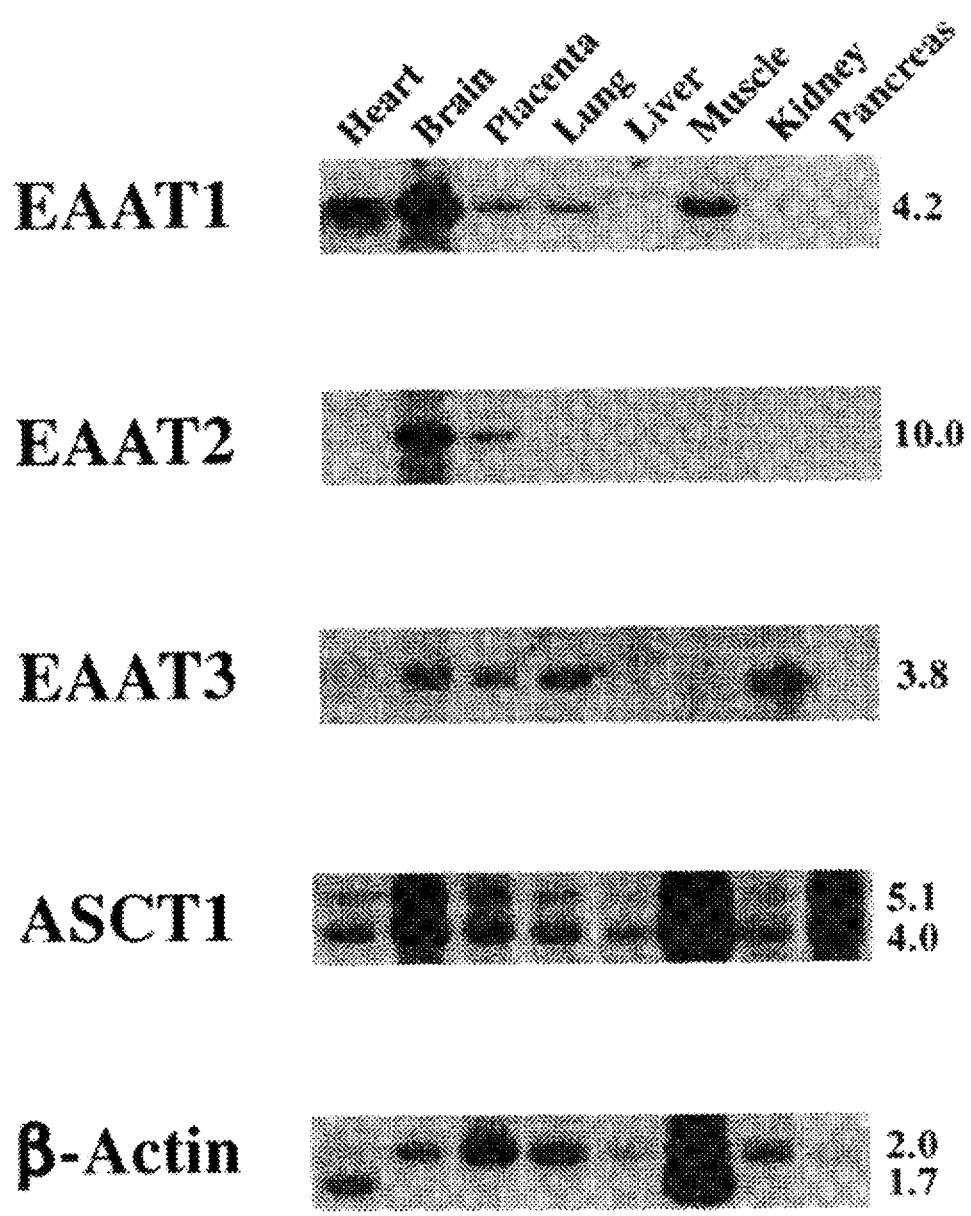
FIG. 9 shows the pattern of expression of EAAT1, EAAT2, EAAT3 and ASCT1 in human tissues; β-actin is shown as a control for amount of RNA in each lane.
Figure 10:
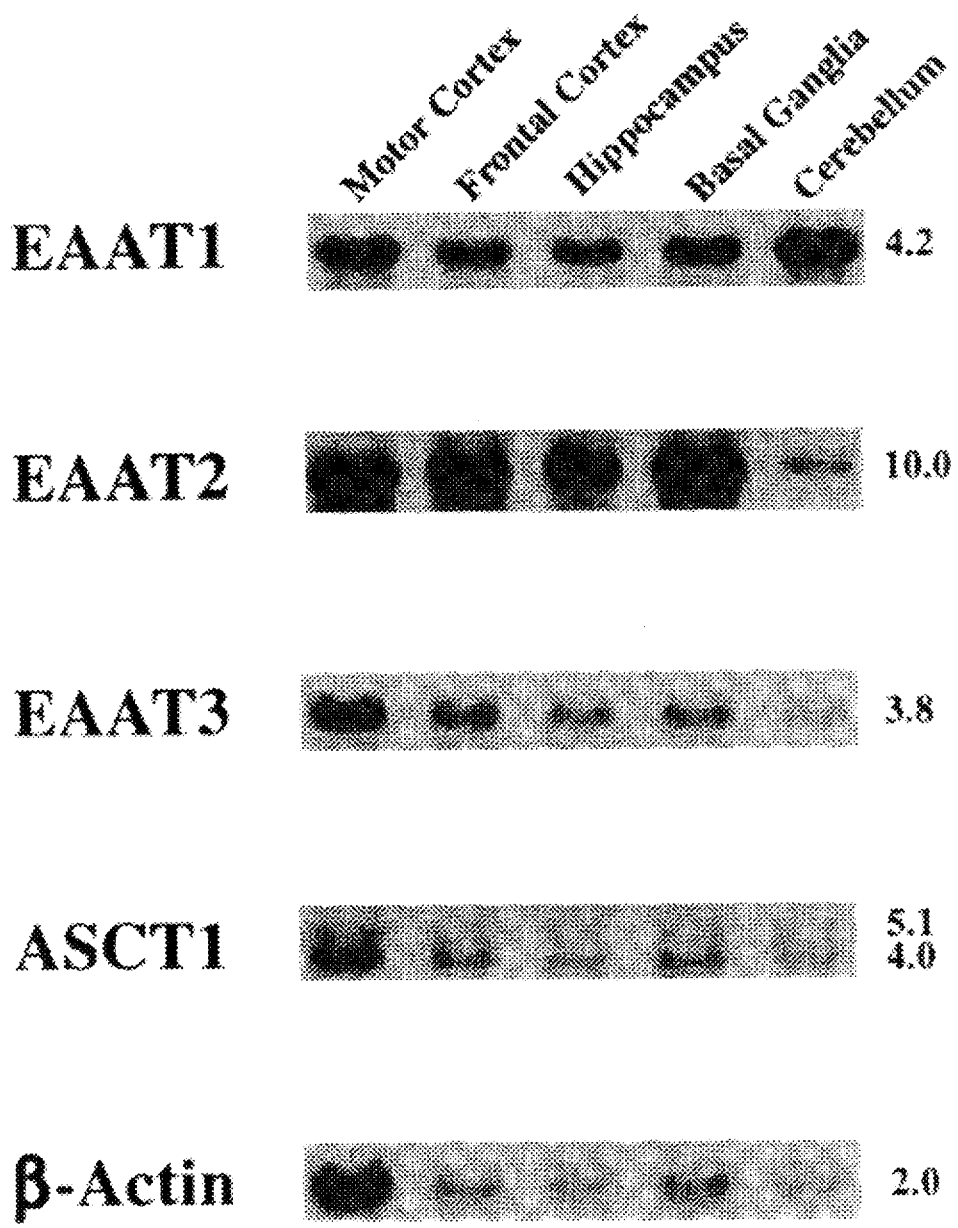
FIG. 10 shows the pattern of expression of EAAT1, EAAT2, EAAT3 and ASCT1 in human brain tissue; β-actin is shown as a control for the amount of RNA in each lane.

The results of these experiments are shown in FIGS. 9 and 10. FIG. 9 illustrates expression of each of the amino acid transporters in human heart, brain, placenta, lung, liver, muscle, kidney and pancreas. The size (in kb) of the transcripts corresponding to expression of each transporter are displayed along the right-hand border of each panel. As is seen from these autoradiographs, EAAT1 is expressed predominantly in brain, heart and muscle, to a lesser extent in placenta and lung, weakly in liver, and at levels below the ability of this assay to detect in kidney and the pancreas (if at all). EAAT2 is expressed in brain, and to a lesser extent in placenta; expression was not detected in any other tissue tested. EAAT3 is expressed predominantly in the kidney, but significant expression was also detected in brain, placenta, and lung. ASCT1 is expressed in all tissues tested as at least one of three differently-sized transcripts, possibly corresponding to differential RNA processing during expression of this transporter (which result might be due in the alternative to the utilization of alternative polyadenylation sites found in the 3' untranslated region). These results demonstrate that the amino acid transporters disclosed herein are encoded by separate and distinct, albeit related, genes and that each transporter has a unique pattern of tissue-specific expression.

FIG. 10 shows the distribution of these amino acid transporter transcripts in different human brain regions. Varying expression levels were found for each of the amino acid transporters in all brain regions examined. These results support the conclusion that the amino acid transporters of the invention may play an important role in normal brain function, and that disruption of amino acid transport by these transporter may be important determinants in organic brain dysfunction, as a result of ischemia or anoxia.

EXAMPLE 8

Construction of Vaccinia Virus-Recombinant Expression Constructs for Functional Expression of Amino Acid Transporters Using an alternative approach, the amino acid transporter proteins of the invention are expressed in human HeLa (vulval adenocarcinoma) cells via a vaccinia virus-based construct. In these experiments, each of the amino acid transporter cDNAs of the invention are excised from their respective pOTV-containing constructs and subcloned into a modified pBluescript (Strategene) vector wherein each of the amino acid transporter cDNAs described above is under the control of a bacteriophage T7 RNA polymerase promoter (as is described in Blakely et al., 1991, Anal. Biochem. 194: 302–308), termed pT7-AAT constructs. HeLa cells are first infected with a recombinant vaccinia virus, VTF-7, that expresses T7 RNA polymerase. Cells are incubated with virus at a concentration of about 10 plaque-forming unit/cell in serum-free Dulbecco's modified Eagle's medium at 37° C. for 30 min., and then the cells were transfected with each of the amino acid transporter constructs described above (i.e. the pT7-AAT constructs) using a lipofectin-mediated (Bethesda Research Labs, Gaithersburg, Md.) transfection protocol (see Felgner et al., 1987, Proc. Natl. Acad. Sci. USA 84: 7413–7417). Cells are then incubated for 12–24 h before being assayed for amino acid transporter expression as described in Example 5.

EXAMPLE 9

Construction of Fusion Proteins-Recombinant Expression Constructs for Expression of Immunologically-Active Epitopes of Amino Acid Transporters The amino acid transporter proteins of the invention are expressed as fusion proteins in bacteria to produce immunologically-active epitopes. In these experiments, each of the amino acid transporter cDNAs of the invention are excised from their respective pOTV-containing constructs and subcloned into a pGEX-2T construct (Pharmacia, Piscataway, N.J.) whereby the coding sequences of the amino acid transporter cDNAs are translationally in-frame with sequences encoding glutathione-S-transferase (described in Arriza et al., 1992, J. Neurosci. 12: 4045–4055), termed pGST-AAT constructs. After introduction of the pGST-AAT constructs into bacterial cells (*E. coli*, strain D5α) using conventional techniques (see Sambrook et al., ibid.), fusion protein expression is induced with isopropyl-1-thio-β-D-galactopyranoside as described (Smith & Johnson, 1988, Gene 67: 31–40) and are purified using glutathione-Sepharose 4B (Pharmacia). Antibodies are then raised against each of the amino acid transporters of the invention by inoculation of rabbits with 300–500 µg of purified fusion protein in Freund's adjuvant (Grand Island Biological Co., Grand Island, N.Y.), said inoculation repeated approximately every 4 weeks. Sera are immunoaffinity-purified on columns of Affi-Gel 15 derivatized with purified fusion protein. After salt elution, such antibodies are neutralized, stabilized with bovine serum albumin at a final concentration of 1 mg/mL, dialyzed against PBS and assayed by immunoblotting using conventional techniques (Harlow & Lane, 1988, *Antibodies: A Laboratory Manual*, Cold Spring Harbor Laboratory Press, Cold Spring Harbor, N.Y.).

It should be understood that the foregoing disclosure emphasizes certain specific embodiments of the invention and that all modifications or alternatives equivalent thereto are within the spirit and scope of the invention as set forth in the appended claims.

TABLE I

| Amino Acid (1 mM)* | ASCT1 RNA-injected Oocytes** | Water-injected Oocytes** |
|---|---|---|
| Alanine | 18 ± 2 | 0.6 ± 0.1 |
| Serine | 20 ± 5.1 | 0.4 ± 0.1 |
| Cysteine | 19.2 ± 5.9 | 1.0 ± 0.3 |

*n = 5;
**pmol/min per oocyte:

TABLE II

| Amino Acid* | $K_m$ (µM) | $I_{max}$** |
|---|---|---|
| Alanine | 71 ± 14 | (1.0) |
| Serine | 88 ± 11 | 1.2 ± 0.08 |
| Cysteine | 29 ± 6 | 1.0 ± 0.04 |
| Threonine | 137 ± 19 | 1.4 ± 0.03 |
| Valine | 390 ± 8 | 0.6 ± 0.11 |

NOTE:

data is expressed as the mean of at least 5 determinations ± standard error.

*All amino acids were the L-stereoisomer

**$I_{max}$ was determined by least squares fit to the equation:

$I = I_{max} \times ([S]/(K_m + [S]))$ where $I_{max}$ is the maximal current and $K_m$ is the transport constant

TABLE III

Glutamate uptake inhibition constants.

| | Ki (in µM) determined for each transporter* | | |
|---|---|---|---|
| Compound | EAAT1 | EAAT2 | EAAT3 |
| THA (L-threo-β-hydroxyaspartate) | 32 ± 8 | 19 ± 6 | 25 ± 5 |
| PDC (L-trans-pyrrolidine-2,4-dicarboxylate) | 79 ± 7 | 8 ± 2 | 61 ± 14 |
| SOS (L-Serine-O-sulfate) | 107 ± 8 | 1157 ± 275 | 150 ± 52 |
| DHK (Dihydrokainate) | >1 mM | 23 ± 6 | >1 mM |
| KAI (Kainate) | >1 mM | 59 ± 18 | >1 mM |
| L-cysteate | 10 ± 3 | 10 ± 2 | 19 ± 9 |
| L-cysteine sulfinic acid | 14 ± 7 | 6 ± 1 | 17 ± 2 |
| β-glutamate | 297 ± 118 | 156 ± 37 | 307 ± 48 |
| L-aspartate-β-hydroxymate | 369 ± 70 | 184 ± 27 | 133 ± 34 |

*Under the assay conditions used ([S]<<Km), the Ki value does not differ significantly from the measured IC50.

What we claim is:

1. An isolated nucleic acid wherein the nucleotide sequence of the nucleic acid comprises the sequence of the human excitatory amino acid transporter EAAT3 (SEQ ID No.8).

2. A nucleic acid hybridization probe for the detection of mammalian excitatory amino acid transporter-encoding nucleic acid comprising the nucleotide sequence of claim 1.

3. A recombinant expression construct comprising a nucleic acid having a nucleotide sequence encoding a mammalian excitatory amino acid transporter, wherein the nucleotide sequence of the nucleic acid comprises the sequence of the human EAAT3 excitatory amino acid transporter (SEQ ID No.8), and wherein the construct expresses the EAAT3 excitatory amino acid transporter in a transformed culture of eukaryotic or prokaryotic cells.

4. A cell culture transformed with the recombinant expression construct of claim 3.

* * * * *

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
CTGRGCRATG AARATGGCAG CCAGGGCYTC ATACAGGGCT GTGCCRTCCA TGTTRATGGT      60

RGC                                                                    63
```

( 2 ) INFORMATION FOR SEQ ID NO:2:

( i ) SEQUENCE CHARACTERISTICS:
        ( A ) LENGTH: 1680 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: 5'UTR
        ( B ) LOCATION: 1..30

( i x ) FEATURE:
        ( A ) NAME/KEY: CDS
        ( B ) LOCATION: 31..1626

( i x ) FEATURE:
        ( A ) NAME/KEY: 3'UTR
        ( B ) LOCATION: 1626..1680

( x i ) SEQUENCE DESCRIPTION: SEQ ID NO:2:

```
CACCTCTAGC TCGGAGCGGC GTGTAGCGCC ATG GAG AAG AGC AAC GAG ACC AAC         54
                                 Met Glu Lys Ser Asn Glu Thr Asn
                                  1               5

GGC TAC CTT GAC AGC GCT CAG GCG GGG CCT GCG GCC GGG CCC GGA GCT         102
Gly Tyr Leu Asp Ser Ala Gln Ala Gly Pro Ala Ala Gly Pro Gly Ala
         10              15                  20

CCG GGG ACC GCG GCG GGA CGC GCA CGG CGT TGC GCG CGC TTC CTG CGG        150
Pro Gly Thr Ala Ala Gly Arg Ala Arg Arg Cys Ala Arg Phe Leu Arg
 25              30                  35                      40

CGC CAA GCG CTG GTG CTG CTC ACC GTG TCC GGG GTG CTG GCG GGC GCG         198
Arg Gln Ala Leu Val Leu Leu Thr Val Ser Gly Val Leu Ala Gly Ala
                 45              50                  55

GGC CTG GGC GCG GCG TTG CGC GGG CTC AGC CTG AGC CGC ACG CAG GTC         246
Gly Leu Gly Ala Ala Leu Arg Gly Leu Ser Leu Ser Arg Thr Gln Val
             60                  65                  70

ACC TAC CTG GCC TTC CCC GGC GAG ATG CTG CTC CGC ATG CTG CGC ATG         294
Thr Tyr Leu Ala Phe Pro Gly Glu Met Leu Leu Arg Met Leu Arg Met
         75                  80                  85

ATC ATC CTG CCG CTG GTG GTC TGC AGC CTG GTG TCG GGC GCC GCC TCG         342
Ile Ile Leu Pro Leu Val Val Cys Ser Leu Val Ser Gly Ala Ala Ser
     90                  95                 100

CTC GAT GCC AGC TGC CTC GGG CGT CTG GGC GGC ATC CGT GTC GCC TAC         390
Leu Asp Ala Ser Cys Leu Gly Arg Leu Gly Gly Ile Arg Val Ala Tyr
105                 110                 115                 120

TTT GGC CTC ACC ACA CTG AGT GCC TCG GCG CTC GCC GTG GCC TTG GCG         438
Phe Gly Leu Thr Thr Leu Ser Ala Ser Ala Leu Ala Val Ala Leu Ala
                125                 130                 135

TTC ATC ATC AAG CCA GGA TCC GGT GCG CAG ACC CTT CAG TCC AGC GAC         486
Phe Ile Ile Lys Pro Gly Ser Gly Ala Gln Thr Leu Gln Ser Ser Asp
```

-continued

```
                    140                         145                         150
CTG GGG CTG GAG GAC TCG GGG CCT CCT CCT GTC CCC AAA GAG ACG GTG          534
Leu Gly Leu Glu Asp Ser Gly Pro Pro Pro Val Pro Lys Glu Thr Val
        155                         160                         165

GAC TCT TTC CTC GAC CTG GCC AGA AAC CTG TTT CCC TCC AAT CTT GTG          582
Asp Ser Phe Leu Asp Leu Ala Arg Asn Leu Phe Pro Ser Asn Leu Val
    170                         175                         180

GTT GCA GCT TTC CGT ACG TAT GCA ACC GAT TAT AAA GTC GTG ACC CAG          630
Val Ala Ala Phe Arg Thr Tyr Ala Thr Asp Tyr Lys Val Val Thr Gln
185                         190                         195                 200

AAC AGC AGC TCT GGA AAT GTA ACC CAT GAA AAG ATC CCC ATA GGC ACT          678
Asn Ser Ser Ser Gly Asn Val Thr His Glu Lys Ile Pro Ile Gly Thr
                    205                         210                         215

GAG ATA GAA GGG ATG AAC ATT TTA GGA TTG GTC CTG TTT GCT CTG GTG          726
Glu Ile Glu Gly Met Asn Ile Leu Gly Leu Val Leu Phe Ala Leu Val
                220                         225                         230

TTA GGA GTG GCC TTA AAG AAA CTA GGC TCC GAA GGA GAA GAC CTC ATC          774
Leu Gly Val Ala Leu Lys Lys Leu Gly Ser Glu Gly Glu Asp Leu Ile
            235                         240                         245

CGT TTC TTC AAT TCC CTC AAC GAG GCG ACG ATG GTG CTG GTG TCC TGG          822
Arg Phe Phe Asn Ser Leu Asn Glu Ala Thr Met Val Leu Val Ser Trp
    250                         255                         260

ATT ATG TGG TAC GTA CCT GTG GGC ATC ATG TTC CTT GTT GGA AGC AAG          870
Ile Met Trp Tyr Val Pro Val Gly Ile Met Phe Leu Val Gly Ser Lys
265                         270                         275                 280

ATC GTG GAA ATG AAA GAC ATC ATC GTG CTG GTG ACC AGC CTG GGG AAA          918
Ile Val Glu Met Lys Asp Ile Ile Val Leu Val Thr Ser Leu Gly Lys
                    285                         290                         295

TAC ATC TTC GCA TCT ATA TTG GGC CAT GTT ATT CAT GGA GGA ATT GTT          966
Tyr Ile Phe Ala Ser Ile Leu Gly His Val Ile His Gly Gly Ile Val
                300                         305                         310

CTG CCA CTT ATT TAT TTT GTT TTC ACA CGA AAA AAC CCA TTC AGA TTC         1014
Leu Pro Leu Ile Tyr Phe Val Phe Thr Arg Lys Asn Pro Phe Arg Phe
            315                         320                         325

CTC CTG GGC CTC CTC GCC CCA TTT GCG ACA GCA TTT GCT ACC TGC TCC         1062
Leu Leu Gly Leu Leu Ala Pro Phe Ala Thr Ala Phe Ala Thr Cys Ser
    330                         335                         340

AGC TCA GCG ACC CTT CCC TCT ATG ATG AAG TGC ATT GAA GAG AAC AAT         1110
Ser Ser Ala Thr Leu Pro Ser Met Met Lys Cys Ile Glu Glu Asn Asn
345                         350                         355                 360

GGT GTG GAC AAG AGG ATC AGC AGG TTT ATT CTC CCC ATC GGG GCC ACC         1158
Gly Val Asp Lys Arg Ile Ser Arg Phe Ile Leu Pro Ile Gly Ala Thr
                    365                         370                         375

GTG AAC ATG GAC GGA GCA GCC ATC TTC CAG TGT GTG GCC GCG GTG TTC         1206
Val Asn Met Asp Gly Ala Ala Ile Phe Gln Cys Val Ala Ala Val Phe
                380                         385                         390

ATT GCG CAA CTC AAC AAC ATA GAG CTC AAC GCA GGA CAG ATT TTC ACC         1254
Ile Ala Gln Leu Asn Asn Ile Glu Leu Asn Ala Gly Gln Ile Phe Thr
            395                         400                         405

ATT CTA GTG ACT GCC ACA GCG TCC AGT GTT GGA GCA GCA GGC GTG CCA         1302
Ile Leu Val Thr Ala Thr Ala Ser Ser Val Gly Ala Ala Gly Val Pro
    410                         415                         420

GCT GGA GGG GTC CTC ACC ATT GCC ATT ATC CTG GAG GCC ATT GGG CTG         1350
Ala Gly Gly Val Leu Thr Ile Ala Ile Ile Leu Glu Ala Ile Gly Leu
425                         430                         435                 440

CCT ACT CAT GAC CTG CCT CTG ATC CTG GCT GTG GAC TGG ATT GTG GAC         1398
Pro Thr His Asp Leu Pro Leu Ile Leu Ala Val Asp Trp Ile Val Asp
                    445                         450                         455

CGG ACC ACC ACG GTG GTG AAT GTG GAG GGG GAT GCC CTG GGT GCA GGC         1446
Arg Thr Thr Thr Val Val Asn Val Glu Gly Asp Ala Leu Gly Ala Gly
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 460 |     |     |     |     | 465 |     |     |     |     | 470 |     |      |
| ATT | CTC | CAC | CAC | CTG | AAT | CAG | AAG | GCA | ACA | AAG | AAA | GGC | GAG | CAG | GAA | 1494 |
| Ile | Leu | His | His | Leu | Asn | Gln | Lys | Ala | Thr | Lys | Lys | Gly | Glu | Gln | Glu |      |
|     |     | 475 |     |     |     |     | 480 |     |     |     |     | 485 |     |     |     |      |
| CTT | GCT | GAG | GTG | AAA | GTG | GAA | GCC | ATC | CCC | AAC | TGC | AAG | TCT | GAG | GAG | 1542 |
| Leu | Ala | Glu | Val | Lys | Val | Glu | Ala | Ile | Pro | Asn | Cys | Lys | Ser | Glu | Glu |      |
|     |     | 490 |     |     |     |     | 495 |     |     |     |     | 500 |     |     |     |      |
| GAG | ACA | TCG | CCC | CTG | GTG | ACA | CAC | CAG | AAC | CCC | GCT | GGC | CCC | GTG | GCC | 1590 |
| Glu | Thr | Ser | Pro | Leu | Val | Thr | His | Gln | Asn | Pro | Ala | Gly | Pro | Val | Ala |      |
| 505 |     |     |     |     | 510 |     |     |     |     | 515 |     |     |     |     | 520 |      |
| AGT | GCC | CCA | GAA | CTG | GAA | TCC | AAG | GAG | TCG | GTT | CTG | TGATGGGGCT |  |  |  | 1636 |
| Ser | Ala | Pro | Glu | Leu | Glu | Ser | Lys | Glu | Ser | Val | Leu |     |     |     |     |      |
|     |     |     |     | 525 |     |     |     |     | 530 |     |     |     |     |     |     |      |

GGGCTTTGGG CTTGCCTGCC AGCAGTGATG TCCCACCCTG TTCA  1680

( 2 ) INFORMATION FOR SEQ ID NO:3:

( i ) SEQUENCE CHARACTERISTICS:
        ( A ) LENGTH: 532 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

| Met | Glu | Lys | Ser | Asn | Glu | Thr | Asn | Gly | Tyr | Leu | Asp | Ser | Ala | Gln | Ala |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Gly | Pro | Ala | Ala | Gly | Pro | Gly | Ala | Pro | Gly | Thr | Ala | Ala | Gly | Arg | Ala |
|     |     |     | 20  |     |     |     | 25  |     |     |     |     | 30  |     |     |     |
| Arg | Arg | Cys | Ala | Arg | Phe | Leu | Arg | Arg | Gln | Ala | Leu | Val | Leu | Leu | Thr |
|     |     | 35  |     |     |     | 40  |     |     |     |     | 45  |     |     |     |     |
| Val | Ser | Gly | Val | Leu | Ala | Gly | Ala | Gly | Leu | Gly | Ala | Ala | Leu | Arg | Gly |
|     | 50  |     |     |     | 55  |     |     |     |     | 60  |     |     |     |     |     |
| Leu | Ser | Leu | Ser | Arg | Thr | Gln | Val | Thr | Tyr | Leu | Ala | Phe | Pro | Gly | Glu |
| 65  |     |     |     | 70  |     |     |     |     | 75  |     |     |     |     | 80  |     |
| Met | Leu | Leu | Arg | Met | Leu | Arg | Met | Ile | Ile | Leu | Pro | Leu | Val | Val | Cys |
|     |     |     |     | 85  |     |     |     | 90  |     |     |     |     | 95  |     |     |
| Ser | Leu | Val | Ser | Gly | Ala | Ala | Ser | Leu | Asp | Ala | Ser | Cys | Leu | Gly | Arg |
|     |     |     | 100 |     |     |     | 105 |     |     |     |     | 110 |     |     |     |
| Leu | Gly | Gly | Ile | Arg | Val | Ala | Tyr | Phe | Gly | Leu | Thr | Thr | Leu | Ser | Ala |
|     |     | 115 |     |     |     | 120 |     |     |     |     | 125 |     |     |     |     |
| Ser | Ala | Leu | Ala | Val | Ala | Leu | Ala | Phe | Ile | Ile | Lys | Pro | Gly | Ser | Gly |
|     | 130 |     |     |     | 135 |     |     |     |     | 140 |     |     |     |     |     |
| Ala | Gln | Thr | Leu | Gln | Ser | Ser | Asp | Leu | Gly | Leu | Glu | Asp | Ser | Gly | Pro |
| 145 |     |     |     | 150 |     |     |     |     | 155 |     |     |     |     | 160 |     |
| Pro | Pro | Val | Pro | Lys | Glu | Thr | Val | Asp | Ser | Phe | Leu | Asp | Leu | Ala | Arg |
|     |     |     | 165 |     |     |     | 170 |     |     |     |     | 175 |     |     |     |
| Asn | Leu | Phe | Pro | Ser | Asn | Leu | Val | Val | Ala | Ala | Phe | Arg | Thr | Tyr | Ala |
|     |     |     | 180 |     |     |     | 185 |     |     |     |     | 190 |     |     |     |
| Thr | Asp | Tyr | Lys | Val | Val | Thr | Gln | Asn | Ser | Ser | Ser | Gly | Asn | Val | Thr |
|     |     |     | 195 |     |     |     | 200 |     |     |     |     | 205 |     |     |     |
| His | Glu | Lys | Ile | Pro | Ile | Gly | Thr | Glu | Ile | Glu | Gly | Met | Asn | Ile | Leu |
|     |     | 210 |     |     |     | 215 |     |     |     |     | 220 |     |     |     |     |
| Gly | Leu | Val | Leu | Phe | Ala | Leu | Val | Leu | Gly | Val | Ala | Leu | Lys | Lys | Leu |
| 225 |     |     |     | 230 |     |     |     |     | 235 |     |     |     |     | 240 |     |
| Gly | Ser | Glu | Gly | Glu | Asp | Leu | Ile | Arg | Phe | Phe | Asn | Ser | Leu | Asn | Glu |
|     |     |     | 245 |     |     |     | 250 |     |     |     |     | 255 |     |     |     |

| | | | | | | | | | | | | | |
|---|---|---|---|---|---|---|---|---|---|---|---|---|---|
| Ala | Thr | Met | Val 260 | Leu | Val | Ser | Trp | Ile 265 | Met | Trp | Tyr | Val | Pro 270 | Val | Gly |
| Ile | Met | Phe 275 | Leu | Val | Gly | Ser | Lys 280 | Ile | Val | Glu | Met | Lys 285 | Asp | Ile | Ile |
| Val | Leu 290 | Val | Thr | Ser | Leu | Gly 295 | Lys | Tyr | Ile | Phe | Ala 300 | Ser | Ile | Leu | Gly |
| His 305 | Val | Ile | His | Gly | Gly 310 | Ile | Val | Leu | Pro | Leu 315 | Ile | Tyr | Phe | Val | Phe 320 |
| Thr | Arg | Lys | Asn | Pro 325 | Phe | Arg | Phe | Leu | Leu 330 | Gly | Leu | Leu | Ala | Pro 335 | Phe |
| Ala | Thr | Ala | Phe 340 | Ala | Thr | Cys | Ser | Ser 345 | Ser | Ala | Thr | Leu | Pro 350 | Ser | Met |
| Met | Lys | Cys 355 | Ile | Glu | Glu | Asn | Asn 360 | Gly | Val | Asp | Lys | Arg 365 | Ile | Ser | Arg |
| Phe | Ile 370 | Leu | Pro | Ile | Gly | Ala 375 | Thr | Val | Asn | Met | Asp 380 | Gly | Ala | Ala | Ile |
| Phe 385 | Gln | Cys | Val | Ala | Ala 390 | Val | Phe | Ile | Ala | Gln 395 | Leu | Asn | Asn | Ile | Glu 400 |
| Leu | Asn | Ala | Gly | Gln 405 | Ile | Phe | Thr | Ile | Leu 410 | Val | Thr | Ala | Thr | Ala 415 | Ser |
| Ser | Val | Gly | Ala 420 | Ala | Gly | Val | Pro | Ala 425 | Gly | Gly | Val | Leu | Thr 430 | Ile | Ala |
| Ile | Ile | Leu 435 | Glu | Ala | Ile | Gly | Leu 440 | Pro | Thr | His | Asp | Leu 445 | Pro | Leu | Ile |
| Leu | Ala 450 | Val | Asp | Trp | Ile | Val 455 | Asp | Arg | Thr | Thr | Thr 460 | Val | Val | Asn | Val |
| Glu 465 | Gly | Asp | Ala | Leu | Gly 470 | Ala | Gly | Ile | Leu | His 475 | His | Leu | Asn | Gln | Lys 480 |
| Ala | Thr | Lys | Lys | Gly 485 | Glu | Gln | Glu | Leu | Ala 490 | Glu | Val | Lys | Val 495 | Glu | Ala |
| Ile | Pro | Asn | Cys 500 | Lys | Ser | Glu | Glu | Glu 505 | Thr | Ser | Pro | Leu | Val 510 | Thr | His |
| Gln | Asn | Pro 515 | Ala | Gly | Pro | Val | Ala 520 | Ser | Ala | Pro | Glu | Leu 525 | Glu | Ser | Lys |
| Glu | Ser | Val 530 | Leu | | | | | | | | | | | | |

( 2 ) INFORMATION FOR SEQ ID NO:4:

( i ) SEQUENCE CHARACTERISTICS:
        ( A ) LENGTH: 1680 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: 5'UTR
        ( B ) LOCATION: 1..30

( i x ) FEATURE:
        ( A ) NAME/KEY: CDS
        ( B ) LOCATION: 31..1656

( i x ) FEATURE:
        ( A ) NAME/KEY: 3'UTR
        ( B ) LOCATION: 1657..1680

( x i ) SEQUENCE DESCRIPTION: SEQ ID NO:4:

AAAGAAGAGA CCCTCCTAGA AAAGTAAAAT ATG ACT AAA AGC AAT GGA GAA GAG     54

|  |  |  |  |  |  |  | Met | Thr | Lys | Ser | Asn | Gly | Glu | Glu |  |
|---|---|---|---|---|---|---|---|---|---|---|---|---|---|---|---|
|  |  |  |  |  |  |  | 1 |  |  |  | 5 |  |  |  |  |

| CCC | AAG | ATG | GGG | GGC | AGG | ATG | GAG | AGA | TTC | CAG | CAG | GGA | GTC | CGT | AAA | 102 |
|---|---|---|---|---|---|---|---|---|---|---|---|---|---|---|---|---|
| Pro | Lys | Met | Gly | Gly | Arg | Met | Glu | Arg | Phe | Gln | Gln | Gly | Val | Arg | Lys |  |
|  | 10 |  |  |  | 15 |  |  |  |  | 20 |  |  |  |  |  |  |

| CGC | ACA | CTT | TTG | GCC | AAG | AAG | AAA | GTG | CAG | AAC | ATT | ACA | AAG | GAG | GTT | 150 |
| Arg | Thr | Leu | Leu | Ala | Lys | Lys | Lys | Val | Gln | Asn | Ile | Thr | Lys | Glu | Val |  |
| 25 |  |  |  |  | 30 |  |  |  |  | 35 |  |  |  |  | 40 |  |

| GTT | AAA | AGT | TAC | CTG | TTT | CGG | AAT | GCT | TTT | GTG | CTG | CTC | ACA | GTC | ACC | 198 |
| Val | Lys | Ser | Tyr | Leu | Phe | Arg | Asn | Ala | Phe | Val | Leu | Leu | Thr | Val | Thr |  |
|  |  |  |  | 45 |  |  |  |  | 50 |  |  |  |  | 55 |  |  |

| GCT | GTC | ATT | GTG | GGT | ACA | ATC | CTT | GGA | TTT | ACC | CTC | CGA | CCA | TAC | AGA | 246 |
| Ala | Val | Ile | Val | Gly | Thr | Ile | Leu | Gly | Phe | Thr | Leu | Arg | Pro | Tyr | Arg |  |
|  |  |  | 60 |  |  |  |  | 65 |  |  |  |  | 70 |  |  |  |

| ATG | AGC | TAC | CGG | GAA | GTC | AAG | TAC | TTC | TCC | TTT | CCT | GGG | GAA | CTT | CTG | 294 |
| Met | Ser | Tyr | Arg | Glu | Val | Lys | Tyr | Phe | Ser | Phe | Pro | Gly | Glu | Leu | Leu |  |
|  |  | 75 |  |  |  |  | 80 |  |  |  |  | 85 |  |  |  |  |

| ATG | AGG | ATG | TTA | CAG | ATG | CTG | GTC | TTA | CCA | CTT | ATC | ATC | TCC | AGT | CTT | 342 |
| Met | Arg | Met | Leu | Gln | Met | Leu | Val | Leu | Pro | Leu | Ile | Ile | Ser | Ser | Leu |  |
|  |  | 90 |  |  |  |  | 95 |  |  |  |  | 100 |  |  |  |  |

| GTC | ACA | GGA | ATG | GCG | GCG | CTA | GAT | AGT | AAG | GCA | TCA | GGG | AAG | TGG | GAA | 390 |
| Val | Thr | Gly | Met | Ala | Ala | Leu | Asp | Ser | Lys | Ala | Ser | Gly | Lys | Trp | Glu |  |
| 105 |  |  |  | 110 |  |  |  |  | 115 |  |  |  |  | 120 |  |  |

| TGC | GGA | GCT | GTA | GTC | TAT | TAT | ATG | ACT | ACC | ACC | ATC | ATT | GCT | GTG | GTG | 438 |
| Cys | Gly | Ala | Val | Val | Tyr | Tyr | Met | Thr | Thr | Thr | Ile | Ile | Ala | Val | Val |  |
|  |  |  |  | 125 |  |  |  |  | 130 |  |  |  |  | 135 |  |  |

| ATT | GGC | ATA | ATC | ATT | GTC | ATC | ATC | ATC | CAT | CCT | GGG | AAG | GGC | ACA | AAG | 486 |
| Ile | Gly | Ile | Ile | Ile | Val | Ile | Ile | Ile | His | Pro | Gly | Lys | Gly | Thr | Lys |  |
|  |  |  | 140 |  |  |  |  | 145 |  |  |  |  | 150 |  |  |  |

| GAA | AAC | ATG | CAC | AGA | GAA | GGC | AAA | ATT | GTA | CGA | GTG | ACA | GCT | GCA | GAT | 534 |
| Glu | Asn | Met | His | Arg | Glu | Gly | Lys | Ile | Val | Arg | Val | Thr | Ala | Ala | Asp |  |
|  |  | 155 |  |  |  |  | 160 |  |  |  |  | 165 |  |  |  |  |

| GCC | TTC | CTG | GAC | TTG | ATC | AGG | AAC | ATG | TTA | AAT | CCA | AAT | CTG | GTA | GAA | 582 |
| Ala | Phe | Leu | Asp | Leu | Ile | Arg | Asn | Met | Leu | Asn | Pro | Asn | Leu | Val | Glu |  |
| 170 |  |  |  |  | 175 |  |  |  |  | 180 |  |  |  |  |  |  |

| GCC | TGC | TTT | AAA | CAG | TTT | AAA | ACC | AAC | TAT | GAG | AAG | AGA | AGC | TTT | AAA | 630 |
| Ala | Cys | Phe | Lys | Gln | Phe | Lys | Thr | Asn | Tyr | Glu | Lys | Arg | Ser | Phe | Lys |  |
| 185 |  |  |  |  | 190 |  |  |  |  | 195 |  |  |  |  | 200 |  |

| GTG | CCC | ATC | CAG | GCC | AAC | GAA | ACG | CTT | GTG | GGT | GCT | GTG | ATA | AAC | AAT | 678 |
| Val | Pro | Ile | Gln | Ala | Asn | Glu | Thr | Leu | Val | Gly | Ala | Val | Ile | Asn | Asn |  |
|  |  |  |  | 205 |  |  |  |  | 210 |  |  |  |  | 215 |  |  |

| GTG | TCT | GAG | GCC | ATG | GAG | ACT | CTT | ACC | CGA | ATC | ACA | GAG | GAG | CTG | GTC | 726 |
| Val | Ser | Glu | Ala | Met | Glu | Thr | Leu | Thr | Arg | Ile | Thr | Glu | Glu | Leu | Val |  |
|  |  |  |  | 220 |  |  |  |  | 225 |  |  |  |  | 230 |  |  |

| CCA | GTT | CCA | GGA | TCT | GTG | AAT | GGA | GTC | AAT | GCC | CTG | GGT | CTA | GTT | GTC | 774 |
| Pro | Val | Pro | Gly | Ser | Val | Asn | Gly | Val | Asn | Ala | Leu | Gly | Leu | Val | Val |  |
|  |  | 235 |  |  |  |  | 240 |  |  |  |  | 245 |  |  |  |  |

| TTC | TCC | ATG | TGC | TTC | GGT | TTT | GTG | ATT | GGA | AAC | ATG | AAG | GAA | CAG | GGG | 822 |
| Phe | Ser | Met | Cys | Phe | Gly | Phe | Val | Ile | Gly | Asn | Met | Lys | Glu | Gln | Gly |  |
|  |  | 250 |  |  |  |  | 255 |  |  |  |  | 260 |  |  |  |  |

| CAG | GCC | CTG | AGA | GAG | TTC | TTT | GAT | TCT | CTT | AAC | GAA | GCC | ATC | ATG | AGA | 870 |
| Gln | Ala | Leu | Arg | Glu | Phe | Phe | Asp | Ser | Leu | Asn | Glu | Ala | Ile | Met | Arg |  |
| 265 |  |  |  |  | 270 |  |  |  |  | 275 |  |  |  |  | 280 |  |

| CTG | GTA | GCA | GTA | ATA | ATG | TGG | TAT | GCC | CCC | GTG | GGT | ATT | CTC | TTC | CTG | 918 |
| Leu | Val | Ala | Val | Ile | Met | Trp | Tyr | Ala | Pro | Val | Gly | Ile | Leu | Phe | Leu |  |
|  |  |  |  | 285 |  |  |  |  | 290 |  |  |  |  | 295 |  |  |

| ATT | GCT | GGG | AAG | ATT | GTG | GAG | ATG | GAA | GAC | ATG | GGT | GTG | ATT | GGG | GGG | 966 |
| Ile | Ala | Gly | Lys | Ile | Val | Glu | Met | Glu | Asp | Met | Gly | Val | Ile | Gly | Gly |  |
|  |  |  | 300 |  |  |  |  | 305 |  |  |  |  | 310 |  |  |  |

| CAG | CTT | GCC | ATG | TAC | ACC | GTG | ACT | GTC | ATT | GTT | GGC | TTA | CTC | ATT | CAC | 1014 |

```
Gln Leu Ala Met Tyr Thr Val Thr Val Ile Val Gly Leu Leu Ile His
        315             320             325

GCA GTC ATC GTC TTG CCA CTC CTC TAC TTC TTG GTA ACA CGG AAA AAC        1062
Ala Val Ile Val Leu Pro Leu Leu Tyr Phe Leu Val Thr Arg Lys Asn
        330             335             340

CCT TGG GTT TTT ATT GGA GGG TTG CTG CAA GCA CTC ATC ACC GCT CTG        1110
Pro Trp Val Phe Ile Gly Gly Leu Leu Gln Ala Leu Ile Thr Ala Leu
345             350             355             360

GGG ACC TCT TCA AGT TCT GCC ACC CTA CCC ATC ACC TTC AAG TGC CTG        1158
Gly Thr Ser Ser Ser Ser Ala Thr Leu Pro Ile Thr Phe Lys Cys Leu
        365             370             375

GAA GAG AAC AAT GGC GTG GAC AAG CGC GTC ACC AGA TTC GTG CTC CCC        1206
Glu Glu Asn Asn Gly Val Asp Lys Arg Val Thr Arg Phe Val Leu Pro
        380             385             390

GTA GGA GCC ACC ATT AAC ATG GAT GGG ACT GCC CTC TAT GAG GCT TTG        1254
Val Gly Ala Thr Ile Asn Met Asp Gly Thr Ala Leu Tyr Glu Ala Leu
        395             400             405

GCT GCC ATT TTC ATT GCT CAA GTT AAC AAC TTT GAA CTG AAC TTC GGA        1302
Ala Ala Ile Phe Ile Ala Gln Val Asn Asn Phe Glu Leu Asn Phe Gly
        410             415             420

CAA ATT ATT ACA ATC AGC ATC ACA GCC ACA GCT GCC AGT ATT GGG GCA        1350
Gln Ile Ile Thr Ile Ser Ile Thr Ala Thr Ala Ala Ser Ile Gly Ala
425             430             435             440

GCT GGA ATT CCT CAG GCG GGC CTG GTC ACT ATG GTC ATT GTG CTG ACA        1398
Ala Gly Ile Pro Gln Ala Gly Leu Val Thr Met Val Ile Val Leu Thr
            445             450             455

TCT GTC GGC CTG CCC ACT GAC GAC ATC ACG CTC ATC ATC GCG GTG GAC        1446
Ser Val Gly Leu Pro Thr Asp Asp Ile Thr Leu Ile Ile Ala Val Asp
            460             465             470

TGG TTC TTG GAT CGC CTC CGG ACC ACC ACC AAC GTA CTG GGA GAC TCC        1494
Trp Phe Leu Asp Arg Leu Arg Thr Thr Thr Asn Val Leu Gly Asp Ser
        475             480             485

CTG GGA GCT GGG ATT GTG GAG CAC TTG TCA CGA CAT GAA CTG AAG AAC        1542
Leu Gly Ala Gly Ile Val Glu His Leu Ser Arg His Glu Leu Lys Asn
490             495             500

AGA GAT GTT GAA ATG GGT AAC TCA GTG ATT GAA GAG AAT GAA ATG AAG        1590
Arg Asp Val Glu Met Gly Asn Ser Val Ile Glu Glu Asn Glu Met Lys
505             510             515             520

AAA CCA TAT CAA CTG ATT GCA CAG GAC AAT GAA ACT GAG AAA CCC ATC        1638
Lys Pro Tyr Gln Leu Ile Ala Gln Asp Asn Glu Thr Glu Lys Pro Ile
            525             530             535

GAC AGT GAA ACC AAG ATG TAGACTAACA TAAAGAAACA CTTT                      1680
Asp Ser Glu Thr Lys Met
            540
```

( 2 ) INFORMATION FOR SEQ ID NO:5:

( i ) SEQUENCE CHARACTERISTICS:
        ( A ) LENGTH: 542 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Met Thr Lys Ser Asn Gly Glu Glu Pro Lys Met Gly Gly Arg Met Glu
1               5               10              15

Arg Phe Gln Gln Gly Val Arg Lys Arg Thr Leu Leu Ala Lys Lys Lys
            20              25              30

Val Gln Asn Ile Thr Lys Glu Val Val Lys Ser Tyr Leu Phe Arg Asn
        35              40              45
```

-continued

```
Ala Phe Val Leu Leu Thr Val Thr Ala Val Ile Val Gly Thr Ile Leu
     50                  55                  60
Gly Phe Thr Leu Arg Pro Tyr Arg Met Ser Tyr Arg Glu Val Lys Tyr
 65                  70                  75                   80
Phe Ser Phe Pro Gly Glu Leu Leu Met Arg Met Leu Gln Met Leu Val
                 85                  90                  95
Leu Pro Leu Ile Ile Ser Ser Leu Val Thr Gly Met Ala Ala Leu Asp
                100                 105                 110
Ser Lys Ala Ser Gly Lys Trp Glu Cys Gly Ala Val Val Tyr Tyr Met
            115                 120                 125
Thr Thr Thr Ile Ile Ala Val Val Ile Gly Ile Ile Ile Val Ile Ile
    130                 135                 140
Ile His Pro Gly Lys Gly Thr Lys Glu Asn Met His Arg Glu Gly Lys
145                 150                 155                 160
Ile Val Arg Val Thr Ala Ala Asp Ala Phe Leu Asp Leu Ile Arg Asn
                165                 170                 175
Met Leu Asn Pro Asn Leu Val Glu Ala Cys Phe Lys Gln Phe Lys Thr
                180                 185                 190
Asn Tyr Glu Lys Arg Ser Phe Lys Val Pro Ile Gln Ala Asn Glu Thr
            195                 200                 205
Leu Val Gly Ala Val Ile Asn Asn Val Ser Glu Ala Met Glu Thr Leu
    210                 215                 220
Thr Arg Ile Thr Glu Glu Leu Val Pro Val Pro Gly Ser Val Asn Gly
225                 230                 235                 240
Val Asn Ala Leu Gly Leu Val Val Phe Ser Met Cys Phe Gly Phe Val
                245                 250                 255
Ile Gly Asn Met Lys Glu Gln Gly Gln Ala Leu Arg Glu Phe Phe Asp
            260                 265                 270
Ser Leu Asn Glu Ala Ile Met Arg Leu Val Ala Val Ile Met Trp Tyr
    275                 280                 285
Ala Pro Val Gly Ile Leu Phe Leu Ile Ala Gly Lys Ile Val Glu Met
290                 295                 300
Glu Asp Met Gly Val Ile Gly Gly Gln Leu Ala Met Tyr Thr Val Thr
305                 310                 315                 320
Val Ile Val Gly Leu Leu Ile His Ala Val Ile Val Leu Pro Leu Leu
                325                 330                 335
Tyr Phe Leu Val Thr Arg Lys Asn Pro Trp Val Phe Ile Gly Gly Leu
            340                 345                 350
Leu Gln Ala Leu Ile Thr Ala Leu Gly Thr Ser Ser Ser Ala Thr
    355                 360                 365
Leu Pro Ile Thr Phe Lys Cys Leu Glu Glu Asn Asn Gly Val Asp Lys
370                 375                 380
Arg Val Thr Arg Phe Val Leu Pro Val Gly Ala Thr Ile Asn Met Asp
385                 390                 395                 400
Gly Thr Ala Leu Tyr Glu Ala Leu Ala Ala Ile Phe Ile Ala Gln Val
                405                 410                 415
Asn Asn Phe Glu Leu Asn Phe Gly Gln Ile Ile Thr Ile Ser Ile Thr
            420                 425                 430
Ala Thr Ala Ala Ser Ile Gly Ala Ala Gly Ile Pro Gln Ala Gly Leu
    435                 440                 445
Val Thr Met Val Ile Val Leu Thr Ser Val Gly Leu Pro Thr Asp Asp
450                 455                 460
Ile Thr Leu Ile Ile Ala Val Asp Trp Phe Leu Asp Arg Leu Arg Thr
465                 470                 475                 480
```

```
Thr Thr Asn Val Leu Gly Asp Ser Leu Gly Ala Gly Ile Val Glu His
        485             490                     495

Leu Ser Arg His Glu Leu Lys Asn Arg Asp Val Glu Met Gly Asn Ser
            500                 505                 510

Val Ile Glu Glu Asn Glu Met Lys Lys Pro Tyr Gln Leu Ile Ala Gln
        515             520                     525

Asp Asn Glu Thr Glu Lys Pro Ile Asp Ser Glu Thr Lys Met
        530             535                 540
```

( 2 ) INFORMATION FOR SEQ ID NO:6:

( i ) SEQUENCE CHARACTERISTICS:
        ( A ) LENGTH: 1800 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: 5'UTR
        ( B ) LOCATION: 1..33

( i x ) FEATURE:
        ( A ) NAME/KEY: CDS
        ( B ) LOCATION: 34..1755

( i x ) FEATURE:
        ( A ) NAME/KEY: 3'UTR
        ( B ) LOCATION: 1756..1800

( x i ) SEQUENCE DESCRIPTION: SEQ ID NO:6:

```
GATAGTGCTG AAGAGGAGGG GCGTTCCCAG ACC ATG GCA TCT ACG GAA GGT GCC    54
                                    Met Ala Ser Thr Glu Gly Ala
                                     1               5

AAC AAT ATG CCC AAG CAG GTG GAA GTG CGA ATG CCA GAC AGT CAT CTT   102
Asn Asn Met Pro Lys Gln Val Glu Val Arg Met Pro Asp Ser His Leu
         10              15                  20

GGC TCA GAG GAA CCC AAG CAC CGG CAC CTG GGC CTG CGC CTG TGT GAC   150
Gly Ser Glu Glu Pro Lys His Arg His Leu Gly Leu Arg Leu Cys Asp
     25              30                  35

AAG CTG GGG AAG AAT CTG CTC ACC CTG ACG GTG TTT GGT GTC ATC       198
Lys Leu Gly Lys Asn Leu Leu Leu Thr Leu Thr Val Phe Gly Val Ile
 40              45                  50                      55

CTG GGA GCA GTG TGT GGA GGG CTT CTT CGC TTG GCA TCT CCC ATC CAC   246
Leu Gly Ala Val Cys Gly Gly Leu Leu Arg Leu Ala Ser Pro Ile His
                 60                  65                  70

CCT GAT GTG GTT ATG TTA ATA GCC TTC CCA GGG GAT ATA CTC ATG AGG   294
Pro Asp Val Val Met Leu Ile Ala Phe Pro Gly Asp Ile Leu Met Arg
             75                  80                  85

ATG CTA AAA ATG CTC ATT CTG GGT CTA ATC ATC TCC AGC TTA ATC ACA   342
Met Leu Lys Met Leu Ile Leu Gly Leu Ile Ile Ser Ser Leu Ile Thr
         90                  95                 100

GGG TTG TCA GGC CTG GAT GCT AAG GCT AGT GGC CGC TTG GGC ACG AGA   390
Gly Leu Ser Gly Leu Asp Ala Lys Ala Ser Gly Arg Leu Gly Thr Arg
        105                 110                 115

GCC ATG GTG TAT TAC ATG TCC ACG ACC ATC ATT GCT GCA GTA CTG GGG   438
Ala Met Val Tyr Tyr Met Ser Thr Thr Ile Ile Ala Ala Val Leu Gly
120                 125                 130                 135

GTC ATT CTG GTC TTG GCT ATC CAT CCA GGC AAT CCC AAG CTC AAG AAG   486
Val Ile Leu Val Leu Ala Ile His Pro Gly Asn Pro Lys Leu Lys Lys
                140                 145                 150

CAG CTG GGG CCT GGG AAG AAG AAT GAT GAA GTG TCC AGC CTG GAT GCC   534
Gln Leu Gly Pro Gly Lys Lys Asn Asp Glu Val Ser Ser Leu Asp Ala
```

| | | | | | | | | | | | | | | | | |
|---|---|---|---|---|---|---|---|---|---|---|---|---|---|---|---|---|
| TTC | CTG | GAC | CTT | ATT | CGA | AAT | CTC | TTC | CCT | GAA | AAC | CTT | GTC | CAA | GCC | 582 |
| Phe | Leu | Asp | Leu | Ile | Arg | Asn | Leu | Phe | Pro | Glu | Asn | Leu | Val | Gln | Ala | |
| | | 170 | | | | | 175 | | | | | 180 | | | | |
| TGC | TTT | CAA | CAG | ATT | CAA | ACA | GTG | ACG | AAG | AAA | GTC | CTG | GTT | GCA | CCA | 630 |
| Cys | Phe | Gln | Gln | Ile | Gln | Thr | Val | Thr | Lys | Lys | Val | Leu | Val | Ala | Pro | |
| | 185 | | | | | 190 | | | | | 195 | | | | | |
| CCG | CCA | GAC | GAG | GAG | GCC | AAC | GCA | ACC | AGC | GCT | GAA | GTC | TCT | CTG | TTG | 678 |
| Pro | Pro | Asp | Glu | Glu | Ala | Asn | Ala | Thr | Ser | Ala | Glu | Val | Ser | Leu | Leu | |
| 200 | | | | | 205 | | | | | 210 | | | | | 215 | |
| AAC | GAG | ACT | GTG | ACT | GAG | GTG | CCG | GAG | GAG | ACT | AAG | ATG | GTT | ATC | AAG | 726 |
| Asn | Glu | Thr | Val | Thr | Glu | Val | Pro | Glu | Glu | Thr | Lys | Met | Val | Ile | Lys | |
| | | | | 220 | | | | | 225 | | | | | 230 | | |
| AAG | GGC | CTG | GAG | TTC | AAG | GAT | GGG | ATG | AAC | GTC | TTA | GGT | CTG | ATA | GGG | 774 |
| Lys | Gly | Leu | Glu | Phe | Lys | Asp | Gly | Met | Asn | Val | Leu | Gly | Leu | Ile | Gly | |
| | | | 235 | | | | | 240 | | | | | 245 | | | |
| TTT | TTC | ATT | GCT | TTT | GGC | ATC | GCT | ATG | GGG | AAG | ATG | GGA | GAT | CAG | GCC | 822 |
| Phe | Phe | Ile | Ala | Phe | Gly | Ile | Ala | Met | Gly | Lys | Met | Gly | Asp | Gln | Ala | |
| | | 250 | | | | | 255 | | | | | 260 | | | | |
| AAG | CTG | ATG | GTG | GAT | TTC | TTC | AAC | ATT | TTG | AAT | GAG | ATT | GTA | ATG | AAG | 870 |
| Lys | Leu | Met | Val | Asp | Phe | Phe | Asn | Ile | Leu | Asn | Glu | Ile | Val | Met | Lys | |
| | 265 | | | | | 270 | | | | | 275 | | | | | |
| TTA | GTG | ATC | ATG | ATC | ATG | TGG | TAC | TCT | CCC | CTG | GGT | ATC | GCC | TGC | CTG | 918 |
| Leu | Val | Ile | Met | Ile | Met | Trp | Tyr | Ser | Pro | Leu | Gly | Ile | Ala | Cys | Leu | |
| 280 | | | | | 285 | | | | | 290 | | | | | 295 | |
| ATC | TGT | GGA | AAG | ATC | ATT | GCA | ATC | AAG | GAC | TTA | GAA | GTG | GTT | GCT | AGG | 966 |
| Ile | Cys | Gly | Lys | Ile | Ile | Ala | Ile | Lys | Asp | Leu | Glu | Val | Val | Ala | Arg | |
| | | | | 300 | | | | | 305 | | | | | 310 | | |
| CAA | CTG | GGG | ATG | TAC | ATG | GTA | ACA | GTG | ATC | ATA | GGC | CTC | ATC | ATC | CAC | 1014 |
| Gln | Leu | Gly | Met | Tyr | Met | Val | Thr | Val | Ile | Ile | Gly | Leu | Ile | Ile | His | |
| | | 315 | | | | | 320 | | | | | 325 | | | | |
| GGG | GGC | ATC | TTT | CTC | CCC | TTG | ATT | TAC | TTT | GTA | GTG | ACC | AGG | AAA | AAC | 1062 |
| Gly | Gly | Ile | Phe | Leu | Pro | Leu | Ile | Tyr | Phe | Val | Val | Thr | Arg | Lys | Asn | |
| | | 330 | | | | | 335 | | | | | 340 | | | | |
| CCC | TTC | TCC | CTT | TTT | GCT | GGC | ATT | TTC | CAA | GCT | TGG | ATC | ACT | GCC | CTG | 1110 |
| Pro | Phe | Ser | Leu | Phe | Ala | Gly | Ile | Phe | Gln | Ala | Trp | Ile | Thr | Ala | Leu | |
| | 345 | | | | | 350 | | | | | 355 | | | | | |
| GGC | ACC | GCT | TCC | AGT | GCT | GGA | ACT | TTG | CCT | GTC | ACC | TTT | CGT | TGC | CTG | 1158 |
| Gly | Thr | Ala | Ser | Ser | Ala | Gly | Thr | Leu | Pro | Val | Thr | Phe | Arg | Cys | Leu | |
| 360 | | | | | 365 | | | | | 370 | | | | | 375 | |
| GAA | GAA | AAT | CTG | GGG | ATT | GAT | AAG | CGT | GTG | ACT | AGA | TTC | GTC | CTT | CCT | 1206 |
| Glu | Glu | Asn | Leu | Gly | Ile | Asp | Lys | Arg | Val | Thr | Arg | Phe | Val | Leu | Pro | |
| | | | | 380 | | | | | 385 | | | | | 390 | | |
| GTT | GGA | GCA | ACC | ATT | AAC | ATG | GAT | GGT | ACA | GCC | CTT | TAT | GAA | GCG | GTG | 1254 |
| Val | Gly | Ala | Thr | Ile | Asn | Met | Asp | Gly | Thr | Ala | Leu | Tyr | Glu | Ala | Val | |
| | | | | 395 | | | | | 400 | | | | | 405 | | |
| GCC | GCC | ATC | TTT | ATA | GCC | CAA | ATG | AAT | GGT | GTT | GTC | CTG | GAT | GGA | GGA | 1302 |
| Ala | Ala | Ile | Phe | Ile | Ala | Gln | Met | Asn | Gly | Val | Val | Leu | Asp | Gly | Gly | |
| | | 410 | | | | | 415 | | | | | 420 | | | | |
| CAG | ATT | GTG | ACT | GTA | AGC | CTC | ACA | GCC | ACC | CTG | GCA | AGC | GTC | GGC | GCG | 1350 |
| Gln | Ile | Val | Thr | Val | Ser | Leu | Thr | Ala | Thr | Leu | Ala | Ser | Val | Gly | Ala | |
| | 425 | | | | | 430 | | | | | 435 | | | | | |
| GCC | AGT | ATC | CCC | AGT | GCC | GGG | CTG | GTC | ACC | ATG | CTC | CTC | ATT | CTG | ACA | 1398 |
| Ala | Ser | Ile | Pro | Ser | Ala | Gly | Leu | Val | Thr | Met | Leu | Leu | Ile | Leu | Thr | |
| 440 | | | | | 445 | | | | | 450 | | | | | 455 | |
| GCC | GTG | GGC | CTG | CCA | ACA | GAG | GAC | ATC | AGC | TTG | CTG | GTG | GCT | GTG | GAC | 1446 |
| Ala | Val | Gly | Leu | Pro | Thr | Glu | Asp | Ile | Ser | Leu | Leu | Val | Ala | Val | Asp | |
| | | | | 460 | | | | | 465 | | | | | 470 | | |
| TGG | CTG | CTG | GAC | AGG | ATG | AGA | ACT | TCA | GTC | AAT | GTT | GTG | GGT | GAC | TCT | 1494 |
| Trp | Leu | Leu | Asp | Arg | Met | Arg | Thr | Ser | Val | Asn | Val | Val | Gly | Asp | Ser | |

```
                          475                         480                         485
    TTT  GGG  GCT  GGG  ATA  GTC  TAT  CAC  CTC  TCC  AAG  TCT  GAG  CTG  GAT  ACC       1542
    Phe  Gly  Ala  Gly  Ile  Val  Tyr  His  Leu  Ser  Lys  Ser  Glu  Leu  Asp  Thr
              490                      495                 500

ATT  GAC  TCC  CAG  CAT  CGA  GTG  CAT  GAA  GAT  ATT  GAA  ATG  ACC  AAG  ACT       1590
    Ile  Asp  Ser  Gln  His  Arg  Val  His  Glu  Asp  Ile  Glu  Met  Thr  Lys  Thr
    505                      510                           515

CAA  TCC  ATT  TAT  GAT  GAC  ATG  AAG  AAC  CAC  AGG  GAA  AGC  AAC  TCT  AAT       1638
    Gln  Ser  Ile  Tyr  Asp  Asp  Met  Lys  Asn  His  Arg  Glu  Ser  Asn  Ser  Asn
    520                      525                      530                           535

CAA  TGT  GTC  TAT  GCT  GCA  CAC  AAC  TCT  GTC  ATA  GTA  GAT  GAA  TGC  AAG       1686
    Gln  Cys  Val  Tyr  Ala  Ala  His  Asn  Ser  Val  Ile  Val  Asp  Glu  Cys  Lys
                        540                 545                      550

GTA  ACT  CTG  GCA  GCC  AAT  GGA  AAG  TCA  GCC  GAC  TGC  AGT  GTT  GAG  GAA       1734
    Val  Thr  Leu  Ala  Ala  Asn  Gly  Lys  Ser  Ala  Asp  Cys  Ser  Val  Glu  Glu
                        555                 560                      565

GAA  CCT  TGG  AAA  CGT  GAG  AAA  TAAGGATATG AGTCTCAGCA AATTCTTGAA                   1785
    Glu  Pro  Trp  Lys  Arg  Glu  Lys
              570

TAAACTCCCC AGCGT                                                                      1800
```

( 2 ) INFORMATION FOR SEQ ID NO:7:

( i ) SEQUENCE CHARACTERISTICS:
        ( A ) LENGTH: 574 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Met  Ala  Ser  Thr  Glu  Gly  Ala  Asn  Asn  Met  Pro  Lys  Gln  Val  Glu  Val
 1                   5                   10                       15

Arg  Met  Pro  Asp  Ser  His  Leu  Gly  Ser  Glu  Glu  Pro  Lys  His  Arg  His
               20                       25                      30

Leu  Gly  Leu  Arg  Leu  Cys  Asp  Lys  Leu  Gly  Lys  Asn  Leu  Leu  Leu  Thr
          35                       40                      45

Leu  Thr  Val  Phe  Gly  Val  Ile  Leu  Gly  Ala  Val  Cys  Gly  Gly  Leu  Leu
     50                       55                      60

Arg  Leu  Ala  Ser  Pro  Ile  His  Pro  Asp  Val  Val  Met  Leu  Ile  Ala  Phe
65                       70                       75                           80

Pro  Gly  Asp  Ile  Leu  Met  Arg  Met  Leu  Lys  Met  Leu  Ile  Leu  Gly  Leu
                    85                       90                      95

Ile  Ile  Ser  Ser  Leu  Ile  Thr  Gly  Leu  Ser  Gly  Leu  Asp  Ala  Lys  Ala
               100                      105                     110

Ser  Gly  Arg  Leu  Gly  Thr  Arg  Ala  Met  Val  Tyr  Tyr  Met  Ser  Thr  Thr
          115                      120                     125

Ile  Ile  Ala  Ala  Val  Leu  Gly  Val  Ile  Leu  Val  Leu  Ala  Ile  His  Pro
     130                     135                     140

Gly  Asn  Pro  Lys  Leu  Lys  Lys  Gln  Leu  Gly  Pro  Gly  Lys  Lys  Asn  Asp
145                      150                      155                         160

Glu  Val  Ser  Ser  Leu  Asp  Ala  Phe  Leu  Asp  Leu  Ile  Arg  Asn  Leu  Phe
                    165                      170                     175

Pro  Glu  Asn  Leu  Val  Gln  Ala  Cys  Phe  Gln  Gln  Ile  Gln  Thr  Val  Thr
               180                      185                     190

Lys  Lys  Val  Leu  Val  Ala  Pro  Pro  Asp  Glu  Glu  Ala  Asn  Ala  Thr
          195                      200                     205

Ser  Ala  Glu  Val  Ser  Leu  Leu  Asn  Glu  Thr  Val  Thr  Glu  Val  Pro  Glu
```

|   |   |   |   |   | 210 |   |   |   |   | 215 |   |   |   |   | 220 |   |   |   |
|---|---|---|---|---|---|---|---|---|---|---|---|---|---|---|---|---|---|---|
| Glu | Thr | Lys | Met | Val | Ile | Lys | Lys | Gly | Leu | Glu | Phe | Lys | Asp | Gly | Met |
| 225 |   |   |   |   | 230 |   |   |   | 235 |   |   |   |   | 240 |
| Asn | Val | Leu | Gly | Leu | Ile | Gly | Phe | Phe | Ile | Ala | Phe | Gly | Ile | Ala | Met |
|   |   |   |   | 245 |   |   |   | 250 |   |   |   |   | 255 |
| Gly | Lys | Met | Gly | Asp | Gln | Ala | Lys | Leu | Met | Val | Asp | Phe | Phe | Asn | Ile |
|   |   |   | 260 |   |   |   | 265 |   |   |   |   | 270 |
| Leu | Asn | Glu | Ile | Val | Met | Lys | Leu | Val | Ile | Met | Ile | Met | Trp | Tyr | Ser |
|   |   | 275 |   |   |   | 280 |   |   |   | 285 |
| Pro | Leu | Gly | Ile | Ala | Cys | Leu | Ile | Cys | Gly | Lys | Ile | Ile | Ala | Ile | Lys |
|   | 290 |   |   |   | 295 |   |   |   | 300 |
| Asp | Leu | Glu | Val | Val | Ala | Arg | Gln | Leu | Gly | Met | Tyr | Met | Val | Thr | Val |
| 305 |   |   |   |   | 310 |   |   |   | 315 |   |   |   |   | 320 |
| Ile | Ile | Gly | Leu | Ile | Ile | His | Gly | Gly | Ile | Phe | Leu | Pro | Leu | Ile | Tyr |
|   |   |   |   | 325 |   |   |   | 330 |   |   |   |   | 335 |
| Phe | Val | Val | Thr | Arg | Lys | Asn | Pro | Phe | Ser | Leu | Phe | Ala | Gly | Ile | Phe |
|   |   |   | 340 |   |   |   | 345 |   |   |   | 350 |
| Gln | Ala | Trp | Ile | Thr | Ala | Leu | Gly | Thr | Ala | Ser | Ser | Ala | Gly | Thr | Leu |
|   |   | 355 |   |   |   | 360 |   |   |   | 365 |
| Pro | Val | Thr | Phe | Arg | Cys | Leu | Glu | Glu | Asn | Leu | Gly | Ile | Asp | Lys | Arg |
|   | 370 |   |   |   | 375 |   |   |   | 380 |
| Val | Thr | Arg | Phe | Val | Leu | Pro | Val | Gly | Ala | Thr | Ile | Asn | Met | Asp | Gly |
| 385 |   |   |   |   | 390 |   |   |   | 395 |   |   |   |   | 400 |
| Thr | Ala | Leu | Tyr | Glu | Ala | Val | Ala | Ala | Ile | Phe | Ile | Ala | Gln | Met | Asn |
|   |   |   | 405 |   |   |   | 410 |   |   |   | 415 |
| Gly | Val | Val | Leu | Asp | Gly | Gly | Gln | Ile | Val | Thr | Val | Ser | Leu | Thr | Ala |
|   |   |   | 420 |   |   |   | 425 |   |   |   | 430 |
| Thr | Leu | Ala | Ser | Val | Gly | Ala | Ala | Ser | Ile | Pro | Ser | Ala | Gly | Leu | Val |
|   |   | 435 |   |   |   | 440 |   |   |   | 445 |
| Thr | Met | Leu | Leu | Ile | Leu | Thr | Ala | Val | Gly | Leu | Pro | Thr | Glu | Asp | Ile |
|   | 450 |   |   |   | 455 |   |   |   | 460 |
| Ser | Leu | Leu | Val | Ala | Val | Asp | Trp | Leu | Leu | Asp | Arg | Met | Arg | Thr | Ser |
| 465 |   |   |   | 470 |   |   |   | 475 |   |   |   | 480 |
| Val | Asn | Val | Val | Gly | Asp | Ser | Phe | Gly | Ala | Gly | Ile | Val | Tyr | His | Leu |
|   |   |   | 485 |   |   |   | 490 |   |   |   | 495 |
| Ser | Lys | Ser | Glu | Leu | Asp | Thr | Ile | Asp | Ser | Gln | His | Arg | Val | His | Glu |
|   |   |   | 500 |   |   |   | 505 |   |   |   | 510 |
| Asp | Ile | Glu | Met | Thr | Lys | Thr | Gln | Ser | Ile | Tyr | Asp | Asp | Met | Lys | Asn |
|   |   | 515 |   |   |   | 520 |   |   |   | 525 |
| His | Arg | Glu | Ser | Asn | Ser | Asn | Gln | Cys | Val | Tyr | Ala | Ala | His | Asn | Ser |
|   | 530 |   |   |   | 535 |   |   |   | 540 |
| Val | Ile | Val | Asp | Glu | Cys | Lys | Val | Thr | Leu | Ala | Ala | Asn | Gly | Lys | Ser |
| 545 |   |   |   | 550 |   |   |   | 555 |   |   |   | 560 |
| Ala | Asp | Cys | Ser | Val | Glu | Glu | Glu | Pro | Trp | Lys | Arg | Glu | Lys |
|   |   |   | 565 |   |   |   | 570 |

(2) INFORMATION FOR SEQ ID NO:8:

(i) SEQUENCE CHARACTERISTICS:
        (A) LENGTH: 1674 base pairs
        (B) TYPE: nucleic acid
        (C) STRANDEDNESS: single
        (D) TOPOLOGY: linear (ii) MOLECULE TYPE: cDNA (ix) FEATURE:

(A) NAME/KEY: 5'UTR
(B) LOCATION: 1..15

(ix) FEATURE:
(A) NAME/KEY: CDS
(B) LOCATION: 16..1590

(ix) FEATURE:
(A) NAME/KEY: 3'UTR
(B) LOCATION: 1591..1674

(xi) SEQUENCE DESCRIPTION: SEQ ID NO:8:

| | | | | | | | | | | | | | | | | |
|---|---|---|---|---|---|---|---|---|---|---|---|---|---|---|---|---|
| ATAGCGGCGA | CAGCC | ATG | GGG | AAA | CCG | GCG | AGG | AAA | GGA | TGC | CCG | AGT | TGG | | | 51 |
| | | Met | Gly | Lys | Pro | Ala | Arg | Lys | Gly | Cys | Pro | Ser | Trp | | | |
| | | 1 | | 5 | | | | | | 10 | | | | | | |

| AAG | CGC | TTC | CTG | AAG | AAT | AAC | TGG | GTG | TTG | CTG | TCC | ACC | GTG | GCC | GCG | 99 |
|---|---|---|---|---|---|---|---|---|---|---|---|---|---|---|---|---|
| Lys | Arg | Phe | Leu | Lys | Asn | Asn | Trp | Val | Leu | Leu | Ser | Thr | Val | Ala | Ala | |
| | | 15 | | | | 20 | | | | | 25 | | | | | |

| GTG | GTG | CTA | GGC | ATT | ACC | ACA | GGA | GTC | TTG | GTT | CGA | GAA | CAC | AGC | AAC | 147 |
|---|---|---|---|---|---|---|---|---|---|---|---|---|---|---|---|---|
| Val | Val | Leu | Gly | Ile | Thr | Thr | Gly | Val | Leu | Val | Arg | Glu | His | Ser | Asn | |
| | 30 | | | | 35 | | | | | 40 | | | | | | |

| CTC | TCA | ACT | CTA | GAG | AAA | TTC | TAC | TTT | GCT | TTT | CCT | GGA | GAA | ATT | CTA | 195 |
|---|---|---|---|---|---|---|---|---|---|---|---|---|---|---|---|---|
| Leu | Ser | Thr | Leu | Glu | Lys | Phe | Tyr | Phe | Ala | Phe | Pro | Gly | Glu | Ile | Leu | |
| 45 | | | | | 50 | | | | | 55 | | | | | 60 | |

| ATG | CGG | ATG | CTG | AAA | CTC | ATC | ATT | TTG | CCA | TTA | ATT | ATA | TCC | AGC | ATG | 243 |
|---|---|---|---|---|---|---|---|---|---|---|---|---|---|---|---|---|
| Met | Arg | Met | Leu | Lys | Leu | Ile | Ile | Leu | Pro | Leu | Ile | Ile | Ser | Ser | Met | |
| | | | | 65 | | | | | 70 | | | | | 75 | | |

| ATT | ACA | GGT | GTT | GCT | GCA | CTG | GAT | TCC | AAC | GTA | TCC | GGA | AAA | ATT | GGT | 291 |
|---|---|---|---|---|---|---|---|---|---|---|---|---|---|---|---|---|
| Ile | Thr | Gly | Val | Ala | Ala | Leu | Asp | Ser | Asn | Val | Ser | Gly | Lys | Ile | Gly | |
| | | | 80 | | | | | 85 | | | | | 90 | | | |

| CTG | CGC | GCT | GTC | GTG | TAT | TAT | TTC | TGT | ACC | ACT | CTC | ATT | GCT | GTT | ATT | 339 |
|---|---|---|---|---|---|---|---|---|---|---|---|---|---|---|---|---|
| Leu | Arg | Ala | Val | Val | Tyr | Tyr | Phe | Cys | Thr | Thr | Leu | Ile | Ala | Val | Ile | |
| | | 95 | | | | | 100 | | | | | 105 | | | | |

| CTA | GGT | ATT | GTG | CTG | GTG | GTG | AGC | ATC | AAG | CCT | GGT | GTC | ACC | CAG | AAA | 387 |
|---|---|---|---|---|---|---|---|---|---|---|---|---|---|---|---|---|
| Leu | Gly | Ile | Val | Leu | Val | Val | Ser | Ile | Lys | Pro | Gly | Val | Thr | Gln | Lys | |
| | 110 | | | | | 115 | | | | | 120 | | | | | |

| GTG | GGT | GAA | ATT | GCG | AGG | ACA | GGC | AGC | ACC | CCT | GAA | GTC | AGT | ACG | GTG | 435 |
|---|---|---|---|---|---|---|---|---|---|---|---|---|---|---|---|---|
| Val | Gly | Glu | Ile | Ala | Arg | Thr | Gly | Ser | Thr | Pro | Glu | Val | Ser | Thr | Val | |
| 125 | | | | | 130 | | | | | 135 | | | | | 140 | |

| GAT | GCC | ATG | TTA | GAT | CTC | ATC | AGG | AAT | ATG | TTC | CCT | GAG | AAT | CTT | GTC | 483 |
|---|---|---|---|---|---|---|---|---|---|---|---|---|---|---|---|---|
| Asp | Ala | Met | Leu | Asp | Leu | Ile | Arg | Asn | Met | Phe | Pro | Glu | Asn | Leu | Val | |
| | | | | 145 | | | | | 150 | | | | | 155 | | |

| CAG | GCC | TGT | TTT | CAG | CAG | TAC | AAA | ACT | AAG | CGT | GAA | GAA | GTG | AAG | CCT | 531 |
|---|---|---|---|---|---|---|---|---|---|---|---|---|---|---|---|---|
| Gln | Ala | Cys | Phe | Gln | Gln | Tyr | Lys | Thr | Lys | Arg | Glu | Glu | Val | Lys | Pro | |
| | | | 160 | | | | | 165 | | | | | 170 | | | |

| CCC | AGC | GAT | CCA | GAG | ATG | AAC | ATG | ACA | GAA | GAG | TCC | TTC | ACA | GCT | GTC | 579 |
|---|---|---|---|---|---|---|---|---|---|---|---|---|---|---|---|---|
| Pro | Ser | Asp | Pro | Glu | Met | Asn | Met | Thr | Glu | Glu | Ser | Phe | Thr | Ala | Val | |
| | | 175 | | | | | 180 | | | | | 185 | | | | |

| ATG | ACA | ACT | GCA | ATT | TCC | AAG | AAC | AAA | ACA | AAG | GAA | TAC | AAA | ATT | GTT | 627 |
|---|---|---|---|---|---|---|---|---|---|---|---|---|---|---|---|---|
| Met | Thr | Thr | Ala | Ile | Ser | Lys | Asn | Lys | Thr | Lys | Glu | Tyr | Lys | Ile | Val | |
| | 190 | | | | | 195 | | | | | 200 | | | | | |

| GGC | ATG | TAT | TCA | GAT | GGC | ATA | AAC | GTC | CTG | GGC | TTG | ATT | GTC | TTT | TGC | 675 |
|---|---|---|---|---|---|---|---|---|---|---|---|---|---|---|---|---|
| Gly | Met | Tyr | Ser | Asp | Gly | Ile | Asn | Val | Leu | Gly | Leu | Ile | Val | Phe | Cys | |
| 205 | | | | | 210 | | | | | 215 | | | | | 220 | |

| CTT | GTC | TTT | GGA | CTT | GTC | ATT | GGA | AAA | ATG | GGA | GAA | AAG | GGA | CAA | ATT | 723 |
|---|---|---|---|---|---|---|---|---|---|---|---|---|---|---|---|---|
| Leu | Val | Phe | Gly | Leu | Val | Ile | Gly | Lys | Met | Gly | Glu | Lys | Gly | Gln | Ile | |
| | | | | 225 | | | | | 230 | | | | | 235 | | |

| CTG | GTG | GAT | TTC | TTC | AAT | GCT | TTG | AGT | GAT | GCA | ACC | ATG | AAA | ATC | GTT | 771 |
|---|---|---|---|---|---|---|---|---|---|---|---|---|---|---|---|---|
| Leu | Val | Asp | Phe | Phe | Asn | Ala | Leu | Ser | Asp | Ala | Thr | Met | Lys | Ile | Val | |
| | | | 240 | | | | | 245 | | | | | 250 | | | |

| CAG | ATC | ATC | ATG | TGT | TAT | ATG | CCA | CTA | GGT | ATT | TTG | TTC | CTG | ATT | GCT | 819 |
|---|---|---|---|---|---|---|---|---|---|---|---|---|---|---|---|---|
| Gln | Ile | Ile | Met | Cys | Tyr | Met | Pro | Leu | Gly | Ile | Leu | Phe | Leu | Ile | Ala | |
| | | 255 | | | | | 260 | | | | | 265 | | | | |

| | | | | | | | | | | | | | | | | |
|---|---|---|---|---|---|---|---|---|---|---|---|---|---|---|---|---|
| GGG | AAG | ATC | ATA | GAA | GTT | GAA | GAC | TGG | GAA | ATA | TTC | CGC | AAG | CTG | GGC | 867 |
| Gly | Lys | Ile | Ile | Glu | Val | Glu | Asp | Trp | Glu | Ile | Phe | Arg | Lys | Leu | Gly | |
| | 270 | | | | 275 | | | | | 280 | | | | | | |
| CTT | TAC | ATG | GCC | ACA | GTC | CTG | ACT | GGG | CTT | GCA | ATC | CAC | TCC | ATT | GTA | 915 |
| Leu | Tyr | Met | Ala | Thr | Val | Leu | Thr | Gly | Leu | Ala | Ile | His | Ser | Ile | Val | |
| 285 | | | | | 290 | | | | | 295 | | | | | 300 | |
| ATT | CTC | CCG | CTG | ATA | TAT | TTC | ATA | GTC | GTA | CGA | AAG | AAC | CCT | TTC | CGA | 963 |
| Ile | Leu | Pro | Leu | Ile | Tyr | Phe | Ile | Val | Val | Arg | Lys | Asn | Pro | Phe | Arg | |
| | | | | 305 | | | | | 310 | | | | | 315 | | |
| TTT | GCC | ATG | GGA | ATG | GCC | CAG | GCT | CTC | CTG | ACA | GCT | CTC | ATG | ATC | TCT | 1011 |
| Phe | Ala | Met | Gly | Met | Ala | Gln | Ala | Leu | Leu | Thr | Ala | Leu | Met | Ile | Ser | |
| | | | 320 | | | | | 325 | | | | | 330 | | | |
| TCC | AGT | TCA | GCA | ACA | CTG | CCT | GTC | ACC | TTC | CGC | TGT | GCT | GAA | GAA | AAT | 1059 |
| Ser | Ser | Ser | Ala | Thr | Leu | Pro | Val | Thr | Phe | Arg | Cys | Ala | Glu | Glu | Asn | |
| | | 335 | | | | | 340 | | | | | 345 | | | | |
| AAC | CAG | GTG | GAC | AAG | AGG | ATC | ACT | CGA | TTC | GTG | TTA | CCC | GTT | GGT | GCA | 1107 |
| Asn | Gln | Val | Asp | Lys | Arg | Ile | Thr | Arg | Phe | Val | Leu | Pro | Val | Gly | Ala | |
| | 350 | | | | | 355 | | | | | 360 | | | | | |
| ACA | ATC | AAC | ATG | GAT | GGG | ACC | GCG | CTC | TAT | GAA | GCA | GTG | GCA | GCG | GTG | 1155 |
| Thr | Ile | Asn | Met | Asp | Gly | Thr | Ala | Leu | Tyr | Glu | Ala | Val | Ala | Ala | Val | |
| 365 | | | | | 370 | | | | | 375 | | | | | 380 | |
| TTT | ATT | GCA | CAG | TTG | AAT | GAC | CTG | GAC | TTG | GGC | ATT | GGG | CAG | ATC | ATC | 1203 |
| Phe | Ile | Ala | Gln | Leu | Asn | Asp | Leu | Asp | Leu | Gly | Ile | Gly | Gln | Ile | Ile | |
| | | | | 385 | | | | | 390 | | | | | 395 | | |
| ACC | ATC | AGT | ATC | ACG | GCC | ACA | TCT | GCC | AGC | ATC | GGA | GCT | GCT | GGC | GTG | 1251 |
| Thr | Ile | Ser | Ile | Thr | Ala | Thr | Ser | Ala | Ser | Ile | Gly | Ala | Ala | Gly | Val | |
| | | | 400 | | | | | 405 | | | | | 410 | | | |
| CCC | CAG | GCT | GGC | CTG | GTG | ACC | ATG | GTG | ATT | GTG | CTG | AGT | GCC | GTG | GGC | 1299 |
| Pro | Gln | Ala | Gly | Leu | Val | Thr | Met | Val | Ile | Val | Leu | Ser | Ala | Val | Gly | |
| | | 415 | | | | | 420 | | | | | 425 | | | | |
| CTG | CCC | GCC | GAG | GAT | GTC | ACC | CTG | ATC | ATT | GCT | GTC | GAC | TGG | CTC | CTG | 1347 |
| Leu | Pro | Ala | Glu | Asp | Val | Thr | Leu | Ile | Ile | Ala | Val | Asp | Trp | Leu | Leu | |
| | 430 | | | | | 435 | | | | | 440 | | | | | |
| GAC | CGG | TTC | AGG | ACC | ATG | GTC | AAC | GTC | CTT | GGT | GAT | GCT | TTT | GGG | ACG | 1395 |
| Asp | Arg | Phe | Arg | Thr | Met | Val | Asn | Val | Leu | Gly | Asp | Ala | Phe | Gly | Thr | |
| 445 | | | | | 450 | | | | | 455 | | | | | 460 | |
| GGC | ATT | GTG | GAA | AAG | CTC | TCC | AAG | AAG | GAG | CTG | GAG | CAG | ATG | GAT | GTT | 1443 |
| Gly | Ile | Val | Glu | Lys | Leu | Ser | Lys | Lys | Glu | Leu | Glu | Gln | Met | Asp | Val | |
| | | | | 465 | | | | | 470 | | | | | 475 | | |
| TCA | TCT | GAA | GTC | AAC | ATT | GTG | AAT | CCC | TTT | GCC | TTG | GAA | TCC | ACA | ATC | 1491 |
| Ser | Ser | Glu | Val | Asn | Ile | Val | Asn | Pro | Phe | Ala | Leu | Glu | Ser | Thr | Ile | |
| | | | 480 | | | | | 485 | | | | | 490 | | | |
| CTT | GAC | AAC | GAA | GAC | TCA | GAC | ACC | AAG | AAG | TCT | TAT | GTC | AAT | GGA | GGC | 1539 |
| Leu | Asp | Asn | Glu | Asp | Ser | Asp | Thr | Lys | Lys | Ser | Tyr | Val | Asn | Gly | Gly | |
| | | 495 | | | | | 500 | | | | | 505 | | | | |
| TTT | GCA | GTA | GAC | AAG | TCT | GAC | ACC | ATC | TCA | TTC | ACC | CAG | ACC | TCA | CAG | 1587 |
| Phe | Ala | Val | Asp | Lys | Ser | Asp | Thr | Ile | Ser | Phe | Thr | Gln | Thr | Ser | Gln | |
| 510 | | | | | 515 | | | | | 520 | | | | | | |
| TTC | TAGGGCCCCT | GGCTGCAGAT | GACTGGAAAC | AAGGAAGGAC | ATTTCGTGAG | | | | | | | | | | | 1640 |
| Phe | | | | | | | | | | | | | | | | |
| 525 | | | | | | | | | | | | | | | | |

AGTCATCTCA AACACGGCTT AAGGAAAAGA GAAA    1674

( 2 ) INFORMATION FOR SEQ ID NO:9:

( i ) SEQUENCE CHARACTERISTICS:
( A ) LENGTH: 525 amino acids
( B ) TYPE: amino acid
( D ) TOPOLOGY: linear ( i i ) MOLECULE TYPE: protein (xi) SEQUENCE DESCRIPTION: SEQ ID NO:9:

| Met 1 | Gly | Lys | Pro | Ala 5 | Arg | Lys | Gly | Cys | Pro 10 | Ser | Trp | Lys | Arg | Phe 15 | Leu |
|---|---|---|---|---|---|---|---|---|---|---|---|---|---|---|---|
| Lys | Asn | Asn | Trp 20 | Val | Leu | Leu | Ser | Thr 25 | Val | Ala | Ala | Val | Val 30 | Leu | Gly |
| Ile | Thr | Thr 35 | Gly | Val | Leu | Val | Arg 40 | Glu | His | Ser | Asn | Leu 45 | Ser | Thr | Leu |
| Glu | Lys 50 | Phe | Tyr | Phe | Ala 55 | Phe | Pro | Gly | Glu | Ile 60 | Leu | Met | Arg | Met | Leu |
| Lys 65 | Leu | Ile | Ile | Leu | Pro 70 | Leu | Ile | Ile | Ser | Ser 75 | Met | Ile | Thr | Gly | Val 80 |
| Ala | Ala | Leu | Asp | Ser 85 | Asn | Val | Ser | Gly | Lys 90 | Ile | Gly | Leu | Arg | Ala 95 | Val |
| Val | Tyr | Tyr | Phe 100 | Cys | Thr | Thr | Leu | Ile 105 | Ala | Val | Ile | Leu | Gly 110 | Ile | Val |
| Leu | Val | Val 115 | Ser | Ile | Lys | Pro | Gly 120 | Val | Thr | Gln | Lys | Val 125 | Gly | Glu | Ile |
| Ala | Arg 130 | Thr | Gly | Ser | Thr | Pro 135 | Glu | Val | Ser | Thr | Val 140 | Asp | Ala | Met | Leu |
| Asp 145 | Leu | Ile | Arg | Asn | Met 150 | Phe | Pro | Glu | Asn | Leu 155 | Val | Gln | Ala | Cys | Phe 160 |
| Gln | Gln | Tyr | Lys | Thr 165 | Lys | Arg | Glu | Glu | Val 170 | Lys | Pro | Pro | Ser | Asp 175 | Pro |
| Glu | Met | Asn | Met 180 | Thr | Glu | Glu | Ser | Phe 185 | Thr | Ala | Val | Met | Thr 190 | Thr | Ala |
| Ile | Ser | Lys 195 | Asn | Lys | Thr | Lys | Glu 200 | Tyr | Lys | Ile | Val | Gly 205 | Met | Tyr | Ser |
| Asp | Gly 210 | Ile | Asn | Val | Leu | Gly 215 | Leu | Ile | Val | Phe | Cys 220 | Leu | Val | Phe | Gly |
| Leu 225 | Val | Ile | Gly | Lys | Met 230 | Gly | Glu | Lys | Gly | Gln 235 | Ile | Leu | Val | Asp | Phe 240 |
| Phe | Asn | Ala | Leu | Ser 245 | Asp | Ala | Thr | Met | Lys 250 | Ile | Val | Gln | Ile | Ile 255 | Met |
| Cys | Tyr | Met | Pro 260 | Leu | Gly | Ile | Leu | Phe 265 | Leu | Ile | Ala | Gly | Lys 270 | Ile | Ile |
| Glu | Val | Glu 275 | Asp | Trp | Glu | Ile | Phe 280 | Arg | Lys | Leu | Gly | Leu 285 | Tyr | Met | Ala |
| Thr | Val 290 | Leu | Thr | Gly | Leu | Ala 295 | Ile | His | Ser | Ile | Val 300 | Ile | Leu | Pro | Leu |
| Ile 305 | Tyr | Phe | Ile | Val | Val 310 | Arg | Lys | Asn | Pro | Phe 315 | Arg | Phe | Ala | Met | Gly 320 |
| Met | Ala | Gln | Ala | Leu 325 | Leu | Thr | Ala | Leu | Met 330 | Ile | Ser | Ser | Ser | Ser 335 | Ala |
| Thr | Leu | Pro | Val 340 | Thr | Phe | Arg | Cys | Ala 345 | Glu | Glu | Asn | Asn | Gln 350 | Val | Asp |
| Lys | Arg | Ile 355 | Thr | Arg | Phe | Val | Leu 360 | Pro | Val | Gly | Ala | Thr 365 | Ile | Asn | Met |
| Asp | Gly 370 | Thr | Ala | Leu | Tyr | Glu 375 | Ala | Val | Ala | Ala | Val 380 | Phe | Ile | Ala | Gln |
| Leu 385 | Asn | Asp | Leu | Asp | Leu 390 | Gly | Ile | Gly | Gln | Ile 395 | Ile | Thr | Ile | Ser | Ile 400 |
| Thr | Ala | Thr | Ser | Ala 405 | Ser | Ile | Gly | Ala | Ala 410 | Gly | Val | Pro | Gln | Ala 415 | Gly |

| | | | | | | | | | | | | | | |
|---|---|---|---|---|---|---|---|---|---|---|---|---|---|---|
|Leu|Val|Thr|Met 420|Val|Ile|Val|Leu|Ser 425|Ala|Val|Gly|Leu|Pro 430|Ala|Glu|
|Asp|Val|Thr 435|Leu|Ile|Ile|Ala|Val 440|Asp|Trp|Leu|Leu|Asp 445|Arg|Phe|Arg|
|Thr|Met 450|Val|Asn|Val|Leu|Gly 455|Asp|Ala|Phe|Gly|Thr 460|Gly|Ile|Val|Glu|
|Lys 465|Leu|Ser|Lys|Lys 470|Glu|Leu|Glu|Gln|Met|Asp 475|Val|Ser|Ser|Glu|Val 480|
|Asn|Ile|Val|Asn|Pro 485|Phe|Ala|Leu|Glu|Ser 490|Thr|Ile|Leu|Asp 495|Asn|Glu|
|Asp|Ser|Asp|Thr 500|Lys|Lys|Ser|Tyr|Val 505|Asn|Gly|Gly|Phe 510|Ala|Val|Asp|
|Lys|Ser|Asp 515|Thr|Ile|Ser|Phe|Thr 520|Gln|Thr|Ser|Gln|Phe 525| | | |

( 2 ) INFORMATION FOR SEQ ID NO:10:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

CGCGGGTACC GCCATGGAGA AGAGCAAC                          28

( 2 ) INFORMATION FOR SEQ ID NO:11:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

CGCGTCTAGA TCACAGAACC GACTCCTTG                       29

( 2 ) INFORMATION FOR SEQ ID NO:12:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

CGCGGGTACC AATATGACTA AAAGCAATG                       29

( 2 ) INFORMATION FOR SEQ ID NO:13:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

```
CGCGTCTAGA CTACATCTTG GTTTCACTG                                                29
```

( 2 ) INFORMATION FOR SEQ ID NO:14:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

```
CGCGGGTACC ACCATGGCAT CTACGGAAG                                                29
```

( 2 ) INFORMATION FOR SEQ ID NO:15:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

```
CGCGTCTAGA TTATTTCTCA CGTTTCCAAG                                               30
```

( 2 ) INFORMATION FOR SEQ ID NO:16:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

```
CGCGGGTACC GCCATGGGGA AACCGGCG                                                 28
```

( 2 ) INFORMATION FOR SEQ ID NO:17:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

```
CGCGGGATCC CTAGAACTGT GAGGTCTG                                                 28
```